(12) United States Patent
Verploegen et al.

(10) Patent No.: US 9,150,658 B2
(45) Date of Patent: Oct. 6, 2015

(54) HUMAN ANTIBODIES AGAINST TISSUE FACTOR AND METHODS OF USE THEREOF

(75) Inventors: Sandra Verploegen, Nieuwegein (NL); David P. E. Satijn, Nieuwegein (NL); Rene Hoet, Zeist (NL); Paul Parren, Odijk (NL); Jan Van De Winkel, Zeist (NL); Vibeke Miller Breinholt, Frederiksberg (DK); Eva Ehrnrooth, Holte (DK); Ole Baadsgaard, Hellerup (DK); Tom Vink, Alphen aan den Rijn (NL); Willem Karel Bleeker, Amsterdam (NL); Mischa Houtkamp, Houten (NL); Maroeska Oudshoorn, Utrecht (NL); Rob N. De Jong, Utrecht (NL)

(73) Assignee: GENMAB A/S, Copenhagen (DK)

( * ) Notice: Subject to any disclaimer, the term of this patent is extended or adjusted under 35 U.S.C. 154(b) by 1034 days.

(21) Appl. No.: 13/133,811

(22) PCT Filed: Dec. 9, 2009

(86) PCT No.: PCT/EP2009/066755
§ 371 (c)(1),
(2), (4) Date: Aug. 26, 2011

(87) PCT Pub. No.: WO2010/066803
PCT Pub. Date: Jun. 17, 2010

(65) Prior Publication Data
US 2011/0300156 A1 Dec. 8, 2011

Related U.S. Application Data

(60) Provisional application No. 61/201,335, filed on Dec. 9, 2008.

(30) Foreign Application Priority Data

Dec. 9, 2008 (DK) ................................. 2008 01744

(51) Int. Cl.
*C07K 16/36* (2006.01)
*A61K 39/395* (2006.01)

(52) U.S. Cl.
CPC ............. *C07K 16/36* (2013.01); *A61K 39/395* (2013.01); *C07K 2316/96* (2013.01); *C07K 2317/21* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,545,806 A | 8/1996 | Lonberg et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,635,483 A | 6/1997 | Pettit et al. |
| 5,661,016 A | 8/1997 | Lonberg et al. |
| 5,663,149 A | 9/1997 | Pettit et al. |
| 5,770,429 A | 6/1998 | Lonberg et al. |
| 5,780,588 A | 7/1998 | Pettit et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,879,677 A | 3/1999 | del Zoppo |
| 6,214,345 B1 | 4/2001 | Firestone et al. |
| 7,605,235 B2 * | 10/2009 | Anderson et al. ............ 530/387.9 |
| 2005/0169927 A1 * | 8/2005 | Freskgaard et al. ........ 424/146.1 |
| 2005/0220793 A1 | 10/2005 | Anderson et al. |
| 2006/0034846 A1 | 2/2006 | Ezban et al. |
| 2009/0232734 A1 * | 9/2009 | Anderson et al. ............. 424/1.49 |
| 2010/0077497 A1 | 3/2010 | Deshpande et al. |

FOREIGN PATENT DOCUMENTS

| | | |
|---|---|---|
| EP | 1069185 B1 | 1/2001 |
| EP | 1374896 A1 | 1/2004 |
| EP | 1676574 A2 | 7/2006 |
| JP | 5-172811 | 7/1993 |
| JP | 5-244988 | 9/1993 |
| JP | 9-302000 | 11/1997 |
| JP | 2001-213804 | 8/2001 |
| WO | 88/07543 A1 | 10/1988 |
| WO | 89/12463 A1 | 12/1989 |
| WO | 92/03918 A1 | 3/1992 |
| WO | 92/22645 A1 | 12/1992 |
| WO | 93/12227 A1 | 6/1993 |
| WO | 94/05328 A1 | 3/1994 |
| WO | 94/11029 A1 | 5/1994 |
| WO | 94/25585 A1 | 11/1994 |
| WO | 96/01653 A1 | 1/1996 |

(Continued)

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Abdulkadir, Sarki A. et al., "Tissue Factor Expression and Angiogenesis in Human Prostate Carcinoma," Hum. Pathol., vol. 31(4):443-447 (2000).
Alley, Stephen C. et al., "Contribution of Linker Stability to the Activities of Anticancer Immunoconjugates," Bioconjugate Chem., vol. 19:759-765 (2008).
Amirkhosravi, A. et al., "The Importance of Platelets in the Expression of Monocyte Tissue Factor Antigen Measured by a New Whole Blood Flow Cytometric Assay," Thrombosis and Haemostasis, vol. 75(1):87-95 (1996).

(Continued)

*Primary Examiner* — Robert Landsman
(74) *Attorney, Agent, or Firm* — Nelson Mullins Riley & Scarborough LLP; Jane E. Remillard, Esq.; Christopher L. Frank

(57) ABSTRACT

Isolated human monoclonal antibodies which bind to human TF and related antibody-based compositions and molecules, are disclosed. Also disclosed are pharmaceutical compositions comprising the antibodies, and therapeutic and diagnostic methods for using the antibodies.

43 Claims, 43 Drawing Sheets

(56) References Cited

FOREIGN PATENT DOCUMENTS

| | | |
|---|---|---|
| WO | 96/40921 A1 | 12/1996 |
| WO | 98/24884 A1 | 6/1998 |
| WO | 98/40408 A1 | 9/1998 |
| WO | 01/09187 A2 | 2/2001 |
| WO | 01/14424 A2 | 3/2001 |
| WO | 01/27079 A2 | 4/2001 |
| WO | 01/70984 A2 | 9/2001 |
| WO | 02/43478 A2 | 6/2002 |
| WO | 03/020111 A2 | 3/2003 |
| WO | 03/029295 A1 | 4/2003 |
| WO | 03/037361 A2 | 5/2003 |
| WO | 03/037911 A2 | 5/2003 |
| WO | 03/070275 A1 | 8/2003 |
| WO | 03/093422 A2 | 11/2003 |
| WO | 2004/007557 A2 | 1/2004 |
| WO | 2004/010957 A2 | 2/2004 |
| WO | 2004/039842 A2 | 5/2004 |
| WO | 2004/041296 A2 | 5/2004 |
| WO | 2004/041302 A1 | 5/2004 |
| WO | 2004/064870 A2 | 8/2004 |
| WO | 2004/094475 A2 | 11/2004 |
| WO | 2004/110363 A2 | 12/2004 |
| WO | 2005/000896 A2 | 1/2005 |
| WO | 2005/001038 A2 | 1/2005 |
| WO | 2005/004793 A2 | 1/2005 |
| WO | 2005/020927 A2 | 3/2005 |
| WO | 2005/025623 A2 | 3/2005 |
| WO | 2005/072126 A2 | 8/2005 |
| WO | 2005/079766 A2 | 9/2005 |
| WO | 2005/081711 A2 | 9/2005 |
| WO | 2007/056352 A2 | 5/2007 |
| WO | 2007/076091 A2 | 7/2007 |
| WO | 2007/097810 A2 | 8/2007 |
| WO | 2008/030260 A2 | 3/2008 |
| WO | 2008/137382 A1 | 11/2008 |

OTHER PUBLICATIONS

Aras, Omer et al., "Induction and microparticle- and cell-associated intravascular tissue factor in human endotoxemia," Blood, vol. 103(12):4545-4553 (2004).
Chen, Jianzhu et al., "B cell development in mice that lack one or both immunoglobulin k light chain genes," The EMBO Journal, vol. 12(3):821-830 (1993).
Chen, Chaoyuan et al., "Characterization of Human Tissue Factor (TF)-Specific Monoclonal Antibodies Prepared USing a Rapid Immunization Protocol," Hybridoma, vol. 24(2):78-85 (2005).
Chen, Jianzhu et al., "Immunoglobulin gene rearrangement in B cell deficient mice generated by targeted deletion of the JH locus," International Immunology, vol. 5(6):647-656 (1993).
Chu, Arthur J., "Tissue factor mediates inflammation," Archives of Biochemistry adn Biophysics, vol. 440:123-132 (2005).
Doronina, Svetlana O. et al., "Development of potent monoclonal antibody auristatin conjugates for cancer therapy," Nature Biotechnology, vol. 21(7):778-941 (2003).
Doronina, Svetlana O. et al., "Enhanced Activity of Monomethylauristatin F through Monoclonal Antibody Delivery: Effects of Linker Technology on Efficacy and Toxicity," Bioconjugate Chem., vol. 17:114-124 (2006).
Drake, Thomas A. et al., "Selective Cellular Expression of Tissue Factor in Human Tissues," American Journal of Pathology, vol. 134(5):1087-1097 (1989).
Dubowchik, Gene M. et al., "Receptor-mediated and enzyme-dependent targeting of cytotoxic anticancer drugs," Pharmacology & Therapeutics, vol. 83:67-123 (1999).
Egorina, Elena M. et al., "Intracellular and Surface Distribution of Monocyte Tissue Factor, Application to Intersubject Variability," Arterioscler. Thromb. Vasc. Biol., vol. 25:1493-1498 (2005).
Fishwild, Dianne M. et al., "High-avidity human IgGk monoclonal antibodies from a novel strain of minilocus transgenic mice," Nature Biotechnology, vol. 14:845-851 (1996).
Forster, Yvonne et al., "Tissue factor and tumor: Clinical and laboratory aspects," Clinica Chimica Acta, vol. 364:12-21 (2006).
Genmab, "Development of ADCs against Tissue Factor for the treatment of Solid Tumors," World ADC Summit, Oct. 25-28, 2011, San Francisco, slideshow, 24 pages (2011).
Gessler, F. et al., "Inhibition of Tissue Factor/Protease-Activated Receptor-2 Signaling Limits Proliferation, Migration, and Invasion of Malignant Glioma Cells," Neuroscience, vol. 165:1312-1322 (2010).
Hamblett, Kevin J. et al., "Effects of Drug Loading on the Antitumor Activity of a Monoclonal Antibody Drug Conjugate," Clinical Cancer Research, vol. 10:7063-7070 (2004).
Harding, Fiona A. et al., "Class Switching in Human Immunoglobulin Transgenic Mice," Ann. N. Y. Acad. Sci., vol. 764:536-546 (1995).
Hjortoe, Gertrud M. et al., "Tissue factor-factor VIIa-specific up-regulation of IL-8 expression in MDA-MB-231 cells is mediated by PAR-2 and results in increases cell migration," Blood, vol. 103(8):3029-3037 (2004).
Hobbs, Jennifer E. et al., "Alternatively spliced human tissue factor promotes tumor growth and angiogenesis in a pancreatic cancer tumor model," Thrombosis Research, vol. 120(Suppl. 2):S13-S21 (2007).
Huang, Xianming et al., "Tumor Infarction in Mice by Antibody-Directed Targeting of Tissue Factor to Tumor Vasculature," Science, vol. 275(5299):547-550 (1997).
Jackson, Dowdy et al., "A Human Antibody-Drug Conjugate Targeting EphA2 Inhibits Tumor Growth in vivo," Cancer Res., vol. 68(22):9367-9374 (2008).
Kirchhofer, Daniel et al., "Epitope Location on Tissue Factor Determines the Anticoagulant Potency of Monoclonal Anti-tissue Factor Antibodies," Thromb. Haemost., vol. 84:1072-1081 (2000).
Lonberg, Nils et al., "Antigen-specific human antibodies from mice comprising four distinct genetic modifications," Nature, vol. 368(6474):856-859 (1994).
Lonberg, Nils et al., "Human Antibodies from Transgenic Mice," Int. Rev. Immunol., vol. 13:65-93 (1995).
Lonberg, N., "Transgenic Approaches to Human Monoclonal Antibodies," The Pharmacology of Monoclonal Antibodies, M. Rosenberg (Ed.), Springer-Verlag, Berlin, Chapter 3, pp. 49-101 (1994).
Mackman, Nigel et al., "Role of the Extrinsic Pathway of Blood Coagulation in Hemostasis and Thrombosis," Arterioscler. Thromb. Vasc. Biol., vol. 27:1687-1693 (2007).
Mandal, Samir K. et al., "Cellular localization and trafficking of tissue factor," Blood, vol. 107:4746-4753 (2006).
McDonagh, Charlotte F. et al., "Engineered antibody-drug conjugates with defined sites and stoichiometries of drug attachment," Protein Engineering Design & Selection, vol. 19(7):299-307 (2006).
Milsom, Chloe C. et al., "Tissue Factor Regulation by Epidermal Growth Factor Receptor and Epithelial-to-Mesenchymal Transitions: Effect on Tumor Initiation and Angiogenesis," Cancer Res., vol. 68(24):10068-10076 (2008).
Morrissey, James H. et al., "Monoclonal Antibody Analysis of Purified and Cell-associated Tissue Factor," Thrombosis Research, vol. 52:247-261 (1988).
Ngo, Cam V. et al., "CNTO 859, a humanized anti-tissue factor monoclonal antibody, is a potent inhibitor of breast cancer metastasis and tumor growth in xenograft models," Int. J. Cancer, vol. 120:1261-1267 (2007).
Pettit, Robin K. et al., "Specific Activities of Dolastatin 10 and Peptide Derivatives against *Cryptococcus neoformans*," Antimicrobial Agents and Chemotherapy, vol. 42(11):2961-2965 (1998).
Senter, Peter et al., "Immunoconjugates comprised of drugs with impaired cellular permeability: A new approach to targeted therapy," Proc. Amer. Assoc. Cancer Res., vol. 45, Abstract No. 623, 2 pages (2004).
Sun, Michael M.C. et al., "Reduction—Alkylation Strategies for the Modification of Specific Monoclonal Antibody Disulfides," Bioconjugate Chem., vol. 16:1282-1290 (2005).
Taylor, Lisa D. et al., "A transgenic mouse that expresses a diversity of human sequence heavy and light chain immunoglobulins," Nucleic Acids Research, vol. 20(23):6287-6295 (1992).

(56) References Cited

OTHER PUBLICATIONS

Taylor, Lisa D. et al., "Human immunoglobulin transgenes undergo rearrangement, somatic mutation and class switching in mice that lack endogenous IgM," International Immunology, vol. 6(4):579-591 (1994).

Tuaillon, Nadine et al., "Biased Utilization of DHQ52 and JH4 Gene Segments in a Human Ig Transgenic Minilocus Is Independent of Antigenic Selection," Journal of Immunology, vol. 152:2912-2920 (1994).

Verma, Sunil et al., "Trastuzumab Emtansine for HER2-Positive Advanced Breast Cancer," The New England Journal of Medicine, vol. 367(19):1783-1791 (2012).

Versteeg, Henri H. et al., "Inhibition of tissue factor signaling suppresses tumor growth," Blood, vol. 111:190-199 (2008).

Vine, Andrew K., "Recent Advances in Haemostasis and Thrombosis," Retina, vol. 29:1-7 (2009).

Wang, Baiyang et al., "Radiotherapy of Human Xenograft NSCLC Tumors in Nude Mice with a 90Y-Labeled Anti-Tissue Tissue Factor Antibody," Cancer Biotherapy & Radiopharmaceuticals, vol. 20(3):300-309 (2005).

Woyke, Tanja et al., "In Vitro Activities and Postantifungal Effects of the Potent Dolastatin 10 Derivative Auristatin PHE," Antimicrobial Agents and Chemotherapy, vol. 45(12):3580-3584 (2001).

Yu, Joanne L. et al., "Oncogenic events regulate tissue factor expression in colorectal cancer cells: implications for tumor progression and angiogenesis," Blood, vol. 105:1734-1741 (2005).

International Search Report and Written Opinion for Application No. PCT/EP2009/066755, dated Jun. 28, 2010.

\* cited by examiner

Figure 1

Alignment of sequences

Sequences of the antibodies of the present invention are given below.
SEQ ID NO. is listed in parentheses to the right of the sequence.
CDR1, CDR2 and CDR3 according to Kabat are highlighted: sequences in italics represent CDR1, underlined sequences represent CDR2, bold sequences represent CDR3.

VH:

```
                |--CDR1--|                        |--CDR2--|                                              |------CDR3------|
EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARIHRGAGYSSSWPGAFDIWGQGTMVTVSS  VH1015-013 (1)

QVQLVESGGGVVQPGRSLRLSCVASGFTVSNDGMHWVRQAPGKGLEWVALIWYDGVNKNYADSVKGRFTISRDKSKNTLYLQMNSLRAEDTAVYYCARRPGT-----------FYGLDVWGQGTTVTVSS VH1015-114 (5)

EVQLLESGGGLVQPGGSLRLSCAASGFTFSSNYAMSWVRQAPGKGLEWVSSISGSGDYIYYTDSVKGRFTISRDNSKNTLYLQMNSLRAEDTAVYYCARSPWG----------YYLDSWGQGILVAVSS VH1015-011 (9)

EVQLLESGGGLVQPGGSLRLSCAASGFTFSSYAMSWVRQAPGKGLEWVSAISGSGDSTNYADSVKGRFTISRDNSKNTLYLQMNSLRAEDTAVYYCAKDGYFL----------LWIFDLWGRGTLVTVSS VH1015-017 (13)

EVQLLESGGGLVQPGGSLRLSCAASGFTFSSYGMSWVRQAPGKGLEWVSVISGSGGTTYYADSVKGRFTISRDNSKNTLYLQMNSLRAEDTAVYYCAKAPWT---------YYFDYWGQGTLVTVSS VH1015-042 (17)

EVQLLESGGGLVQPGGSLRLSCAASGFTFENNYAMSWVRQAPGKGLEWVSSISGSGGRTYYADSVKGRFTISRDNSKNTLFLQMNSLRAEDTAVYYCAKTPWG---------YYFDYWGQGTLVTVSS VH1015-092 (21)

EVQLLESGGGLVQPGGSLRLSCAASGFTFSNIYAMSWVRQAPAKGLDWVSGISGSGVTTYYADSVKGRFTISRDNSKDTLYLQMNSLRAEDTAVYFCAKTPWG---------YYFDYWGQGILVAVSS VH1015-101 (25)

QVQLVQSGAEVKKPGSSVKVSCKAPRGTFSSYYIISWVRQAPGQGLEWMGRIIPLGVANYAQKFQGRVTITADKSTSTAYMELSSLRSEDTAVYYCAREGD------RR---YFDYWGQGTLVTVSS VH1015-003 (29)

QVQLVESGGGVVQPGRSLRLSCAASGFTFSRIYAMHWVRQAPGKGLEWVAVISNDGYNDYYADSVKGRFTVSRDNSKNTLYLQMNSLRAEDTAVYYCARDGQLG---------RGYFDYWGQGTLVTVSS VH1015-025 (33)

QVQLVESGGGVVQPGRSLRLSCPASGFTFSIYAMHWVRQAPGKGLEWVAVYSNDGYNKYYADSVKGRFTISRDNSKDTLYLQMNSLRAEDTAVYYCARDGQLG---------RGYFDYWGQGTLVTVSS VH1015-109 (37)
```

Figure 1 - continued

QVQLVESGGGVVQPGRSLRLSCAASGFTFSDYAMHWVRQAPGKGLEWVAVIPYDGDNKYYADSVKGRFTISRDNSKNTLYLQMNSLRAEDTAVYYCAREDNG----------LEVDYWGQGALVTVSS VH1015-044 (41)

EVQLVQSGAEVKKPGESLKISCKGSFYSFTSCHIGWVRQMPGKGLEWMGIIYPGDSDTRYSPSFQGQVTISADKSISTAYLQWSSLKASDTAMYYCARHKLGMDHD-------AFDIWGQGTMVTVSS VH1015-087 (45)

QVQLVQSGAEVRKPGSSVKVSCKASGGSFNNYPIFWVRQAPGCQGFEWMGRIIPILGITAYAQKFQGRVTITADKSTSTAYMELNSLRSEDTAVYYCAGGDD------LD--AFDIWGQGTMVSVSS VH1015-098 (49)

QVQLVESGGGVVQPGRSLRLSCAGSGFTFNRYAMYWVRQAPGKGLDWVAVISNDGINKYYADSVKGRFTISRDNSKNTLYLQMNSLRAEDTAVYYCARDHTMV------RGAFDYWGQGTLVTVSS VH1015-111 (53)

```
                    |-CDR1--|                    |CDR2|                              |---CDR3----|
DIQMTQSPSSLSASVGDRVTITCRASQGISR-WLAWYQQKPEKAPKSLIIYAASSLQSGVPSRFSGSGSGTDFTLTITSSLQPEDFATYYCQQYDSDP-LTFGQGTRLEIK VL1015-013 (57)
EIVLTQSPGTLSLSPGERATLSCRASQSVSSY-LAWYQQKPGQAPRLLIYGASSRATGIPDRFSGSGSGTDFTLTISRLEPEDFAVYYCQQYGSS--LTFGGGTKVEIK VL1015-114 (61)
DIQMTQSPPSLSASAGDRVTITCRASQGISS-RLAWYQQKPEKAPKSLIIYAASSLQSGVPSRFSGSGSGTDFTLTISSLQPEDFATYYCQQYNSYP-YTFGQGTKLEIK VL1015-011 (65)
EIVLTQSPGTLSLSPGERATLSCRASQSVRSSY-LAWYQQKPGQAPRLLIYGASSRATGIPDRFSGSGSGTDFTLTISRLEPEDFAVYYCQQYGSSP-RTFGQGTKVEIK VL1015-017 (69)
EIVLTQSPGTLSLSPGERATLSCRASQSVGSSSLAWYQQKPGQAPRLLIYGASSRATGIPDRFSGSGSGTDFTLTISRLEPEDFAVYYCQQYGSSP-RTFGQGTKVEIK VL1015-042 (73)
DIQMTQSPSSLSASVGDRVTITCRASQGISS-RLAWYQQKPEKAPKSLIIYAASSLQSGVPSRFSGSGSGTDFTLTISSLQPEDFATYYCQQYNSYP-YTFGQGTKLEIK VL1015-092 (77)
AIQLTQSPSSLSASVGDRVTITCRASQDISS-ALAWYQQKPGKAPKLLIYDASILESGVPSRFSGSGSGTDFTLTISSLQPEDFATYYCQQFNSYP-LTFGGGTKVEIK VL1015-101 (81)
EIVLTQSPATLSLSPGERATLSCRASQSVSS-YLAWYQQKPGQAPRLLIYDASNRATGIPARFSGSGSGTDFTLTISSLEPEDFAVYYCQQRSNWP-LTFGGGTKVEIK VL1015-003 (85)
EIVLTQSPATLSLSPGERATLSCRASQSVSS-YLAWYQQKPGQAPRLLIYDASNRATGIPARFSGSGSGTDFTLTISSLEPEDFAVYYCQQYNSYP-LTFGGGTKVEIK VL1015-025 (89)
AIQLTQSPSSLSASVGDRVTITCRASQGINS-ALAWYQQKPGKAPKLLIYDASSLESGVPSRFSGSGSGTDFTLTISSLQPEDFATYYCQQFNSYP-LTFGGGTKVEIK VL1015-109 (93)
DIQMTQSPSSLSASVGDRVTITCRASQGISS-WLAWYQQKPEKAPKSLIIYAASSLQSGVPSRFSGSGSGTDFTLTISSLQPEDFATYYCQQYNSYP-PTFGQGTVEVK VL1015-044 (97)
DIQMTQSPSSLSASVGDRVTITCRASQGISS-WLAWYQQKPEKAPKSLIIYAASSLQSGVPSRFSGSGSGTDFTLTISSLQPEDFATYYCQQYNSYP-PTFGQGTVEVK VL1015-087 (101)
DIQMTQSPSSLSASVGDRVTITCRASQGISS-WLAWYQQKPEKAPKSLIIYAASSLQSGVPSRFSGSGSGTDFTLTISSLQPEDFATYYCQQYNSYP-YTFGQGTKLEIK VL1015-098 (105)
EIVLTQSPATLSLSPGERATLSCRASQSVSS-YLAWYQQKPGQAPRLLIYDASNRATGIPARFSGSGSGTDFTLTISSLEPEDFAVYYCQQRSNWP-LTFGGGTKVEIK VL1015-111 (109)
```

Figure 2

SEQ ID NO: 113: The amino acid sequence of the wildtype C_H region of human IgG4.

```
  1 ASTKGPSVFP LAPCSRSTSE STAALGCLVK DYFPEPVTVS WNSGALTSGV
 51 HTFPAVLQSS GLYSLSSVVT VPSSSLGTKT YTCNVDHKPS NTKVDKRVES
101 KYGPPCPSCP APEFLGGPSV FLFPPKPKDT LMISRTPEVT CVVVDVSQED
151 PEVQFNWYVD GVEVHNAKTK PREEQFNSTY RVVSVLTVLH QDWLNGKEYK
201 CKVSNKGLPS SIEKTISKAK GQPREPQVYT LPPSQEEMTK NQVSLTCLVK
251 GFYPSDIAVE WESNGQPENN YKTTPPVLDS DGSFFLYSRL TVDKSRWQEG
301 NVFSCSVMHE ALHNHYTQKS LSLSLGK
```

The Sequence in italics represents the CH1 region, highlighted sequence represents the hinge region, regular sequence represents the CH2 region and underlined sequence represents the CH3 region.

SEQ ID NO: 114: The amino acid sequence of the hingeless C_H region of a human IgG4.

```
  1 ASTKGPSVFP LAPCSRSTSE STAALGCLVK DYFPEPVTVS WNSGALTSGV
 51 HTFPAVLQSS GLYSLSSVVT VPSSSLGTKT YTCNVDHKPS NTKVDKRVAP
101 EFLGGPSVFL FPPKPKDTLM ISRTPEVTCV VVDVSQEDPE VQFNWYVDGV
151 EVHNAKTKPR EEQFNSTYRV VSVLTVLHQD WLNGKEYKCK VSNKGLPSSI
201 EKTISKAKGQ PREPQVYTLP PSQEEMTKNQ VSLTCLVKGF YPSDIAVEWE
251 SNGQPENNYK TTPPVLDSDG SFFLYSRLTV DKSRWQEGNV FSCSVMHEAL
301 HNHYTQKSLS LSLGK
```

Figure 3
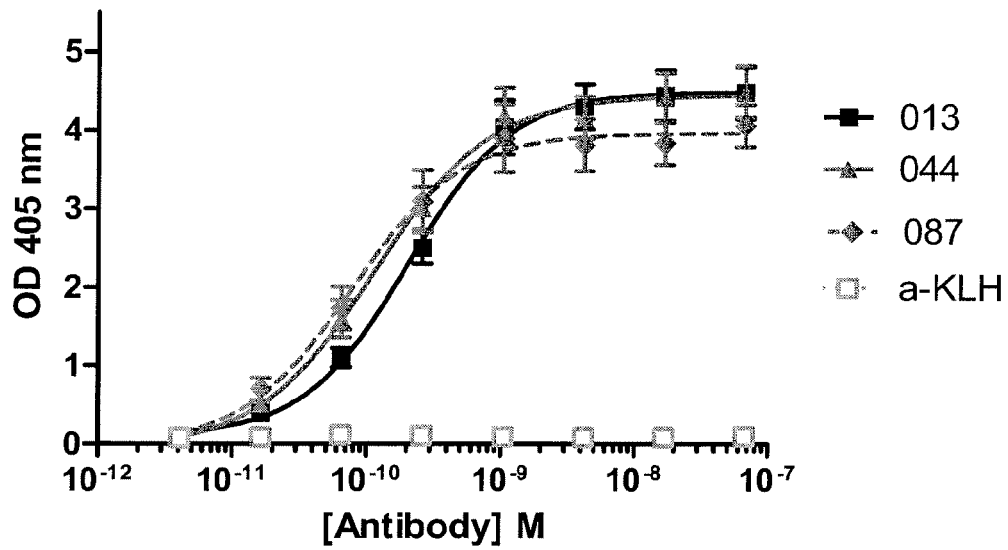
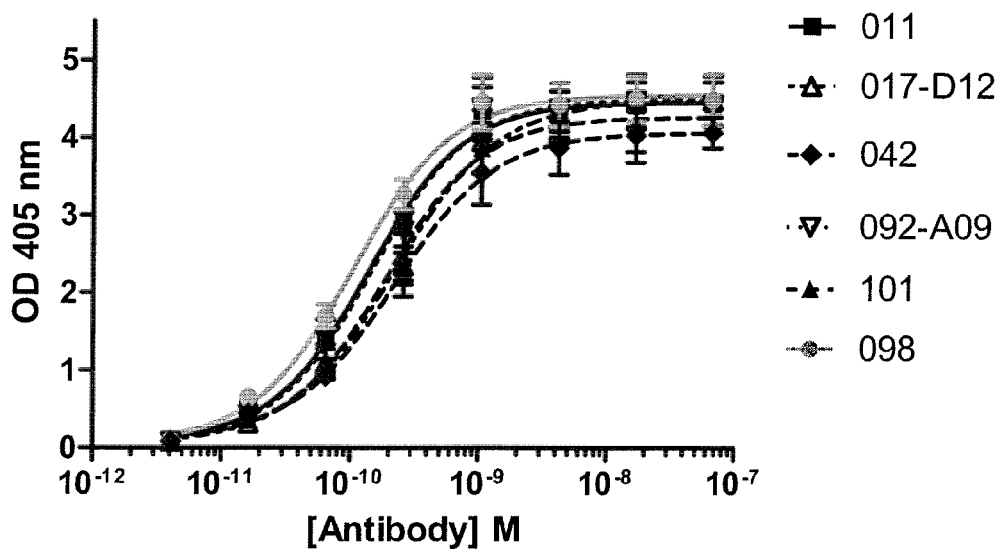

Figure 3: Binding of anti-TF HuMabs to the extra cellular domain of TF in ELISA_Binding was determined by ELISA.

Figure 4
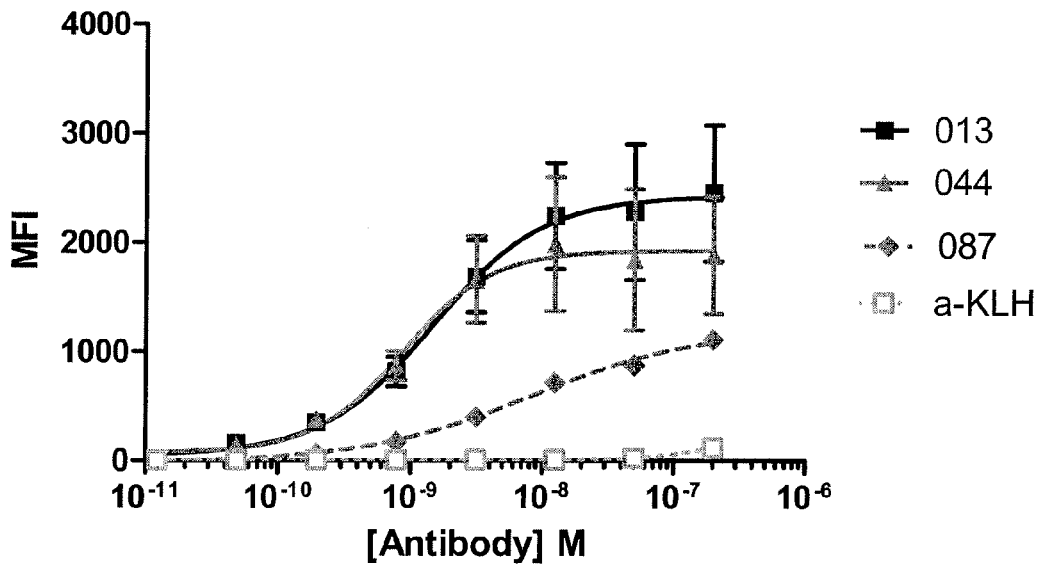
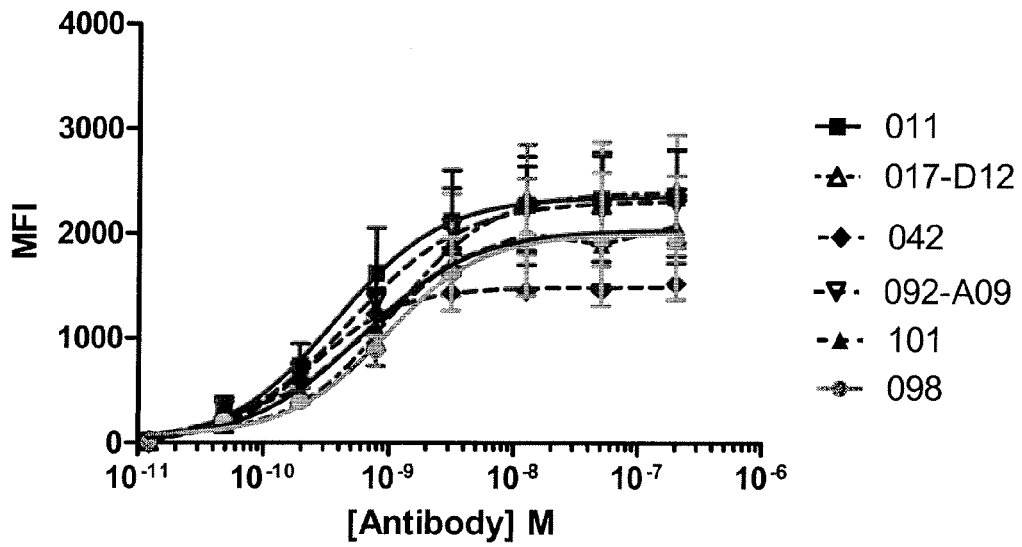

Figure 4a, 4b, 4c: Binding of anti-TF HuMabs to membrane-bound TF on MDA-MD-231 cells. Binding was determined by FACS analysis.

Figure 5
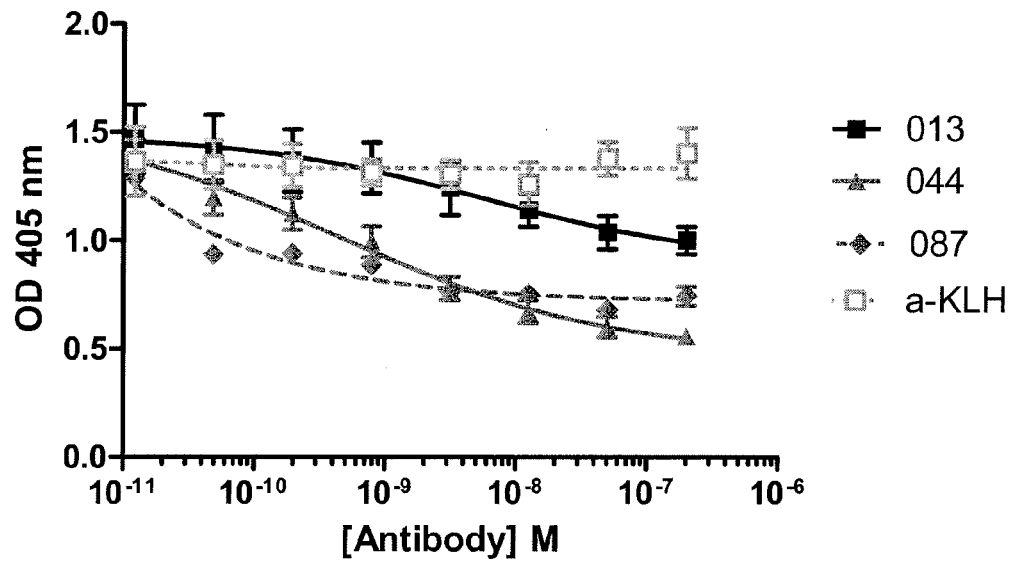
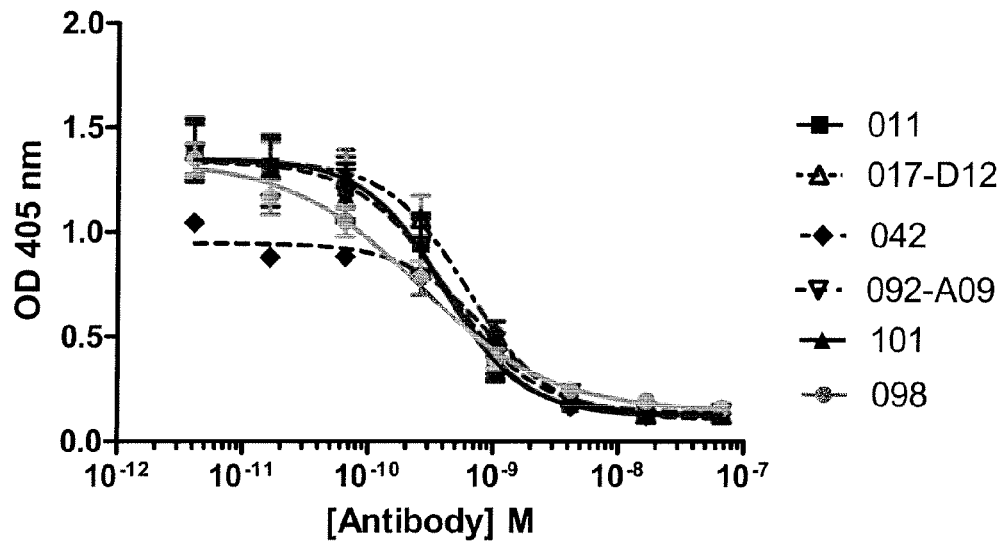

Figure 5: Inhibition of FVIIa binding to TF. FVIIa binding, and the inhibition by TF specific HuMabs of this binding, was measured by ELISA.

Figure 6
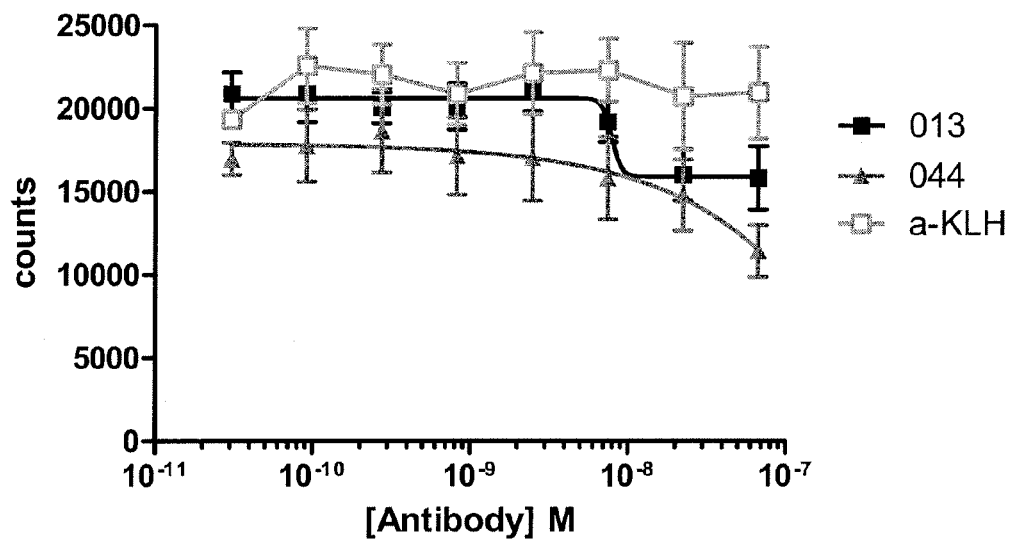
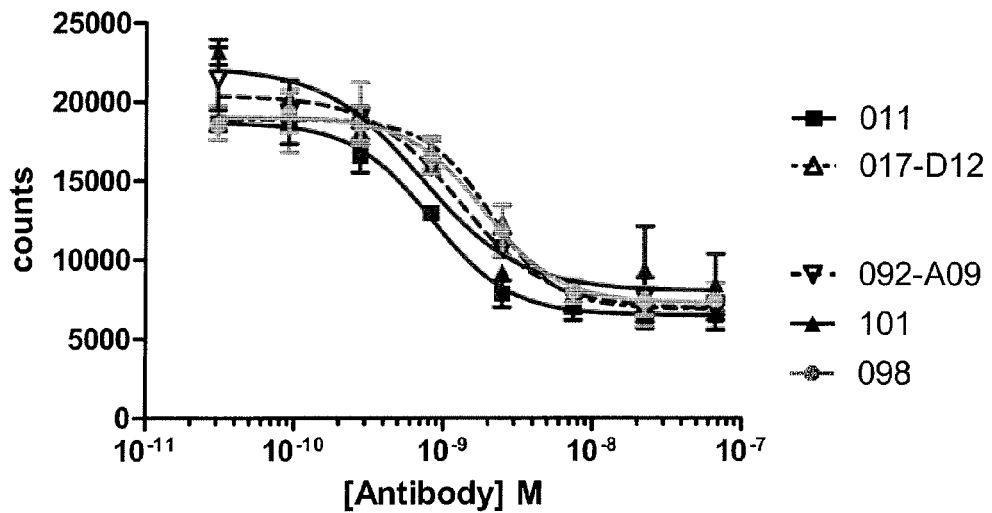

Figure 6 continued...
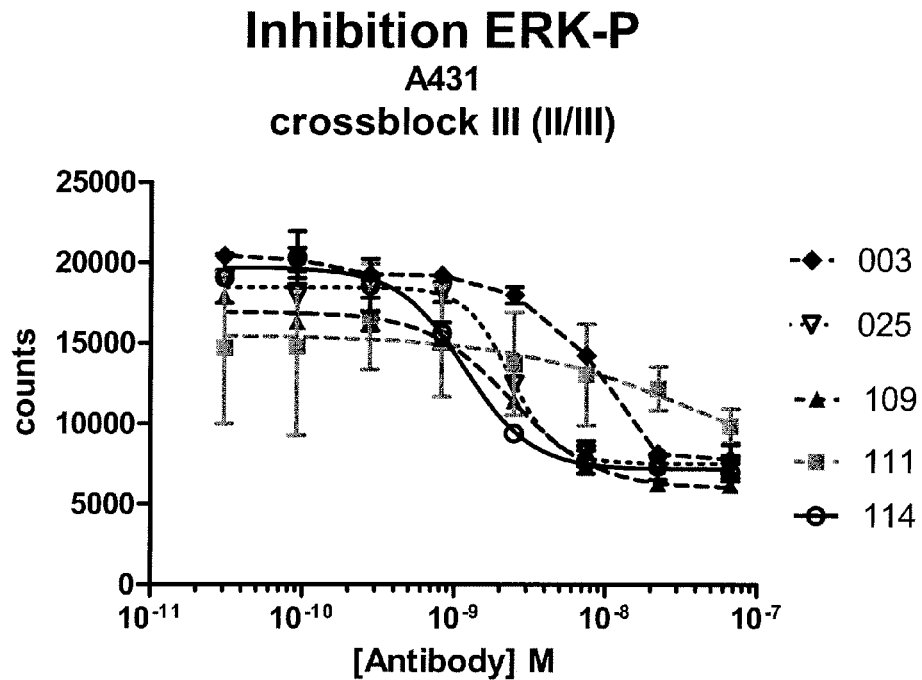
Figure 6: Inhibition of FVIIa induced ERK phosphorylation.
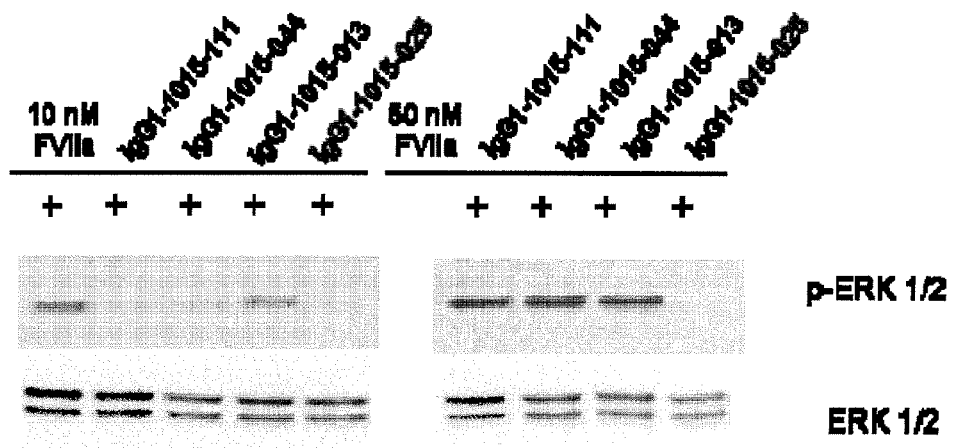
Figure 6A. Inhibition of FVIIa induced ERK phosphorylation, using Western blot analysis.

Figure 7
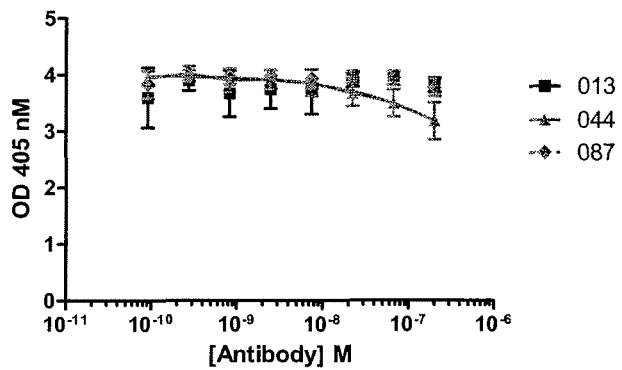
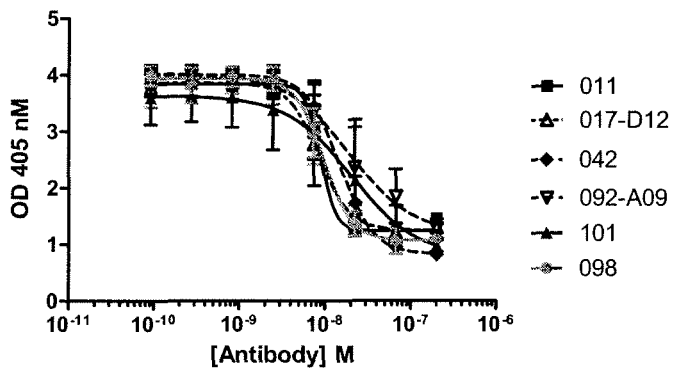
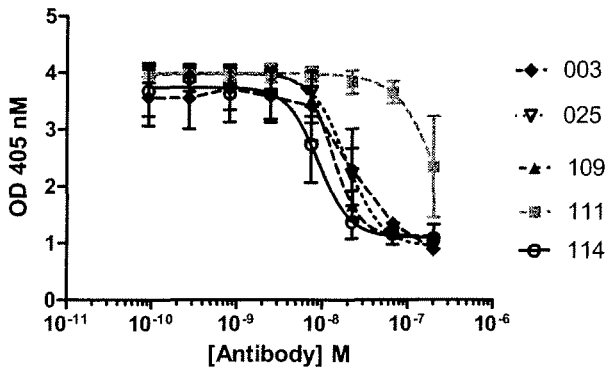

Figure 7 continued...

Figure 7. Inhibition of FVIIa induced IL-8 release. MDA-MB-231 were cultured in serum free medium, TF specific antibodies and FVIIa were added. FVIIa induced IL-8 was measured by ELISA.

Figure 8
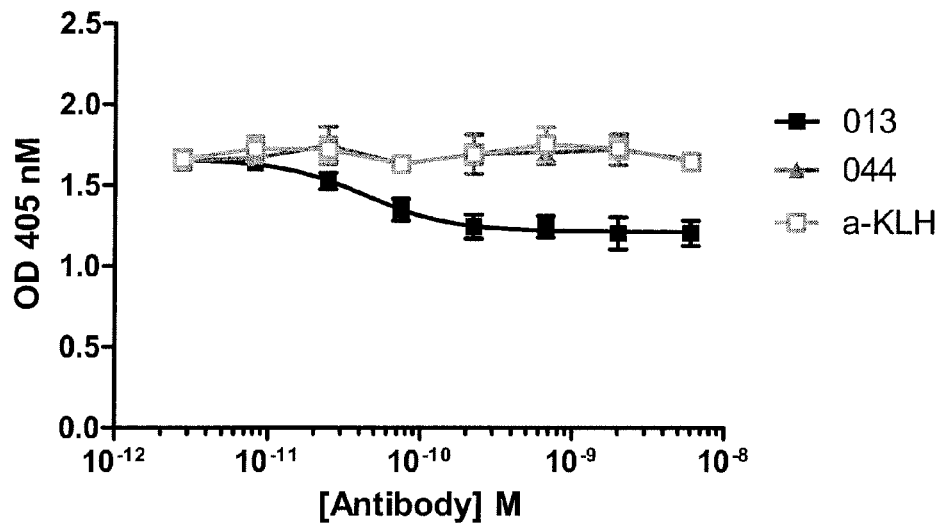
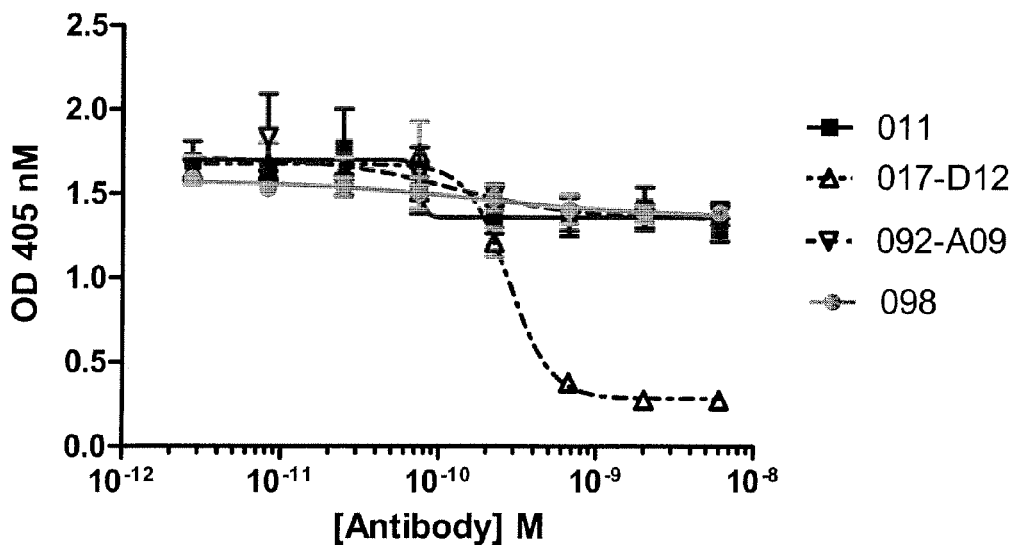

Figure 8. Inhibition of FXa generation. The ability of TF specific HuMabs to inhibit FXa generation was tested in an assay in which conversion of FX into FXa by the TF/FVIIa complex is measured using a colometric FXa specific substrate.

Figure 9
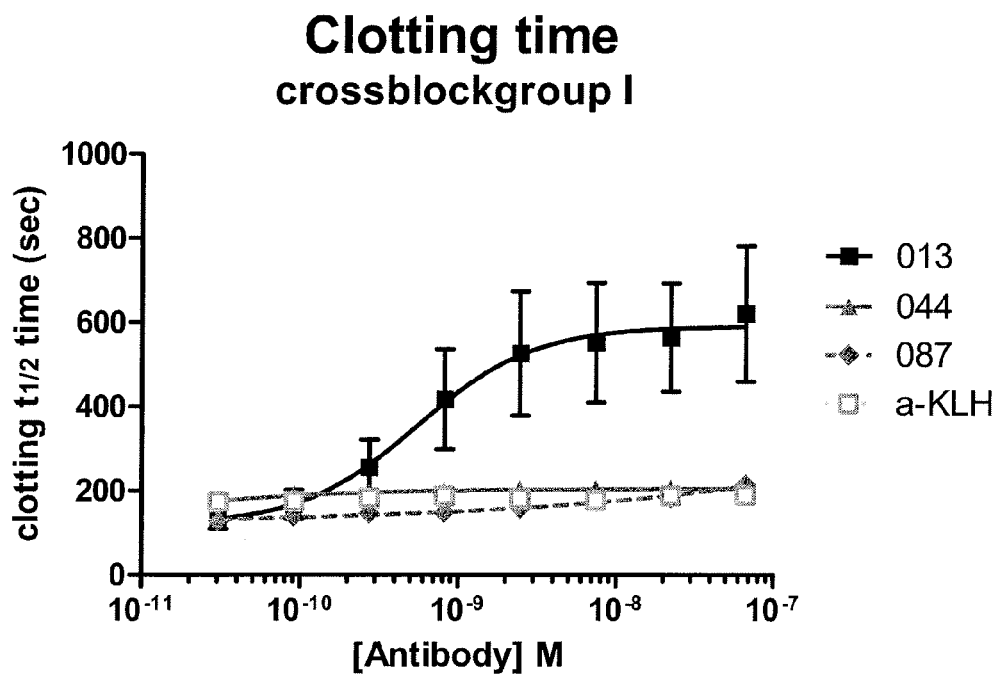
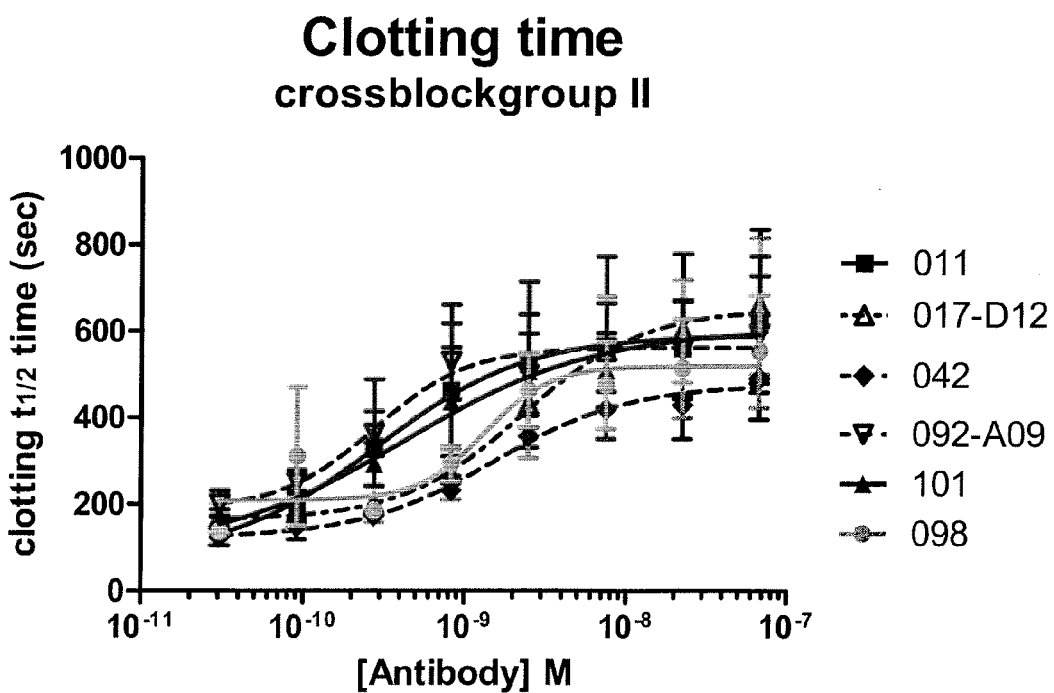

Figure 9. Inhibition of blood coagulation. Inhibition of blood coagulation by TF-HuMabs was measured in an assay determining TF induced clotting time.

Figure 10
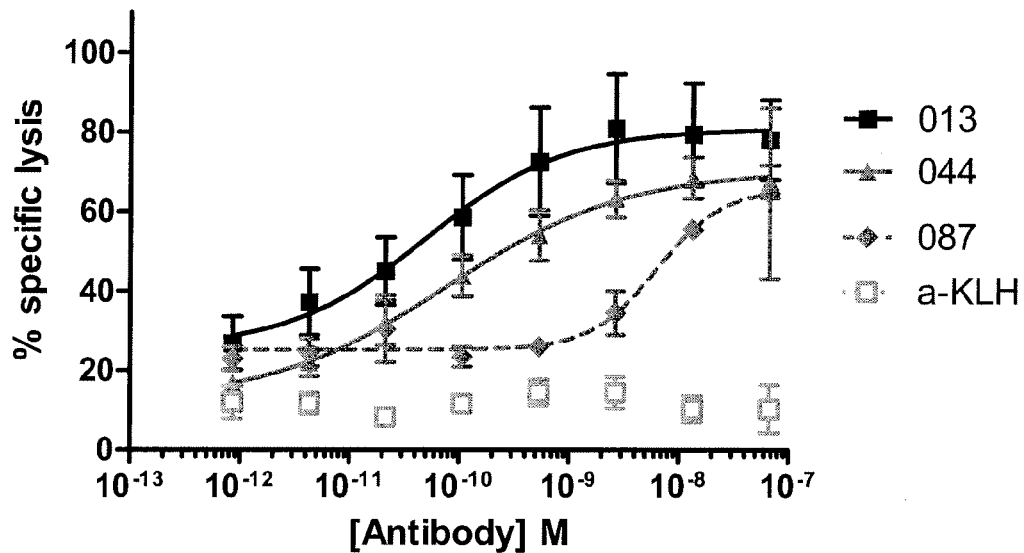
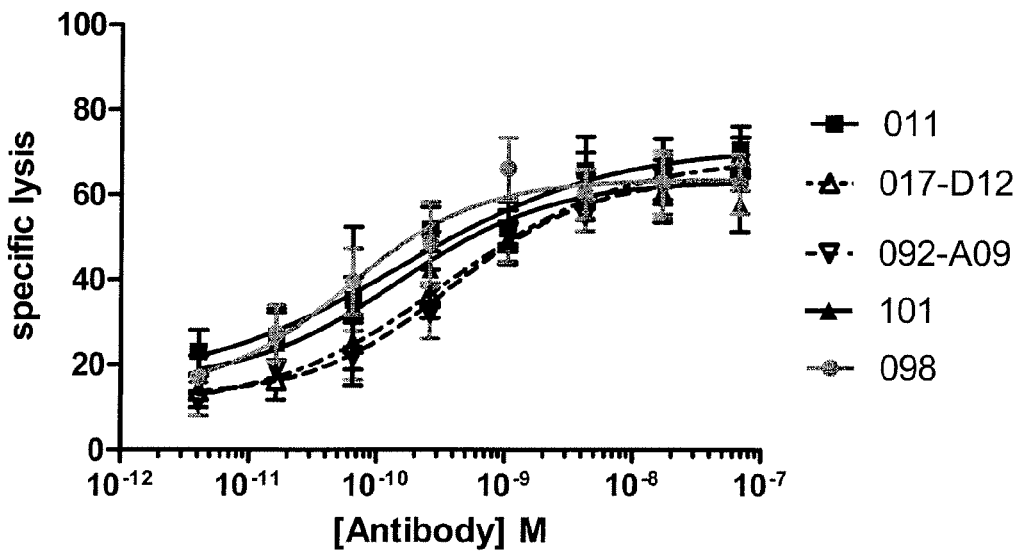

Figure 10: TF-HuMabs induced lysis of Bx-PC3 cells by ADCC.

Figure 11: Complement deposition

Figure 12: Immunohistochemical analysis of binding of TF-HuMabs to normal human kidney.

Figure 13. Immunohistochemical analysis of binding of TF-HuMabs to pancreatic tumors.

Figure 14. In vivo efficacy of TF-HuMabs in established MDA-MB-231 tumor xenograft in mammary fat pads of SCID mice.

Figure 15: Bleeding time (minutes), determined in cynomolgus monkeys upon intravenous injections of TF-specific HuMab 011. The antibody was administered on day 1 (0 mg/kg), 8 (1 mg/kg), 15 (10 mg/kg) and 22 (100 mg/kg). Functional bleeding time and blood loss was determined 1, 24 and 120 hours post dosing Repeated measures 2-way ANOVA, followed by Bonferroni posthoc testing:
111 vs KLH: from d28 onwards: P<0.05, from d32 onwards: P<0.01.

Figure 16 - continued
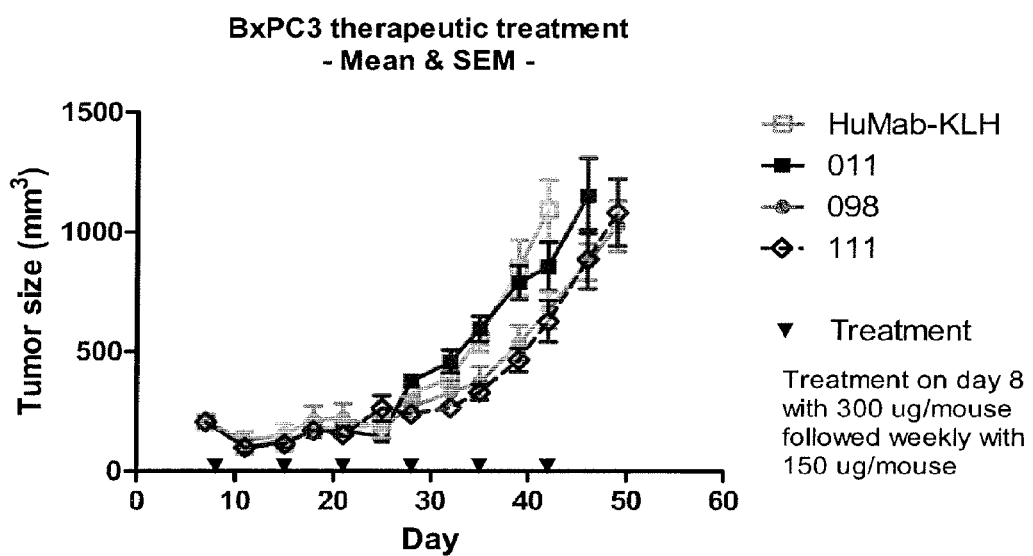
Repeated measures 2-way ANOVA, followed by Bonferroni posthoc testing:
111 vs KLH: from d35 onwards: P<0.05

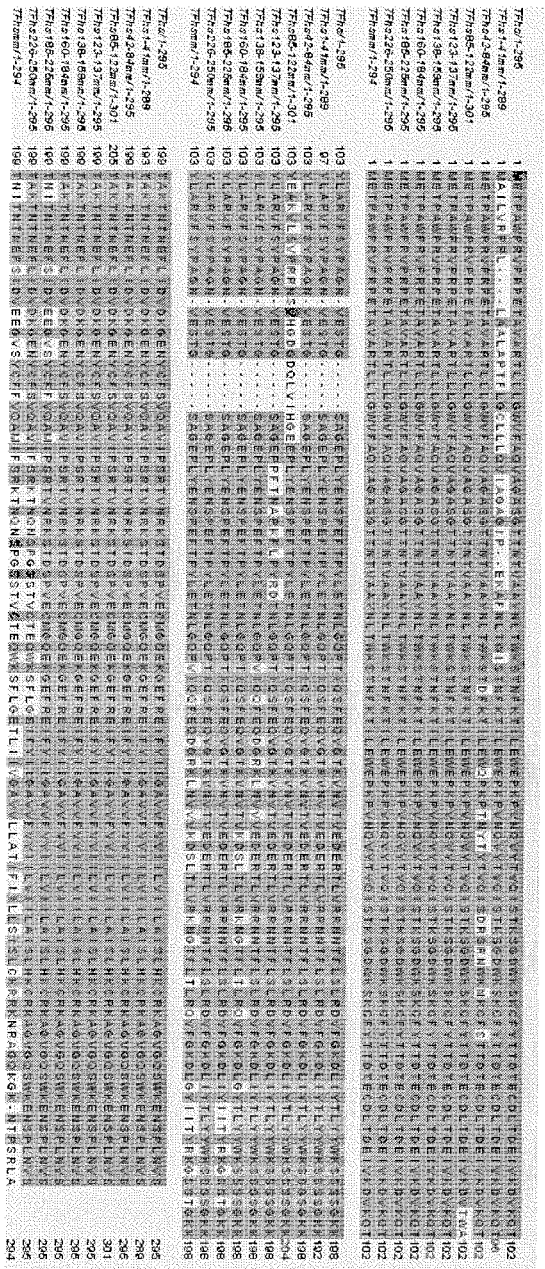
Figure 17 A. TFhs shuffle construct, containing TFmm domains

Figure 17 B. TFmm shuffle construct, containing TFhs domains

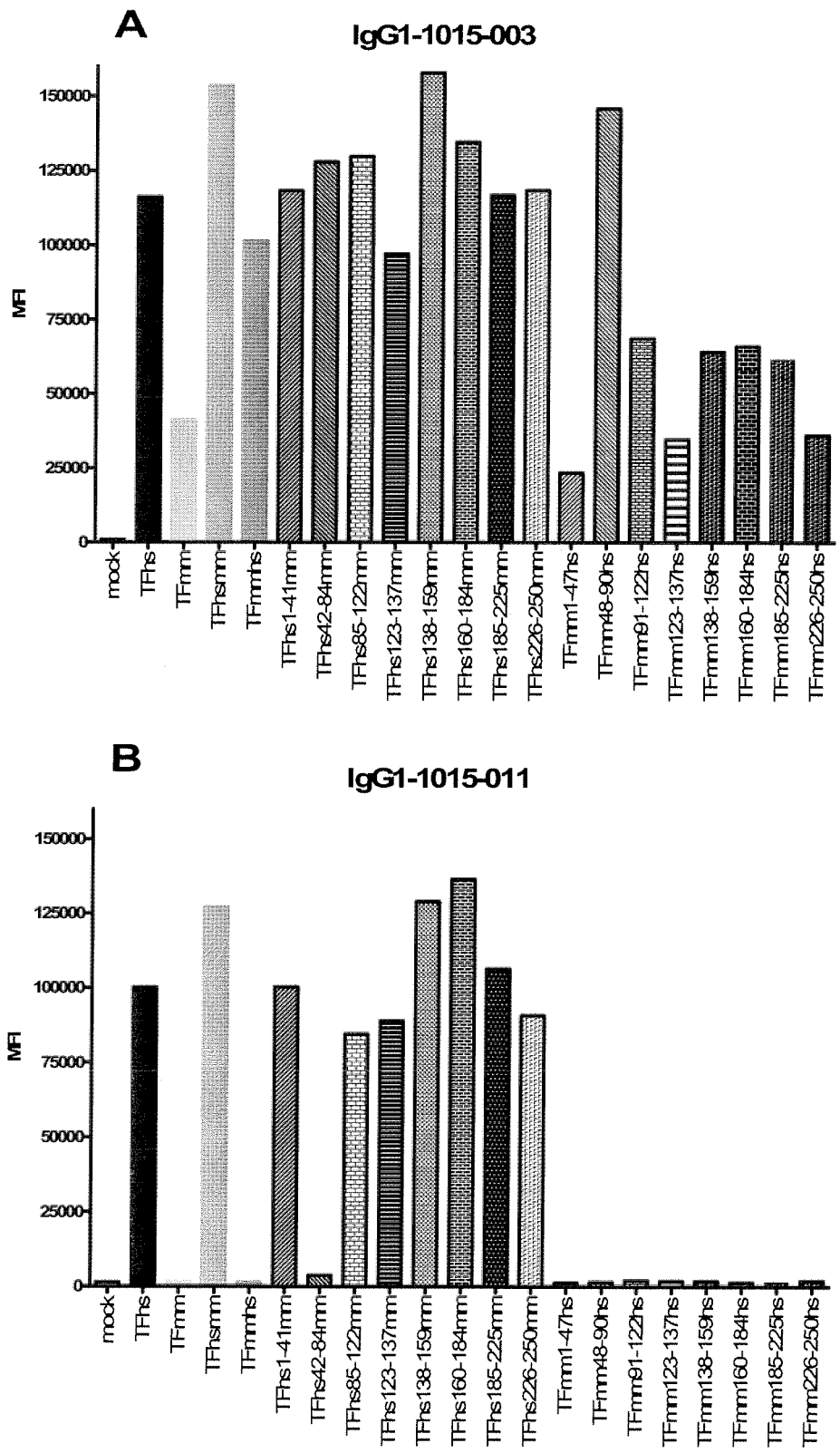
Figure 18 - continued

Figure 18 - continued
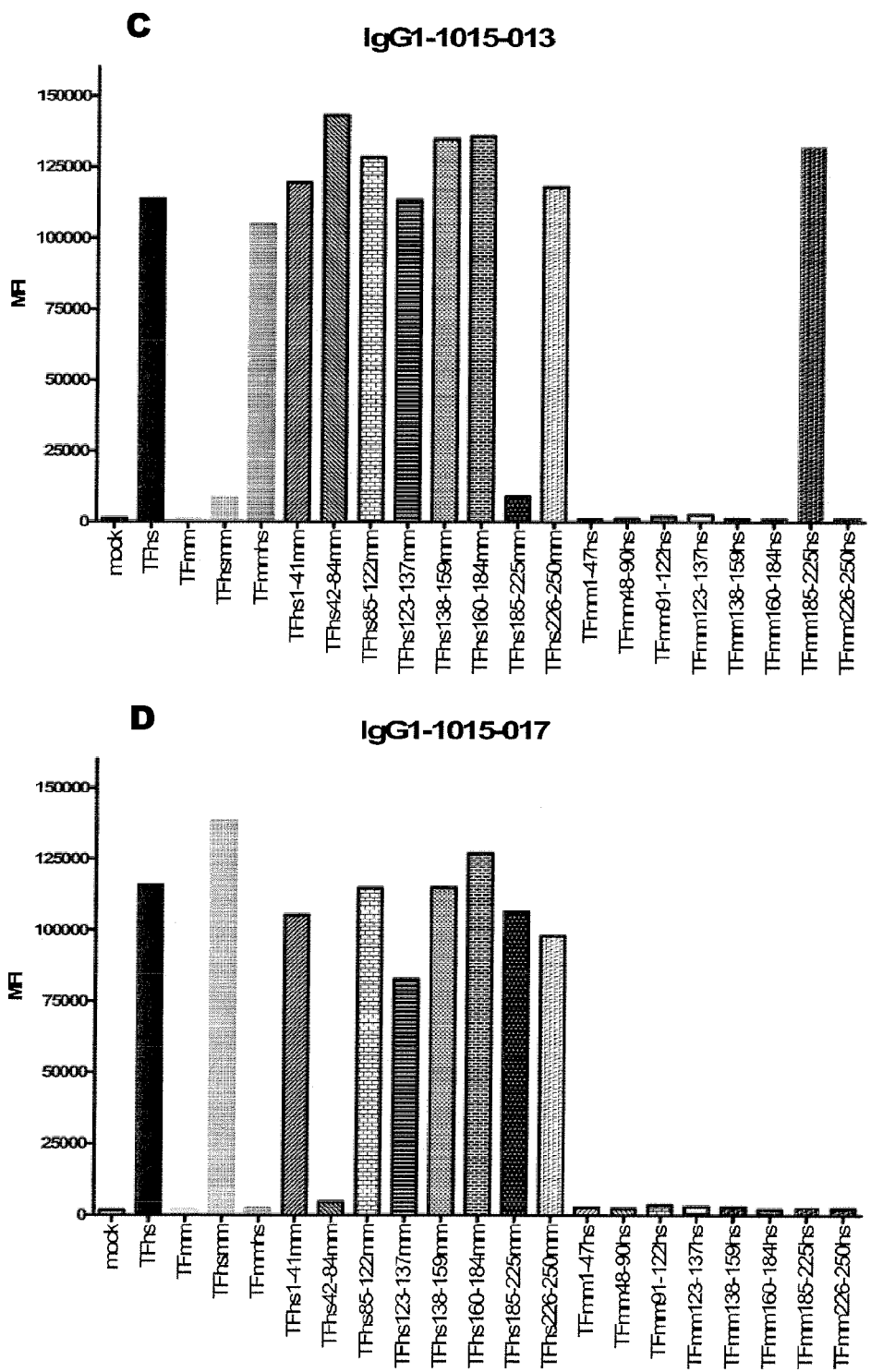

Figure 18 - continued
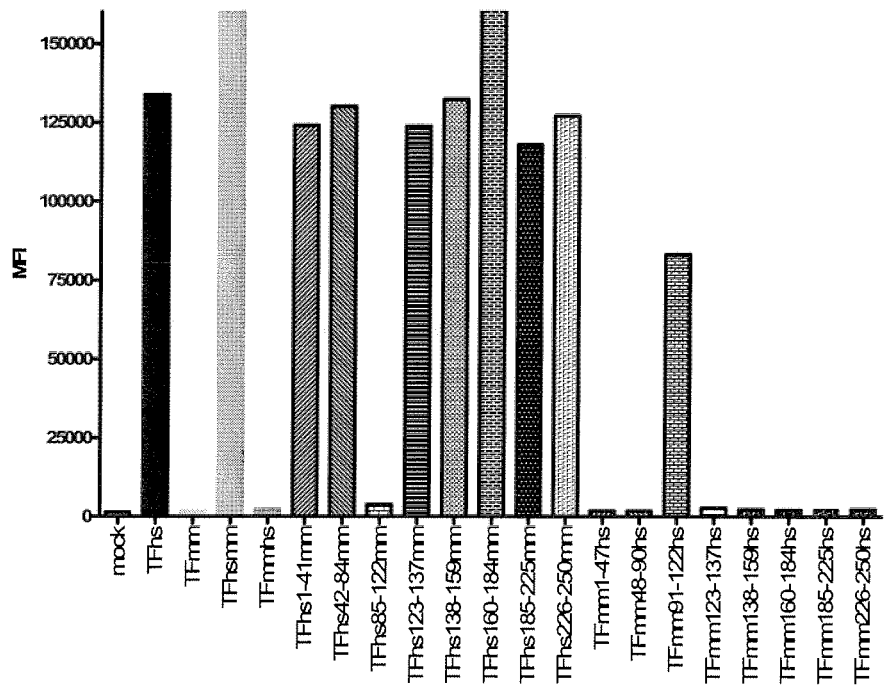
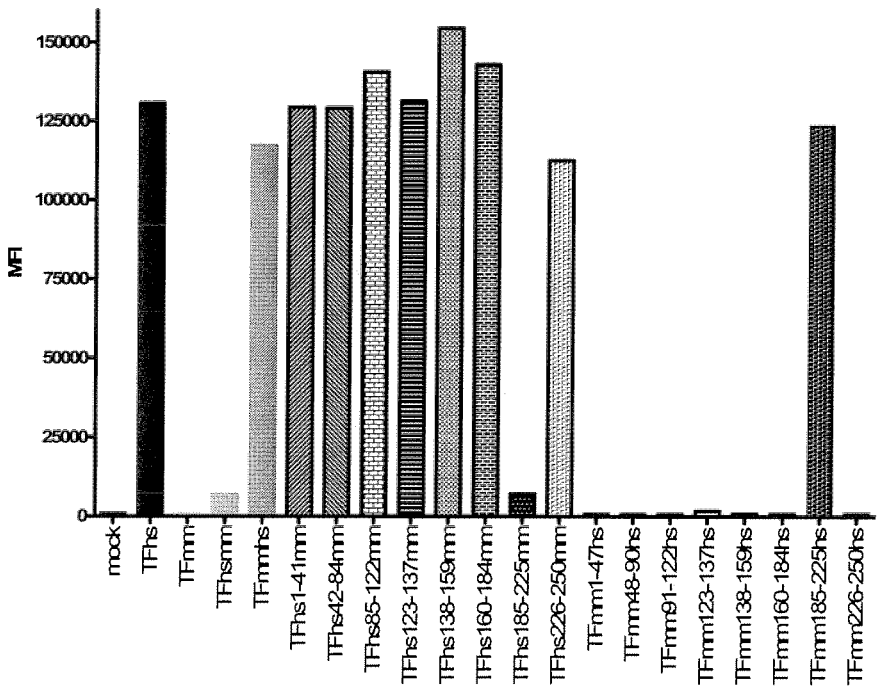

Figure 18 - continued
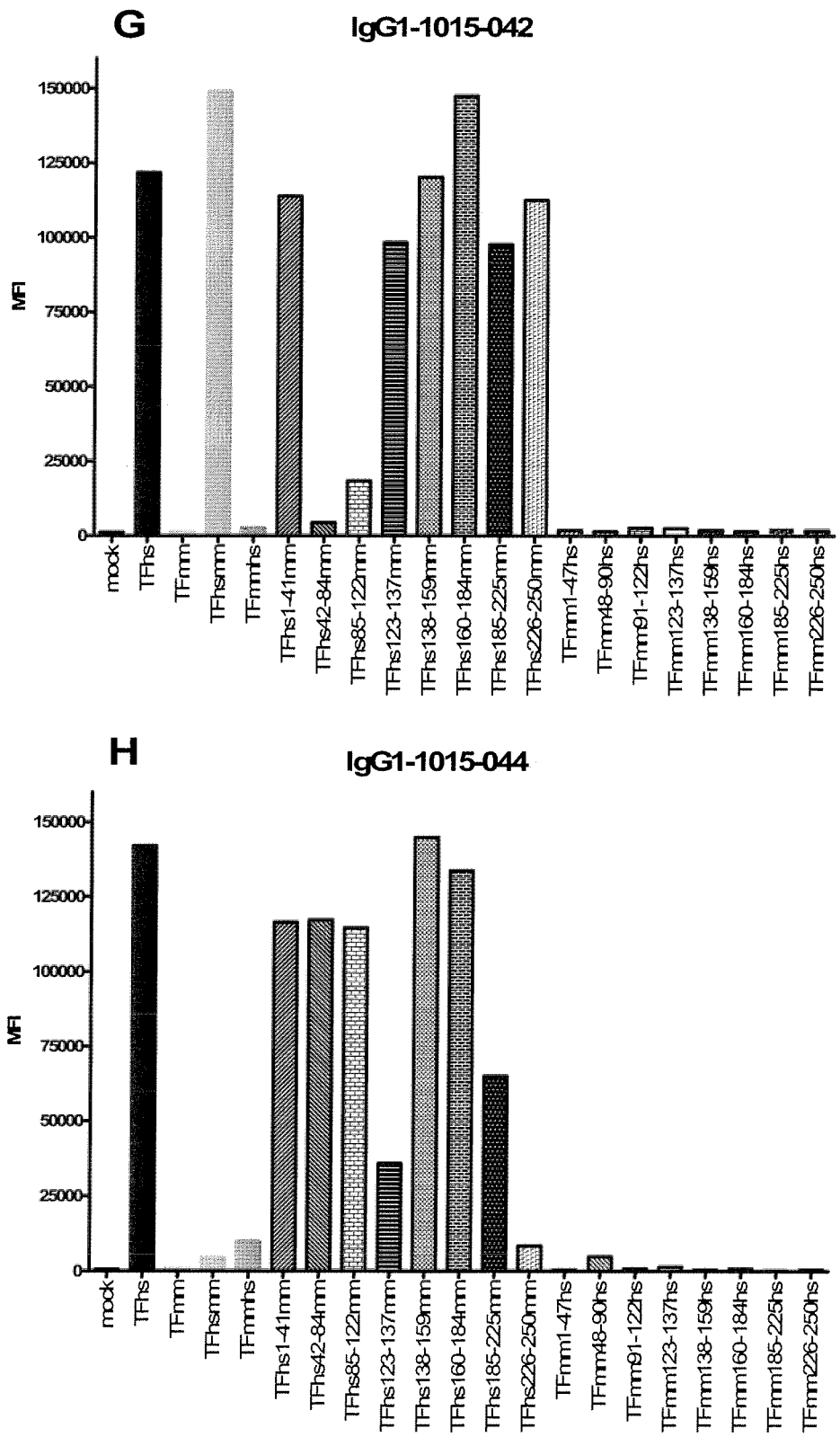

Figure 18 – continued
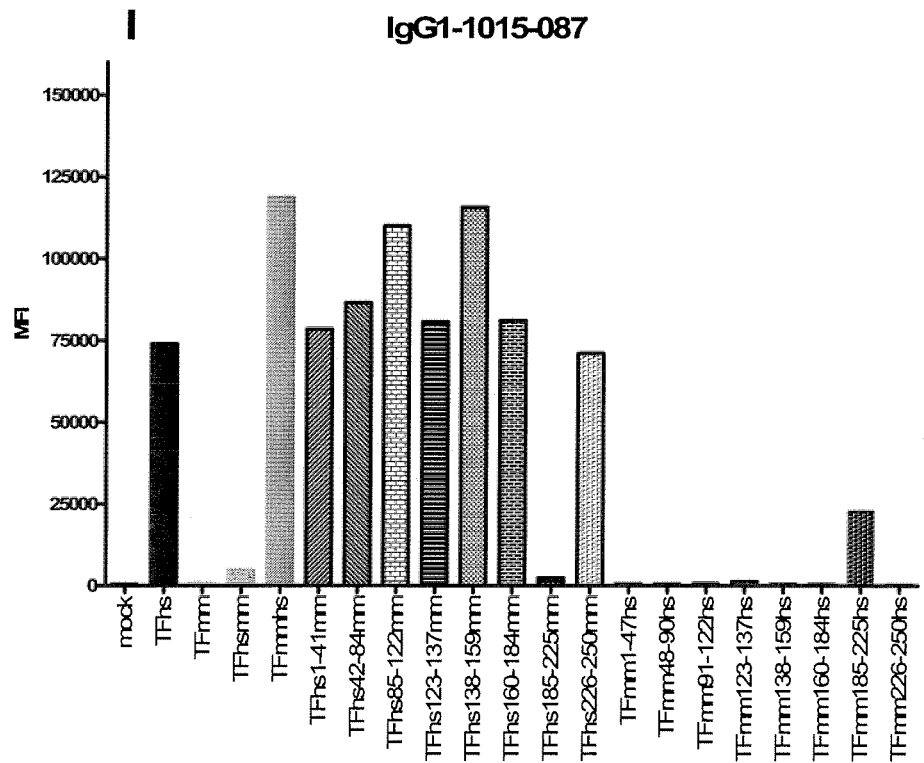
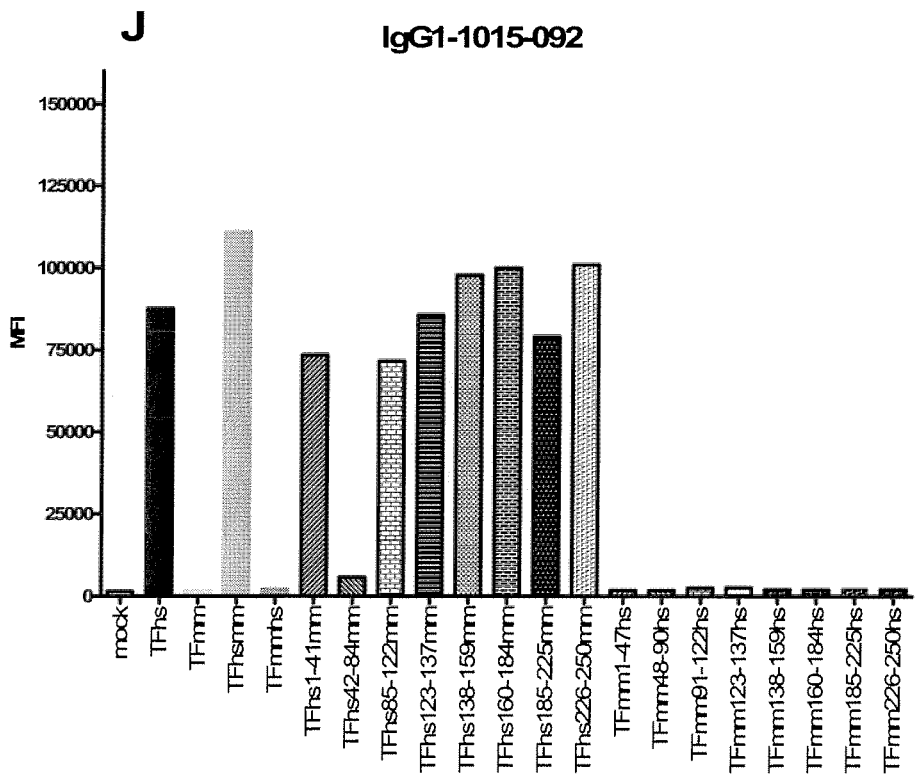

Figure 18 – continued
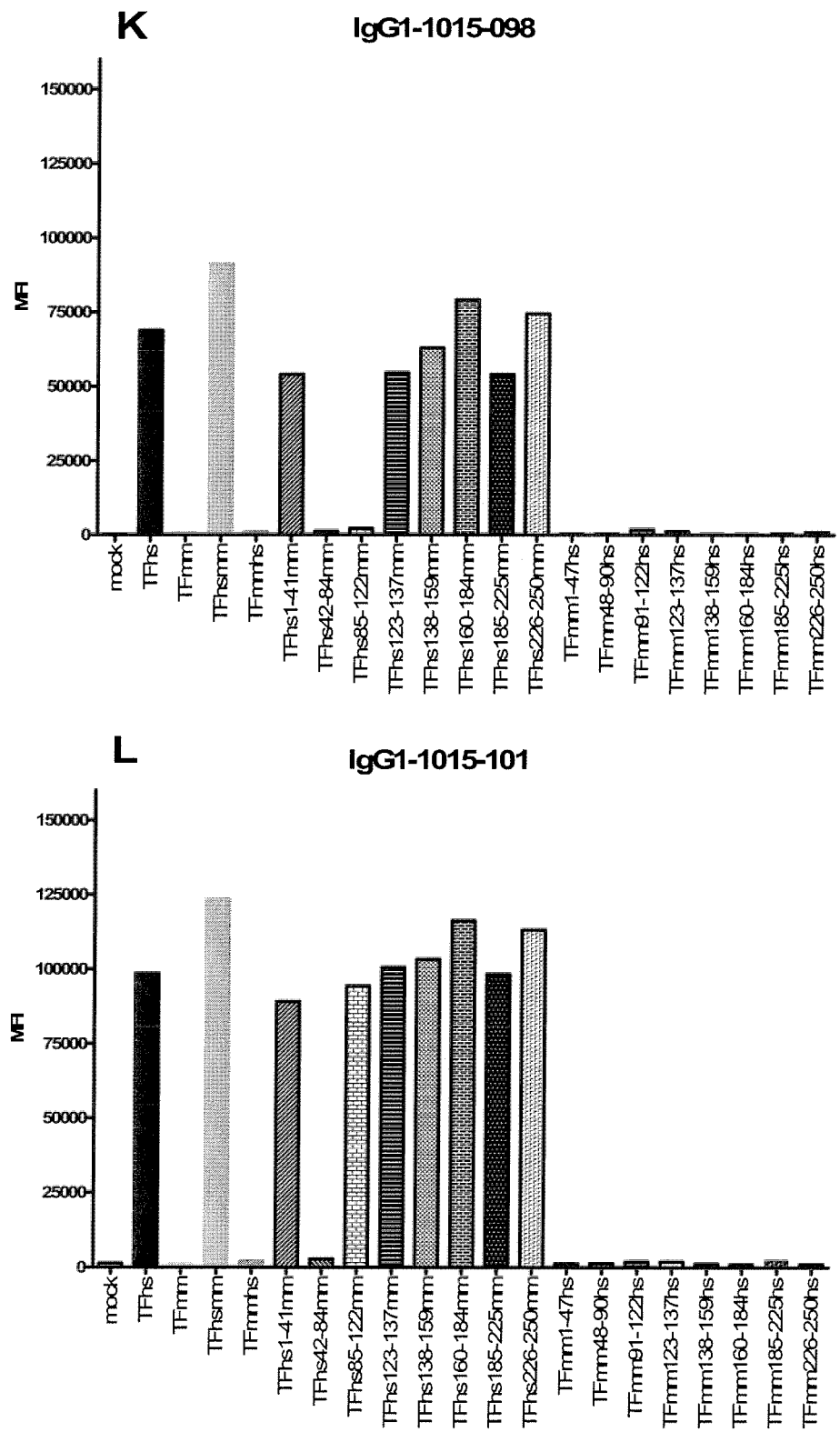

Figure 18 – continued
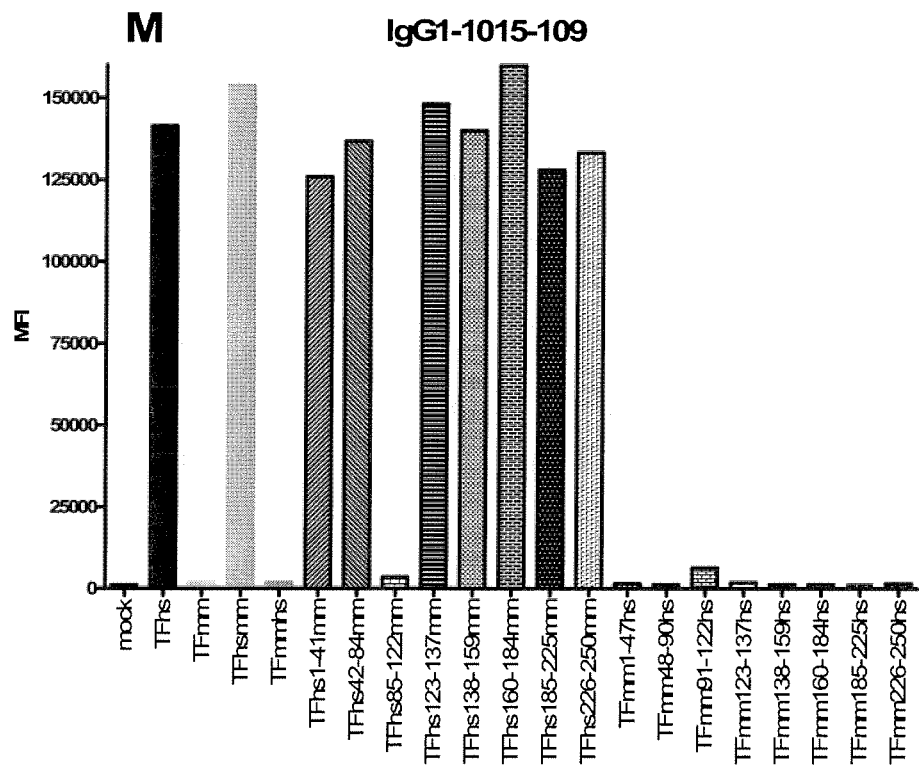
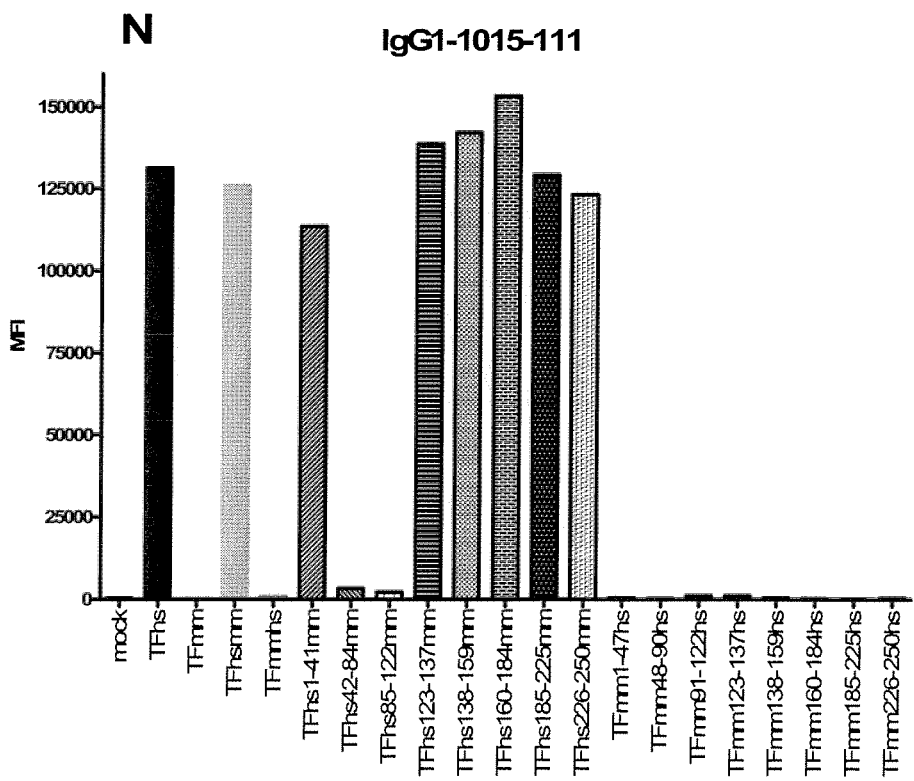

Figure 18 – continued

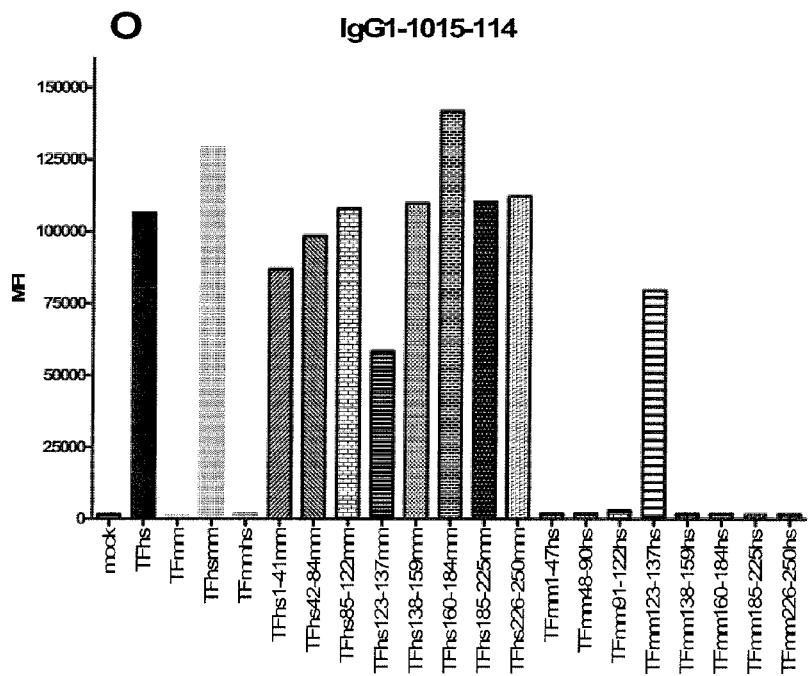

Figure 18 – Binding of anti-TF HuMabs to TF shuffle constructs expressed on HEK293F cells.

Shown are binding profiles of the anti-TF HuMabs to the different TF shuffle constructs expressed on HEK293F cells, as measured by FACS. Each panel shows data from one lead clone. On the x-axis the different constructs are depicted; mock, TFhs, TFmm, TFhsmm, TFmmhs, TFhs1-41mm, TFhs42-84mm, TFhs85-122mm, TFhs123-137mm, TFhs138-159mm, TFhs160-184mm, TFhs185-225mm, TFhs226-250mm, TFmm1-47hs, TFmm48-90hs, TFmm91-122hs, TFmm123-137hs, TFmm138-159hs, TFmm160-184hs, TFmm185-225hs, TFmm226-250hs.

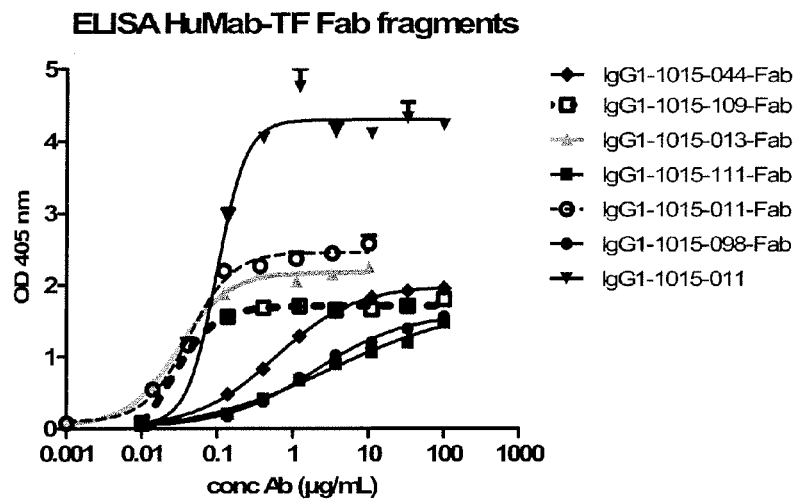
Figure 19. Binding of HuMab-TF Fab fragments to extracellular domain of TF, determined by ELISA.
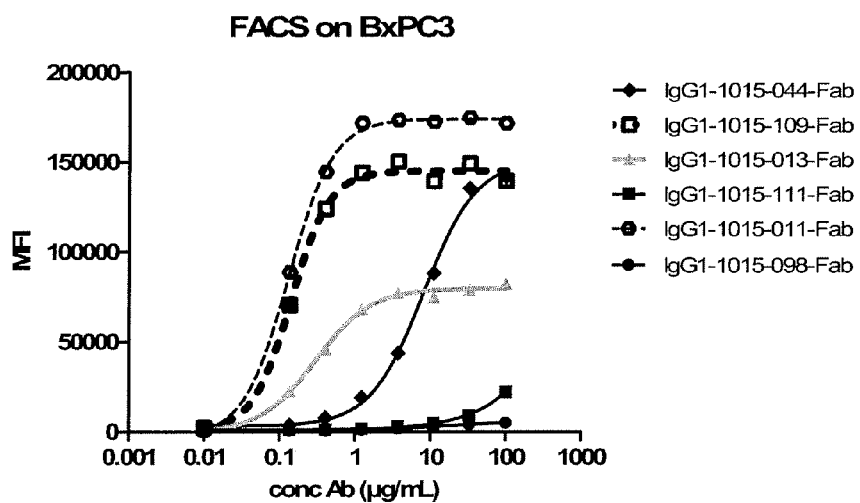
Figure 20. Binding of HuMab-TF Fab fragments to cellular TF, determined by FACS on BxPC3 cells.

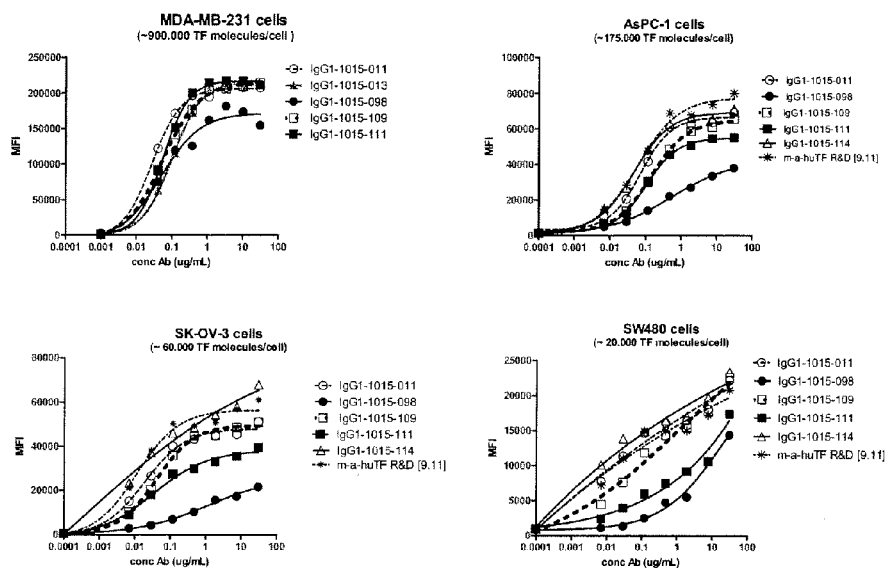
Figure 21. Binding profile of anti-TF HuMabs is dependent on the number of TF molecules expressed.
Binding of anti-TF HuMabs to cell lines expressing different levels of TF was determined by FACS.

SEQUENCE LISTING

```
<160> NUMBER OF SEQ ID NOS: 133

<210> SEQ ID NO 1
<211> LENGTH: 126
<212> TYPE: PRT
<213> ORGANISM: Homo sapiens

<400> SEQUENCE: 1

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
```

```
                    85                  90                  95
Ala Arg Ile His Arg Gly Ala Gly Tyr Ser Ser Ser Trp Pro Gly Ala
                100                 105                 110

Phe Asp Ile Trp Gly Gln Gly Thr Met Val Thr Val Ser Ser
            115                 120                 125

<210> SEQ ID NO 2
<211> LENGTH: 8
<212> TYPE: PRT
<213> ORGANISM: Homo sapiens

<400> SEQUENCE: 2

Gly Tyr Ser Phe Thr Ser Tyr Trp
1               5

<210> SEQ ID NO 3
<211> LENGTH: 8
<212> TYPE: PRT
<213> ORGANISM: Homo sapiens

<400> SEQUENCE: 3

Ile Tyr Pro Gly Asp Ser Asp Thr
1               5

<210> SEQ ID NO 4
<211> LENGTH: 19
<212> TYPE: PRT
<213> ORGANISM: Homo sapiens

<400> SEQUENCE: 4

Ala Arg Ile His Arg Gly Ala Gly Tyr Ser Ser Ser Trp Pro Gly Ala
1               5                   10                  15

Phe Asp Ile

<210> SEQ ID NO 5
<211> LENGTH: 119
<212> TYPE: PRT
<213> ORGANISM: Homo sapiens

<400> SEQUENCE: 5

Gln Val Gln Leu Val Glu Ser Gly Gly Val Val Gln Pro Gly Arg
1               5                   10                  15

Ser Leu Arg Leu Ser Cys Val Ala Ser Gly Phe Thr Val Ser Asn Asp
            20                  25                  30

Gly Met His Trp Val Arg Gln Ala Pro Gly Lys Gly Leu Glu Trp Val
        35                  40                  45

Ala Leu Ile Trp Tyr Asp Gly Val Asn Lys Asn Tyr Ala Asp Ser Val
    50                  55                  60

Lys Gly Arg Phe Thr Ile Ser Arg Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Gly Thr Phe Tyr Gly Leu Asp Val Trp Gly Gln Gly
                100                 105                 110

Thr Thr Val Thr Val Ser Ser
            115

<210> SEQ ID NO 6
<211> LENGTH: 8
<212> TYPE: PRT
```

```
<213> ORGANISM: Homo sapiens

<400> SEQUENCE: 6

Gly Phe Thr Val Ser Asn Asp Gly
1               5

<210> SEQ ID NO 7
<211> LENGTH: 8
<212> TYPE: PRT
<213> ORGANISM: Homo sapiens

<400> SEQUENCE: 7

Ile Trp Tyr Asp Gly Val Asn Lys
1               5

<210> SEQ ID NO 8
<211> LENGTH: 12
<212> TYPE: PRT
<213> ORGANISM: Homo sapiens

<400> SEQUENCE: 8

Ala Arg Arg Pro Gly Thr Phe Tyr Gly Leu Asp Val
1               5                   10

<210> SEQ ID NO 9
<211> LENGTH: 118
<212> TYPE: PRT
<213> ORGANISM: Homo sapiens

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Tyr Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Trp Gly Tyr Tyr Leu Asp Ser Trp Gly Gln Gly Thr
            100                 105                 110

Leu Val Thr Val Ser Ser
        115

<210> SEQ ID NO 10
<211> LENGTH: 8
<212> TYPE: PRT
<213> ORGANISM: Homo sapiens

<400> SEQUENCE: 10

Gly Phe Thr Phe Ser Asn Tyr Ala
1               5

<210> SEQ ID NO 11
<211> LENGTH: 8
<212> TYPE: PRT
<213> ORGANISM: Homo sapiens

<400> SEQUENCE: 11
```

```
Ile Ser Gly Ser Gly Asp Tyr Thr
1               5
```

<210> SEQ ID NO 12
<211> LENGTH: 11
<212> TYPE: PRT
<213> ORGANISM: Homo sapiens

<400> SEQUENCE: 12

```
Ala Arg Ser Pro Trp Gly Tyr Tyr Leu Asp Ser
1               5                   10
```

<210> SEQ ID NO 13
<211> LENGTH: 120
<212> TYPE: PRT
<213> ORGANISM: Homo sapiens

<400> SEQUENCE: 13

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Tyr Phe Leu Leu Trp Tyr Phe Asp Leu Trp Gly Arg
            100                 105                 110

Gly Thr Leu Val Thr Val Ser Ser
        115                 120
```

<210> SEQ ID NO 14
<211> LENGTH: 8
<212> TYPE: PRT
<213> ORGANISM: Homo sapiens

<400> SEQUENCE: 14

```
Gly Phe Thr Phe Ser Ser Tyr Ala
1               5
```

<210> SEQ ID NO 15
<211> LENGTH: 8
<212> TYPE: PRT
<213> ORGANISM: Homo sapiens

<400> SEQUENCE: 15

```
Ile Ser Gly Ser Gly Asp Ser Thr
1               5
```

<210> SEQ ID NO 16
<211> LENGTH: 13
<212> TYPE: PRT
<213> ORGANISM: Homo sapiens

<400> SEQUENCE: 16

```
Ala Lys Asp Gly Tyr Phe Leu Leu Trp Tyr Phe Asp Leu
1               5                   10
```

```
<210> SEQ ID NO 17
<211> LENGTH: 118
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Trp Thr Tyr Tyr Phe Asp Tyr Trp Gly Gln Gly Thr
            100                 105                 110

Leu Val Thr Val Ser Ser
        115

<210> SEQ ID NO 18
<211> LENGTH: 8
<212> TYPE: PRT
<213> ORGANISM: Homo sapiens

<400> SEQUENCE: 18

Gly Phe Thr Phe Ser Ser Tyr Gly
1               5

<210> SEQ ID NO 19
<211> LENGTH: 8
<212> TYPE: PRT
<213> ORGANISM: Homo sapiens

<400> SEQUENCE: 19

Ile Ser Gly Ser Gly Gly Thr Thr
1               5

<210> SEQ ID NO 20
<211> LENGTH: 11
<212> TYPE: PRT
<213> ORGANISM: Homo sapiens

<400> SEQUENCE: 20

Ala Lys Ala Pro Trp Thr Tyr Tyr Phe Asp Tyr
1               5                   10

<210> SEQ ID NO 21
<211> LENGTH: 118
<212> TYPE: PRT
<213> ORGANISM: Homo sapiens

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30
```

```
Ala Met Ser Trp Val Arg Gln Ala Pro Gly Lys Gly Leu Glu Trp Val
            35                  40                  45

Ser Ser Ile Ser Gly Ser Gly Gly Arg Thr Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Lys Thr Pro Trp Gly Tyr Tyr Phe Asp Tyr Trp Gly Gln Gly Thr
            100                 105                 110

Leu Val Thr Val Ser Ser
            115

<210> SEQ ID NO 22
<211> LENGTH: 8
<212> TYPE: PRT
<213> ORGANISM: Homo sapiens

<400> SEQUENCE: 22

Gly Phe Thr Phe Asn Asn Tyr Ala
 1                5

<210> SEQ ID NO 23
<211> LENGTH: 8
<212> TYPE: PRT
<213> ORGANISM: Homo sapiens

<400> SEQUENCE: 23

Ile Ser Gly Ser Gly Gly Arg Thr
 1               5

<210> SEQ ID NO 24
<211> LENGTH: 11
<212> TYPE: PRT
<213> ORGANISM: Homo sapiens

<400> SEQUENCE: 24

Ala Lys Thr Pro Trp Gly Tyr Tyr Phe Asp Tyr
 1               5                   10

<210> SEQ ID NO 25
<211> LENGTH: 118
<212> TYPE: PRT
<213> ORGANISM: Homo sapiens

<400> SEQUENCE: 25

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Ala Lys Gly Leu Asp Trp Val
            35                  40                  45

Ser Gly Ile Ser Gly Ser Gly Val Thr Thr Tyr Tyr Ala Asp Ser Val
 50                  55                  60

Lys Gly Arg Phe Thr Ile Ser Arg Asp Asn Ser Lys Asp Thr Leu Tyr
 65                  70                  75                  80

Leu Gln Met Asn Ser Leu Arg Ala Glu Asp Thr Ala Val Tyr Phe Cys
                 85                  90                  95

Ala Lys Thr Pro Trp Gly Tyr Tyr Phe Asp Tyr Trp Gly Gln Gly Ile
```

Leu Val Ala Val Ser Ser
       115

<210> SEQ ID NO 26
<211> LENGTH: 8
<212> TYPE: PRT
<213> ORGANISM: Homo sapiens

<400> SEQUENCE: 26

Gly Phe Thr Phe Ser Asn Tyr Ala
1               5

<210> SEQ ID NO 27
<211> LENGTH: 8
<212> TYPE: PRT
<213> ORGANISM: Homo sapiens

<400> SEQUENCE: 27

Ile Ser Gly Ser Gly Val Thr Thr
1               5

<210> SEQ ID NO 28
<211> LENGTH: 11
<212> TYPE: PRT
<213> ORGANISM: Homo sapiens

<400> SEQUENCE: 28

Ala Lys Thr Pro Trp Gly Tyr Tyr Phe Asp Tyr
1               5                   10

<210> SEQ ID NO 29
<211> LENGTH: 118
<212> TYPE: PRT
<213> ORGANISM: Homo sapiens

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Pro Arg Gly Thr Phe Ser Tyr Tyr
                20                  25                  30

Thr Ile Ser Trp Val Arg Gln Ala Pro Gly Gln Gly Leu Glu Trp Met
            35                  40                  45

Gly Arg Ile Ile Pro Ile Leu Gly Val Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Asp Arg Arg Tyr Phe Asp Tyr Trp Gly Gln Gly Thr
                100                 105                 110

Leu Val Thr Val Ser Ser
        115

<210> SEQ ID NO 30
<211> LENGTH: 8
<212> TYPE: PRT
<213> ORGANISM: Homo sapiens

<400> SEQUENCE: 30

Arg Gly Thr Phe Ser Tyr Tyr Thr

<210> SEQ ID NO 31
<211> LENGTH: 8
<212> TYPE: PRT
<213> ORGANISM: Homo sapiens

<400> SEQUENCE: 31

Ile Ile Pro Ile Leu Gly Val Ala
1               5

<210> SEQ ID NO 32
<211> LENGTH: 11
<212> TYPE: PRT
<213> ORGANISM: Homo sapiens

<400> SEQUENCE: 32

Ala Arg Glu Gly Asp Arg Arg Tyr Phe Asp Tyr
1               5                   10

<210> SEQ ID NO 33
<211> LENGTH: 120
<212> TYPE: PRT
<213> ORGANISM: Homo sapiens

<400> SEQUENCE: 33

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Arg Tyr
                20                  25                  30

Ala Met His Trp Val Arg Gln Ala Pro Gly Lys Gly Leu Glu Trp Val
            35                  40                  45

Ala Val Ile Ser Asn Asp Gly Tyr Asn Asp Tyr Tyr Ala Asp Ser Val
        50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Leu Gly Arg Gly Tyr Phe Asp Tyr Trp Gly Gln
            100                 105                 110

Gly Thr Leu Val Thr Val Ser Ser
        115                 120

<210> SEQ ID NO 34
<211> LENGTH: 8
<212> TYPE: PRT
<213> ORGANISM: Homo sapiens

<400> SEQUENCE: 34

Gly Phe Thr Phe Ser Arg Tyr Ala
1               5

<210> SEQ ID NO 35
<211> LENGTH: 8
<212> TYPE: PRT
<213> ORGANISM: Homo sapiens

<400> SEQUENCE: 35

Ile Ser Asn Asp Gly Tyr Asn Asp
1               5

<210> SEQ ID NO 36
<211> LENGTH: 13
<212> TYPE: PRT
<213> ORGANISM: Homo sapiens

<400> SEQUENCE: 36

Ala Arg Asp Gly Gln Leu Gly Arg Gly Tyr Phe Asp Tyr
1               5                   10

<210> SEQ ID NO 37
<211> LENGTH: 120
<212> TYPE: PRT
<213> ORGANISM: Homo sapiens

<400> SEQUENCE: 37

Gln Val Gln Leu Val Glu Ser Gly Gly Val Val Gln Pro Gly Arg
1               5                   10                  15

Ser Leu Arg Leu Ser Cys Pro Ala Ser Gly Phe Thr Phe Ser Ile Tyr
                20                  25                  30

Ala Met His Trp Val Arg Gln Ala Pro Gly Lys Gly Leu Glu Trp Val
            35                  40                  45

Ala Val Val Ser Asn Asp Gly Tyr Asn Lys Tyr Tyr Ala Asp Ser Val
        50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Leu Gly Arg Gly Tyr Phe Asp Tyr Trp Gly Gln
            100                 105                 110

Gly Thr Leu Val Thr Val Ser Ser
        115                 120

<210> SEQ ID NO 38
<211> LENGTH: 8
<212> TYPE: PRT
<213> ORGANISM: Homo sapiens

<400> SEQUENCE: 38

Gly Phe Thr Phe Ser Ile Tyr Ala
1               5

<210> SEQ ID NO 39
<211> LENGTH: 8
<212> TYPE: PRT
<213> ORGANISM: Homo sapiens

<400> SEQUENCE: 39

Val Ser Asn Asp Gly Tyr Asn Lys
1               5

<210> SEQ ID NO 40
<211> LENGTH: 13
<212> TYPE: PRT
<213> ORGANISM: Homo sapiens

<400> SEQUENCE: 40

Ala Arg Asp Gly Gln Leu Gly Arg Gly Tyr Phe Asp Tyr
1               5                   10

<210> SEQ ID NO 41
<211> LENGTH: 118
<212> TYPE: PRT

<213> ORGANISM: Homo sapiens

<400> SEQUENCE: 41

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met His Trp Val Arg Gln Ala Pro Gly Lys Gly Leu Glu Trp Val
        35                  40                  45

Ala Val Ile Pro Tyr Asp Gly Asp Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Trp Gly Leu Glu Val Asp Tyr Trp Gly Gln Gly Ala
            100                 105                 110

Leu Val Thr Val Ser Ser
        115

<210> SEQ ID NO 42
<211> LENGTH: 8
<212> TYPE: PRT
<213> ORGANISM: Homo sapiens

<400> SEQUENCE: 42

Gly Phe Thr Phe Ser Asp Tyr Ala
1               5

<210> SEQ ID NO 43
<211> LENGTH: 8
<212> TYPE: PRT
<213> ORGANISM: Homo sapiens

<400> SEQUENCE: 43

Ile Pro Tyr Asp Gly Asp Asn Lys
1               5

<210> SEQ ID NO 44
<211> LENGTH: 11
<212> TYPE: PRT
<213> ORGANISM: Homo sapiens

<400> SEQUENCE: 44

Ala Arg Glu Asp Trp Gly Leu Glu Val Asp Tyr
1               5                   10

<210> SEQ ID NO 45
<211> LENGTH: 121
<212> TYPE: PRT
<213> ORGANISM: Homo sapiens

<400> SEQUENCE: 45

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Cys
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe

```
                50                  55                  60
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Lys Leu Gly Met Asp His Asp Ala Phe Asp Ile Trp Gly
                100                 105                 110

Gln Gly Thr Met Val Thr Val Ser Ser
            115                 120
```

<210> SEQ ID NO 46
<211> LENGTH: 8
<212> TYPE: PRT
<213> ORGANISM: Homo sapiens

<400> SEQUENCE: 46

```
Gly Tyr Ser Phe Thr Ser Cys Trp
 1               5
```

<210> SEQ ID NO 47
<211> LENGTH: 8
<212> TYPE: PRT
<213> ORGANISM: Homo sapiens

<400> SEQUENCE: 47

```
Ile Tyr Pro Gly Asp Ser Asp Thr
 1               5
```

<210> SEQ ID NO 48
<211> LENGTH: 14
<212> TYPE: PRT
<213> ORGANISM: Homo sapiens

<400> SEQUENCE: 48

```
Ala Arg His Lys Leu Gly Met Asp His Asp Ala Phe Asp Ile
 1               5                  10
```

<210> SEQ ID NO 49
<211> LENGTH: 118
<212> TYPE: PRT
<213> ORGANISM: Homo sapiens

<400> SEQUENCE: 49

```
Gln Val Gln Leu Val Gln Ser Gly Ala Glu Val Arg Lys Pro Gly Ser
 1               5                  10                  15

Ser Val Lys Val Ser Cys Lys Ala Ser Gly Gly Ser Phe Asn Asn Tyr
                 20                  25                  30

Pro Ile Phe Trp Val Arg Gln Ala Pro Gly Gln Gly Phe Glu Trp Met
             35                  40                  45

Gly Arg Ile Ile Pro Ile Leu Gly Ile Thr Ala Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Asn Ser Leu Arg Ser Glu Asp Thr Ala Val Tyr Tyr Cys
                 85                  90                  95

Ala Gly Gly Asp Asp Leu Asp Ala Phe Asp Ile Trp Gly Gln Gly Thr
                100                 105                 110

Met Val Ser Val Ser Ser
            115
```

-continued

```
<210> SEQ ID NO 50
<211> LENGTH: 8
<212> TYPE: PRT
<213> ORGANISM: Homo sapiens

<400> SEQUENCE: 50

Gly Gly Ser Phe Asn Asn Tyr Pro
1               5

<210> SEQ ID NO 51
<211> LENGTH: 8
<212> TYPE: PRT
<213> ORGANISM: Homo sapiens

<400> SEQUENCE: 51

Ile Ile Pro Ile Leu Gly Ile Thr
1               5

<210> SEQ ID NO 52
<211> LENGTH: 11
<212> TYPE: PRT
<213> ORGANISM: Homo sapiens

<400> SEQUENCE: 52

Ala Gly Gly Asp Asp Leu Asp Ala Phe Asp Ile
1               5                   10

<210> SEQ ID NO 53
<211> LENGTH: 120
<212> TYPE: PRT
<213> ORGANISM: Homo sapiens

<400> SEQUENCE: 53

Gln Val Gln Leu Val Glu Ser Gly Gly Val Val Gln Pro Gly Arg
1               5                   10                  15

Ser Leu Arg Leu Ser Cys Ala Gly Ser Gly Phe Thr Phe Asn Arg Tyr
            20                  25                  30

Ala Met Tyr Trp Val Arg Gln Ala Pro Gly Lys Gly Leu Asp Trp Val
        35                  40                  45

Ala Val Ile Ser Asn Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Thr Met Val Arg Gly Ala Phe Asp Tyr Trp Gly Gln
            100                 105                 110

Gly Thr Leu Val Thr Val Ser Ser
        115                 120

<210> SEQ ID NO 54
<211> LENGTH: 8
<212> TYPE: PRT
<213> ORGANISM: Homo sapiens

<400> SEQUENCE: 54

Gly Phe Thr Phe Asn Arg Tyr Ala
1               5

<210> SEQ ID NO 55
<211> LENGTH: 8
```

```
<212> TYPE: PRT
<213> ORGANISM: Homo sapiens

<400> SEQUENCE: 55

Ile Ser Asn Asp Gly Ile Asn Lys
1               5

<210> SEQ ID NO 56
<211> LENGTH: 13
<212> TYPE: PRT
<213> ORGANISM: Homo sapiens

<400> SEQUENCE: 56

Ala Arg Asp His Thr Met Val Arg Gly Ala Phe Asp Tyr
1               5                   10

<210> SEQ ID NO 57
<211> LENGTH: 107
<212> TYPE: PRT
<213> ORGANISM: Homo sapiens

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Asp Pro Ile
                85                  90                  95

Thr Phe Gly Gln Gly Thr Arg Leu Glu Ile Lys
            100                 105

<210> SEQ ID NO 58
<211> LENGTH: 6
<212> TYPE: PRT
<213> ORGANISM: Homo sapiens

<400> SEQUENCE: 58

Gln Gly Ile Ser Arg Trp
1               5

<210> SEQ ID NO 59
<211> LENGTH: 3
<212> TYPE: PRT
<213> ORGANISM: Homo sapiens

<400> SEQUENCE: 59

Ala Ala Ser
1

<210> SEQ ID NO 60
<211> LENGTH: 9
<212> TYPE: PRT
<213> ORGANISM: Homo sapiens

<400> SEQUENCE: 60

Gln Gln Tyr Asp Ser Asp Pro Ile Thr
```

```
<210> SEQ ID NO 61
<211> LENGTH: 107
<212> TYPE: PRT
<213> ORGANISM: Homo sapiens

<400> SEQUENCE: 61

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 62
<211> LENGTH: 7
<212> TYPE: PRT
<213> ORGANISM: Homo sapiens

<400> SEQUENCE: 62

Gln Ser Val Ser Ser Ser Tyr
1               5

<210> SEQ ID NO 63
<211> LENGTH: 3
<212> TYPE: PRT
<213> ORGANISM: Homo sapiens

<400> SEQUENCE: 63

Gly Ala Ser
1

<210> SEQ ID NO 64
<211> LENGTH: 8
<212> TYPE: PRT
<213> ORGANISM: Homo sapiens

<400> SEQUENCE: 64

Gln Gln Tyr Gly Ser Ser Leu Thr
1               5

<210> SEQ ID NO 65
<211> LENGTH: 107
<212> TYPE: PRT
<213> ORGANISM: Homo sapiens

<400> SEQUENCE: 65

Asp Ile Gln Met Thr Gln Ser Pro Ser Leu Ser Ala Ser Ala Gly
1               5                   10                  15

Asp Arg Val Thr Ile Thr Cys Arg Ala Ser Gln Gly Ile Ser Ser Arg
            20                  25                  30

Leu Ala Trp Tyr Gln Gln Lys Pro Glu Lys Ala Pro Lys Ser Leu Ile
```

```
            35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro Tyr
                85                  90                  95
Thr Phe Gly Gln Gly Thr Lys Leu Glu Ile Lys
            100                 105
```

<210> SEQ ID NO 66
<211> LENGTH: 6
<212> TYPE: PRT
<213> ORGANISM: Homo sapiens

<400> SEQUENCE: 66

```
Gln Gly Ile Ser Ser Arg
1               5
```

<210> SEQ ID NO 67
<211> LENGTH: 3
<212> TYPE: PRT
<213> ORGANISM: Homo sapiens

<400> SEQUENCE: 67

```
Ala Ala Ser
1
```

<210> SEQ ID NO 68
<211> LENGTH: 9
<212> TYPE: PRT
<213> ORGANISM: Homo sapiens

<400> SEQUENCE: 68

```
Gln Gln Tyr Asn Ser Tyr Pro Tyr Thr
1               5
```

<210> SEQ ID NO 69
<211> LENGTH: 108
<212> TYPE: PRT
<213> ORGANISM: Homo sapiens

<400> SEQUENCE: 69

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Arg Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Arg Thr Phe Gly Gln Gly Thr Lys Val Glu Ile Lys
            100                 105
```

<210> SEQ ID NO 70
<211> LENGTH: 7

```
<212> TYPE: PRT
<213> ORGANISM: Homo sapiens

<400> SEQUENCE: 70

Gln Ser Val Arg Ser Ser Tyr
1               5

<210> SEQ ID NO 71
<211> LENGTH: 3
<212> TYPE: PRT
<213> ORGANISM: Homo sapiens

<400> SEQUENCE: 71

Gly Ala Ser
1

<210> SEQ ID NO 72
<211> LENGTH: 9
<212> TYPE: PRT
<213> ORGANISM: Homo sapiens

<400> SEQUENCE: 72

Gln Gln Tyr Gly Ser Ser Pro Arg Thr
1               5

<210> SEQ ID NO 73
<211> LENGTH: 108
<212> TYPE: PRT
<213> ORGANISM: Homo sapiens

<400> SEQUENCE: 73

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys
            100                 105

<210> SEQ ID NO 74
<211> LENGTH: 7
<212> TYPE: PRT
<213> ORGANISM: Homo sapiens

<400> SEQUENCE: 74

Gln Ser Val Gly Ser Ser Ser
1               5

<210> SEQ ID NO 75
<211> LENGTH: 3
<212> TYPE: PRT
<213> ORGANISM: Homo sapiens

<400> SEQUENCE: 75

Gly Ala Ser
1
```

```
<210> SEQ ID NO 76
<211> LENGTH: 9
<212> TYPE: PRT
<213> ORGANISM: Homo sapiens

<400> SEQUENCE: 76

Gln Gln Tyr Gly Ser Ser Pro Arg Thr
1               5

<210> SEQ ID NO 77
<211> LENGTH: 107
<212> TYPE: PRT
<213> ORGANISM: Homo sapiens

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Arg
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 78
<211> LENGTH: 6
<212> TYPE: PRT
<213> ORGANISM: Homo sapiens

<400> SEQUENCE: 78

Gln Gly Ile Ser Ser Arg
1               5

<210> SEQ ID NO 79
<211> LENGTH: 3
<212> TYPE: PRT
<213> ORGANISM: Homo sapiens

<400> SEQUENCE: 79

Ala Ala Ser
1

<210> SEQ ID NO 80
<211> LENGTH: 9
<212> TYPE: PRT
<213> ORGANISM: Homo sapiens

<400> SEQUENCE: 80

Gln Gln Tyr Asn Ser Tyr Pro Tyr Thr
1               5

<210> SEQ ID NO 81
<211> LENGTH: 108
<212> TYPE: PRT
```

<213> ORGANISM: Homo sapiens

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Tyr Thr Phe Gly Gln Gly Thr Lys Leu Glu Ile Lys
            100                 105

<210> SEQ ID NO 82
<211> LENGTH: 6
<212> TYPE: PRT
<213> ORGANISM: Homo sapiens

<400> SEQUENCE: 82

Gln Gly Ile Ser Ser Trp
1               5

<210> SEQ ID NO 83
<211> LENGTH: 3
<212> TYPE: PRT
<213> ORGANISM: Homo sapiens

<400> SEQUENCE: 83

Ala Ala Ser
1

<210> SEQ ID NO 84
<211> LENGTH: 10
<212> TYPE: PRT
<213> ORGANISM: Homo sapiens

<400> SEQUENCE: 84

Gln Gln Tyr Asn Ser Tyr Pro Leu Tyr Thr
1               5                   10

<210> SEQ ID NO 85
<211> LENGTH: 107
<212> TYPE: PRT
<213> ORGANISM: Homo sapiens

<400> SEQUENCE: 85

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ile Leu Glu Ser Gly Val Pro Ser Arg Phe Ser Gly
50                  55                  60

Ser Gly Ser Gly Thr Asp Phe Thr Leu Thr Ile Ser Ser Leu Gln Pro 65                  70                  75                  80
Glu Asp Phe Ala Thr Tyr Tyr Cys Gln Gln Phe Asn Ser Tyr Pro Leu
                         85                  90                  95

Thr Phe Gly Gly Gly Thr Lys Val Glu Ile Lys
                100                 105

<210> SEQ ID NO 86
<211> LENGTH: 6
<212> TYPE: PRT
<213> ORGANISM: Homo sapiens

<400> SEQUENCE: 86

Gln Asp Ile Ser Ser Ala
1               5

<210> SEQ ID NO 87
<211> LENGTH: 3
<212> TYPE: PRT
<213> ORGANISM: Homo sapiens

<400> SEQUENCE: 87

Asp Ala Ser
1

<210> SEQ ID NO 88
<211> LENGTH: 9
<212> TYPE: PRT
<213> ORGANISM: Homo sapiens

<400> SEQUENCE: 88

Gln Gln Phe Asn Ser Tyr Pro Leu Thr
1               5

<210> SEQ ID NO 89
<211> LENGTH: 107
<212> TYPE: PRT
<213> ORGANISM: Homo sapiens

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                         85                  90                  95

Thr Phe Gly Gly Gly Thr Lys Val Glu Ile Lys
                100                 105

<210> SEQ ID NO 90
<211> LENGTH: 6
<212> TYPE: PRT
<213> ORGANISM: Homo sapiens

<400> SEQUENCE: 90

Gln Ser Val Ser Ser Tyr

```
1               5
```

<210> SEQ ID NO 91
<211> LENGTH: 3
<212> TYPE: PRT
<213> ORGANISM: Homo sapiens

<400> SEQUENCE: 91

```
Asp Ala Ser
1
```

<210> SEQ ID NO 92
<211> LENGTH: 9
<212> TYPE: PRT
<213> ORGANISM: Homo sapiens

<400> SEQUENCE: 92

```
Gln Gln Arg Ser Asn Trp Pro Leu Thr
1               5
```

<210> SEQ ID NO 93
<211> LENGTH: 107
<212> TYPE: PRT
<213> ORGANISM: Homo sapiens

<400> SEQUENCE: 93

```
Glu Ile Val Leu Thr Gln Ser Pro Ala Thr Leu Ser Leu Ser Pro Gly
1               5                   10                  15

Glu Arg Ala Ile Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 94
<211> LENGTH: 6
<212> TYPE: PRT
<213> ORGANISM: Homo sapiens

<400> SEQUENCE: 94

```
Gln Ser Val Ser Ser Tyr
1               5
```

<210> SEQ ID NO 95
<211> LENGTH: 3
<212> TYPE: PRT
<213> ORGANISM: Homo sapiens

<400> SEQUENCE: 95

```
Asp Ala Ser
1
```

<210> SEQ ID NO 96
<211> LENGTH: 9
<212> TYPE: PRT

<213> ORGANISM: Homo sapiens

<400> SEQUENCE: 96

Gln Gln Arg Ser Asn Trp Pro Leu Thr
1               5

<210> SEQ ID NO 97
<211> LENGTH: 107
<212> TYPE: PRT
<213> ORGANISM: Homo sapiens

<400> SEQUENCE: 97

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 98
<211> LENGTH: 6
<212> TYPE: PRT
<213> ORGANISM: Homo sapiens

<400> SEQUENCE: 98

Gln Gly Ile Asn Ser Ala
1               5

<210> SEQ ID NO 99
<211> LENGTH: 3
<212> TYPE: PRT
<213> ORGANISM: Homo sapiens

<400> SEQUENCE: 99

Asp Ala Ser
1

<210> SEQ ID NO 100
<211> LENGTH: 9
<212> TYPE: PRT
<213> ORGANISM: Homo sapiens

<400> SEQUENCE: 100

Gln Gln Phe Asn Ser Tyr Pro Leu Thr
1               5

<210> SEQ ID NO 101
<211> LENGTH: 107
<212> TYPE: PRT
<213> ORGANISM: Homo sapiens

<400> SEQUENCE: 101

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Val Glu Val Lys
            100                 105

<210> SEQ ID NO 102
<211> LENGTH: 6
<212> TYPE: PRT
<213> ORGANISM: Homo sapiens

<400> SEQUENCE: 102

Gln Gly Ile Ser Ser Trp
1               5

<210> SEQ ID NO 103
<211> LENGTH: 3
<212> TYPE: PRT
<213> ORGANISM: Homo sapiens

<400> SEQUENCE: 103

Ala Ala Ser
1

<210> SEQ ID NO 104
<211> LENGTH: 9
<212> TYPE: PRT
<213> ORGANISM: Homo sapiens

<400> SEQUENCE: 104

Gln Gln Tyr Asn Ser Tyr Pro Pro Thr
1               5

<210> SEQ ID NO 105
<211> LENGTH: 107
<212> TYPE: PRT
<213> ORGANISM: Homo sapiens

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
```

<210> SEQ ID NO 106
<211> LENGTH: 6
<212> TYPE: PRT
<213> ORGANISM: Homo sapiens

<400> SEQUENCE: 106

Gln Gly Ile Ser Ser Trp
1               5

<210> SEQ ID NO 107
<211> LENGTH: 3
<212> TYPE: PRT
<213> ORGANISM: Homo sapiens

<400> SEQUENCE: 107

Ala Ala Ser
1

<210> SEQ ID NO 108
<211> LENGTH: 9
<212> TYPE: PRT
<213> ORGANISM: Homo sapiens

<400> SEQUENCE: 108

Gln Gln Tyr Asn Ser Tyr Pro Tyr Thr
1               5

<210> SEQ ID NO 109
<211> LENGTH: 107
<212> TYPE: PRT
<213> ORGANISM: Homo sapiens

<400> SEQUENCE: 109

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
                100                 105

<210> SEQ ID NO 110
<211> LENGTH: 6
<212> TYPE: PRT
<213> ORGANISM: Homo sapiens

<400> SEQUENCE: 110

Gln Ser Val Ser Ser Tyr
1               5

<210> SEQ ID NO 111
<211> LENGTH: 3
<212> TYPE: PRT

<213> ORGANISM: Homo sapiens

<400> SEQUENCE: 111

Asp Ala Ser
1

<210> SEQ ID NO 112
<211> LENGTH: 9
<212> TYPE: PRT
<213> ORGANISM: Homo sapiens

<400> SEQUENCE: 112

Gln Gln Arg Ser Asn Trp Pro Leu Thr
1               5

<210> SEQ ID NO 113
<211> LENGTH: 295
<212> TYPE: PRT
<213> ORGANISM: Artificial Sequence
<220> FEATURE:
<223> OTHER INFORMATION: Synthetic: TFhs/1-295

<400> SEQUENCE: 113

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
                20                  25                  30

Ser Gly Thr Thr Asn Thr Val Ala Ala Tyr Asn Leu Thr Trp Lys Ser
            35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
                100                 105                 110

Gly Asn Val Glu Ser Thr Gly Ser Ala Gly Glu Pro Leu Tyr Glu Asn
            115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
                180                 185                 190

Ser Ser Ser Gly Lys Lys Thr Ala Lys Thr Asn Thr Asn Glu Phe Leu
            195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
                260                 265                 270

```
Ser Leu His Lys Cys Arg Lys Ala Gly Val Gly Gln Ser Trp Lys Glu
            275                 280                 285

Asn Ser Pro Leu Asn Val Ser
        290                 295

<210> SEQ ID NO 114
<211> LENGTH: 289
<212> TYPE: PRT
<213> ORGANISM: Artificial Sequence
<220> FEATURE:
<223> OTHER INFORMATION: Synthetic: Tfhs1-41mm/1-289

<400> SEQUENCE: 114

Met Ala Ile Leu Val Arg Pro Arg Leu Leu Ala Leu Ala Pro Thr
1               5                   10                  15

Phe Leu Gly Cys Leu Leu Leu Gln Val Ile Ala Gly Ala Gly Ile Pro
            20                  25                  30

Glu Lys Ala Phe Asn Leu Thr Trp Ile Ser Thr Asn Phe Lys Thr Ile
            35                  40                  45

Leu Glu Trp Glu Pro Lys Pro Val Asn Gln Val Tyr Thr Val Gln Ile
        50                  55                  60

Ser Thr Lys Ser Gly Asp Trp Lys Ser Lys Cys Phe Tyr Thr Thr Asp
65                  70                  75                  80

Thr Glu Cys Asp Leu Thr Asp Glu Ile Val Lys Asp Val Lys Gln Thr
                85                  90                  95

Tyr Leu Ala Arg Phe Val Ser Tyr Pro Ala Gly Asn Val Glu Ser Thr
            100                 105                 110

Gly Ser Ala Gly Glu Pro Leu Tyr Glu Asn Ser Pro Glu Phe Thr Pro
        115                 120                 125

Tyr Leu Glu Thr Asn Leu Gly Gln Pro Thr Ile Gln Ser Phe Glu Gln
    130                 135                 140

Val Gly Thr Lys Val Asn Val Thr Val Glu Asp Glu Arg Thr Leu Val
145                 150                 155                 160

Arg Arg Asn Asn Thr Phe Leu Ser Leu Arg Asp Val Phe Gly Lys Asp
                165                 170                 175

Leu Ile Tyr Thr Leu Tyr Tyr Trp Lys Ser Ser Ser Ser Gly Lys Lys
            180                 185                 190

Thr Ala Lys Thr Asn Thr Asn Glu Phe Leu Ile Asp Val Asp Lys Gly
        195                 200                 205

Glu Asn Tyr Cys Phe Ser Val Gln Ala Val Ile Pro Ser Arg Thr Val
    210                 215                 220

Asn Arg Lys Ser Thr Asp Ser Pro Val Glu Cys Met Gly Gln Glu Lys
225                 230                 235                 240

Gly Glu Phe Arg Glu Ile Phe Tyr Ile Ile Gly Ala Val Val Phe Val
                245                 250                 255

Val Ile Ile Leu Val Ile Ile Leu Ala Ile Ser Leu His Lys Cys Arg
            260                 265                 270

Lys Ala Gly Val Gly Gln Ser Trp Lys Glu Asn Ser Pro Leu Asn Val
        275                 280                 285

Ser

<210> SEQ ID NO 115
<211> LENGTH: 295
<212> TYPE: PRT
<213> ORGANISM: Artificial Sequence
<220> FEATURE:
<223> OTHER INFORMATION: Synthetic: TFhs42-84mm/1-295
```

<400> SEQUENCE: 115

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asp Phe Lys Thr Ile Leu Glu Trp Gln Pro Lys Pro Thr Asn Tyr
    50                  55                  60

Thr Tyr Thr Val Gln Ile Ser Asp Arg Ser Arg Asn Trp Lys Asn Lys
65                  70                  75                  80

Cys Phe Ser Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
            260                 265                 270

Ser Leu His Lys Cys Arg Lys Ala Gly Val Gly Gln Ser Trp Lys Glu
        275                 280                 285

Asn Ser Pro Leu Asn Val Ser
    290                 295

<210> SEQ ID NO 116
<211> LENGTH: 301
<212> TYPE: PRT
<213> ORGANISM: Artificial Sequence
<220> FEATURE:
<223> OTHER INFORMATION: Synthetic: TFhs85-122mm/1-301

<400> SEQUENCE: 116

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

```
Thr Asn Phe Lys Thr Ile Leu Glu Trp Glu Pro Lys Pro Val Asn Gln
 50                  55                  60

Val Tyr Thr Val Gln Ile Ser Thr Lys Ser Gly Asp Trp Lys Ser Lys
 65                  70                  75                  80

Cys Phe Tyr Thr Thr Asp Thr Glu Cys Asp Leu Thr Asp Glu Ile Val
                 85                  90                  95

Lys Asp Val Thr Trp Ala Tyr Glu Ala Lys Val Leu Ser Val Pro Arg
            100                 105                 110

Arg Asn Ser Val His Gly Asp Gly Asp Gln Leu Val Ile His Gly Glu
            115                 120                 125

Glu Pro Leu Tyr Glu Asn Ser Pro Glu Phe Thr Pro Tyr Leu Glu Thr
130                 135                 140

Asn Leu Gly Gln Pro Thr Ile Gln Ser Phe Glu Gln Val Gly Thr Lys
145                 150                 155                 160

Val Asn Val Thr Val Glu Asp Glu Arg Thr Leu Val Arg Arg Asn Asn
                165                 170                 175

Thr Phe Leu Ser Leu Arg Asp Val Phe Gly Lys Asp Leu Ile Tyr Thr
            180                 185                 190

Leu Tyr Tyr Trp Lys Ser Ser Ser Gly Lys Lys Thr Ala Lys Thr
            195                 200                 205

Asn Thr Asn Glu Phe Leu Ile Asp Val Asp Lys Gly Glu Asn Tyr Cys
210                 215                 220

Phe Ser Val Gln Ala Val Ile Pro Ser Arg Thr Val Asn Arg Lys Ser
225                 230                 235                 240

Thr Asp Ser Pro Val Glu Cys Met Gly Gln Glu Lys Gly Glu Phe Arg
                245                 250                 255

Glu Ile Phe Tyr Ile Ile Gly Ala Val Val Phe Val Val Ile Ile Leu
            260                 265                 270

Val Ile Ile Leu Ala Ile Ser Leu His Lys Cys Arg Lys Ala Gly Val
            275                 280                 285

Gly Gln Ser Trp Lys Glu Asn Ser Pro Leu Asn Val Ser
290                 295                 300

<210> SEQ ID NO 117
<211> LENGTH: 295
<212> TYPE: PRT
<213> ORGANISM: Artificial Sequence
<220> FEATURE:
<223> OTHER INFORMATION: Synthetic: TFhs123-137mm/1-295

<400> SEQUENCE: 117

Met Glu Thr Pro Ala Trp Pro Arg Val Pro Arg Pro Glu Thr Ala Val
 1               5                  10                  15

Ala Arg Thr Leu Leu Leu Gly Trp Val Phe Ala Gln Val Ala Gly Ala
             20                  25                  30

Ser Gly Thr Thr Asn Thr Val Ala Ala Tyr Asn Leu Thr Trp Lys Ser
             35                  40                  45

Thr Asn Phe Lys Thr Ile Leu Glu Trp Glu Pro Lys Pro Val Asn Gln
 50                  55                  60

Val Tyr Thr Val Gln Ile Ser Thr Lys Ser Gly Asp Trp Lys Ser Lys
 65                  70                  75                  80

Cys Phe Tyr Thr Thr Asp Thr Glu Cys Asp Leu Thr Asp Glu Ile Val
                 85                  90                  95

Lys Asp Val Lys Gln Thr Tyr Leu Ala Arg Val Phe Ser Tyr Pro Ala
            100                 105                 110
```

```
Gly Asn Val Glu Ser Thr Gly Ser Ala Gly Glu Pro Pro Phe Thr Asn
            115                 120                 125

Ala Pro Lys Phe Leu Pro Tyr Arg Asp Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
    195                 200                 205

Ile Asp Val Asp Lys Gly Glu Asn Tyr Cys Phe Ser Val Gln Ala Val
210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
            245                 250                 255

Gly Ala Val Val Phe Val Val Ile Ile Leu Val Ile Ile Leu Ala Ile
                260                 265                 270

Ser Leu His Lys Cys Arg Lys Ala Gly Val Gly Gln Ser Trp Lys Glu
            275                 280                 285

Asn Ser Pro Leu Asn Val Ser
            290                 295

<210> SEQ ID NO 118
<211> LENGTH: 295
<212> TYPE: PRT
<213> ORGANISM: Artificial Sequence
<220> FEATURE:
<223> OTHER INFORMATION: Synthetic: TFhs138-159mm/1-295

<400> SEQUENCE: 118

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
            115                 120                 125

Ser Pro Glu Phe Thr Pro Tyr Leu Glu Thr Asn Leu Gly Gln Pro Val
    130                 135                 140

Ile Gln Gln Phe Glu Gln Asp Gly Arg Lys Leu Asn Val Val Val Glu
145                 150                 155                 160

Asp Glu Arg Thr Leu Val Arg Arg Asn Asn Thr Phe Leu Ser Leu Arg
                165                 170                 175
```

```
Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
                260                 265                 270

Ser Leu His Lys Cys Arg Lys Ala Gly Val Gly Gln Ser Trp Lys Glu
            275                 280                 285

Asn Ser Pro Leu Asn Val Ser
            290                 295

<210> SEQ ID NO 119
<211> LENGTH: 295
<212> TYPE: PRT
<213> ORGANISM: Artificial Sequence
<220> FEATURE:
<223> OTHER INFORMATION: Synthetic: TFhs160-184mm/1-295

<400> SEQUENCE: 119

Met Glu Thr Pro Ala Trp Pro Arg Val Pro Arg Pro Glu Thr Ala Val
1               5                   10                  15

Ala Arg Thr Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Lys
145                 150                 155                 160

Asp Ser Leu Thr Leu Val Arg Lys Asn Gly Thr Phe Leu Thr Leu Arg
                165                 170                 175

Gln Val Phe Gly Lys Asp Leu Gly Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240
```

```
Cys Met Gly Gln Glu Lys Gly Glu Phe Arg Glu Ile Phe Tyr Ile Ile
            245                 250                 255

Gly Ala Val Val Phe Val Val Ile Ile Leu Val Ile Ile Leu Ala Ile
        260                 265                 270

Ser Leu His Lys Cys Arg Lys Ala Gly Val Gly Gln Ser Trp Lys Glu
        275                 280                 285

Asn Ser Pro Leu Asn Val Ser
        290                 295

<210> SEQ ID NO 120
<211> LENGTH: 295
<212> TYPE: PRT
<213> ORGANISM: Artificial Sequence
<220> FEATURE:
<223> OTHER INFORMATION: Synthetic: TFhs185-225mm/1-295

<400> SEQUENCE: 120

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Ile Ile Thr Tyr Arg Lys Gly
            180                 185                 190

Ser Ser Thr Gly Lys Lys Thr Asn Ile Thr Asn Thr Asn Glu Phe Ser
        195                 200                 205

Ile Asp Val Glu Glu Gly Val Ser Tyr Cys Phe Phe Val Gln Ala Met
210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
            260                 265                 270

Ser Leu His Lys Cys Arg Lys Ala Gly Val Gly Gln Ser Trp Lys Glu
        275                 280                 285

Asn Ser Pro Leu Asn Val Ser
        290                 295
```

<210> SEQ ID NO 121
<211> LENGTH: 295
<212> TYPE: PRT
<213> ORGANISM: Artificial Sequence
<220> FEATURE:
<223> OTHER INFORMATION: Synthetic: TFhs226-250mm/1-295

<400> SEQUENCE: 121

```
Met Glu Thr Pro Ala Trp Pro Arg Val Pro Arg Pro Glu Thr Ala Val
1               5                   10                  15

Ala Arg Thr Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
            35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
                100                 105                 110

Gly Asn Val Glu Ser Thr Gly Ser Ala Gly Glu Pro Leu Tyr Glu Asn
            115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
                180                 185                 190

Ser Ser Ser Gly Lys Lys Thr Ala Lys Thr Asn Thr Asn Glu Phe Leu
            195                 200                 205

Ile Asp Val Asp Lys Gly Glu Asn Tyr Cys Phe Ser Val Gln Ala Val
    210                 215                 220

Ile Phe Ser Arg Lys Thr Asn Gln Asn Ser Pro Gly Ser Ser Thr Val
225                 230                 235                 240

Cys Thr Glu Gln Trp Lys Ser Phe Leu Gly Glu Ile Phe Tyr Ile Ile
                245                 250                 255

Gly Ala Val Val Phe Val Val Ile Ile Leu Val Ile Ile Leu Ala Ile
                260                 265                 270

Ser Leu His Lys Cys Arg Lys Ala Gly Val Gly Gln Ser Trp Lys Glu
            275                 280                 285

Asn Ser Pro Leu Asn Val Ser
    290                 295
```

<210> SEQ ID NO 122
<211> LENGTH: 294
<212> TYPE: PRT
<213> ORGANISM: Artificial Sequence
<220> FEATURE:
<223> OTHER INFORMATION: Synthetic: TFhsmm/1-294

<400> SEQUENCE: 122

```
Met Glu Thr Pro Ala Trp Pro Arg Val Pro Arg Pro Glu Thr Ala Val
1               5                   10                  15
```

Ala Arg Thr Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
 50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Val
130                 135                 140

Ile Gln Gln Phe Glu Gln Asp Gly Arg Lys Leu Asn Val Val Val Lys
145                 150                 155                 160

Asp Ser Leu Thr Leu Val Arg Lys Asn Gly Thr Phe Leu Thr Leu Arg
                165                 170                 175

Gln Val Phe Gly Lys Asp Leu Gly Tyr Ile Ile Thr Tyr Arg Lys Gly
            180                 185                 190

Ser Ser Thr Gly Lys Lys Thr Asn Ile Thr Asn Thr Asn Glu Phe Ser
        195                 200                 205

Ile Asp Val Glu Glu Gly Val Ser Tyr Cys Phe Phe Val Gln Ala Met
210                 215                 220

Ile Phe Ser Arg Lys Thr Asn Gln Asn Ser Pro Gly Ser Ser Thr Val
225                 230                 235                 240

Cys Thr Glu Gln Trp Lys Ser Phe Leu Gly Glu Thr Leu Ile Ile Val
                245                 250                 255

Gly Ala Val Val Leu Leu Ala Thr Ile Phe Ile Ile Leu Leu Ser Ile
            260                 265                 270

Ser Leu Cys Lys Arg Arg Lys Asn Arg Ala Gly Gln Lys Gly Lys Asn
        275                 280                 285

Thr Pro Ser Arg Leu Ala
    290

<210> SEQ ID NO 123
<211> LENGTH: 294
<212> TYPE: PRT
<213> ORGANISM: Artificial Sequence
<220> FEATURE:
<223> OTHER INFORMATION: Synthetic: TFmm/1-294

<400> SEQUENCE: 123

Met Ala Ile Leu Val Arg Pro Arg Leu Leu Ala Ala Leu Ala Pro Thr
1               5                   10                  15

Phe Leu Gly Cys Leu Leu Gln Val Ile Ala Gly Ala Gly Ile Pro
            20                  25                  30

Glu Lys Ala Phe Asn Leu Thr Trp Ile Ser Thr Asp Phe Lys Thr Ile
        35                  40                  45

Leu Glu Trp Gln Pro Lys Pro Thr Asn Tyr Thr Tyr Thr Val Gln Ile
    50                  55                  60

Ser Asp Arg Ser Arg Asn Trp Lys Asn Lys Cys Phe Ser Thr Thr Asp
65                  70                  75                  80

```
Thr Glu Cys Asp Leu Thr Asp Glu Ile Val Lys Asp Val Thr Trp Ala
                85                  90                  95

Tyr Glu Ala Lys Val Leu Ser Val Pro Arg Arg Asn Ser Val His Gly
                100                 105                 110

Asp Gly Asp Gln Leu Val Ile His Gly Glu Pro Pro Phe Thr Asn
            115                 120                 125

Ala Pro Lys Phe Leu Pro Tyr Arg Asp Thr Asn Leu Gly Gln Pro Val
        130                 135                 140

Ile Gln Gln Phe Glu Gln Asp Gly Arg Lys Leu Asn Val Val Lys
145                 150                 155                 160

Asp Ser Leu Thr Leu Val Arg Lys Asn Gly Thr Phe Leu Thr Leu Arg
                165                 170                 175

Gln Val Phe Gly Lys Asp Leu Gly Tyr Ile Ile Thr Tyr Arg Lys Gly
                180                 185                 190

Ser Ser Thr Gly Lys Lys Thr Asn Ile Thr Asn Thr Asn Glu Phe Ser
                195                 200                 205

Ile Asp Val Glu Glu Gly Val Ser Tyr Cys Phe Phe Val Gln Ala Met
            210                 215                 220

Ile Phe Ser Arg Lys Thr Asn Gln Asn Ser Pro Gly Ser Ser Thr Val
225                 230                 235                 240

Cys Thr Glu Gln Trp Lys Ser Phe Leu Gly Glu Thr Leu Ile Ile Val
                245                 250                 255

Gly Ala Val Val Leu Leu Ala Thr Ile Phe Ile Ile Leu Leu Ser Ile
                260                 265                 270

Ser Leu Cys Lys Arg Arg Lys Asn Arg Ala Gly Gln Lys Gly Lys Asn
                275                 280                 285

Thr Pro Ser Arg Leu Ala
                290

<210> SEQ ID NO 124
<211> LENGTH: 295
<212> TYPE: PRT
<213> ORGANISM: Artificial Sequence
<220> FEATURE:
<223> OTHER INFORMATION: Synthetic: TFmmhs/1-295

<400> SEQUENCE: 124

Met Ala Ile Leu Val Arg Pro Arg Leu Leu Ala Ala Leu Ala Pro Thr
1               5                   10                  15

Phe Leu Gly Cys Leu Leu Leu Gln Val Ile Ala Gly Ala Gly Ile Pro
                20                  25                  30

Glu Lys Ala Phe Asn Leu Thr Trp Ile Ser Thr Asp Phe Lys Thr Ile
            35                  40                  45

Leu Glu Trp Gln Pro Lys Pro Thr Asn Tyr Thr Tyr Thr Val Gln Ile
        50                  55                  60

Ser Asp Arg Ser Arg Asn Trp Lys Asn Lys Cys Phe Ser Thr Thr Asp
65                  70                  75                  80

Thr Glu Cys Asp Leu Thr Asp Glu Ile Val Lys Asp Val Thr Trp Ala
                85                  90                  95

Tyr Glu Ala Lys Val Leu Ser Val Pro Arg Arg Asn Ser Val His Gly
                100                 105                 110

Asp Gly Asp Gln Leu Val Ile His Gly Glu Pro Pro Phe Thr Asn
            115                 120                 125

Ala Pro Lys Phe Leu Pro Tyr Arg Asp Thr Asn Leu Gly Gln Pro Thr
        130                 135                 140
```

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
            260                 265                 270

Ser Leu His Lys Cys Arg Lys Ala Gly Val Gly Gln Ser Trp Lys Glu
        275                 280                 285

Asn Ser Pro Leu Asn Val Ser
    290                 295

<210> SEQ ID NO 125
<211> LENGTH: 300
<212> TYPE: PRT
<213> ORGANISM: Artificial Sequence
<220> FEATURE:
<223> OTHER INFORMATION: Synthetic: TFmm1-47hs/1-300

<400> SEQUENCE: 125

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Gln Pro Lys Pro Thr Asn Tyr
50                  55                  60

Thr Tyr Thr Val Gln Ile Ser Asp Arg Ser Arg Asn Trp Lys Asn Lys
65                  70                  75                  80

Cys Phe Ser Thr Thr Asp Thr Glu Cys Asp Leu Thr Asp Glu Ile Val
                85                  90                  95

Lys Asp Val Thr Trp Ala Tyr Glu Ala Lys Val Leu Ser Val Pro Arg
            100                 105                 110

Arg Asn Ser Val His Gly Asp Gly Asp Gln Leu Val Ile His Gly Glu
        115                 120                 125

Glu Pro Pro Phe Thr Asn Ala Pro Lys Phe Leu Pro Tyr Arg Asp Thr
130                 135                 140

Asn Leu Gly Gln Pro Val Ile Gln Gln Phe Glu Gln Asp Gly Arg Lys
145                 150                 155                 160

Leu Asn Val Val Val Lys Asp Ser Leu Thr Leu Val Arg Lys Asn Gly
                165                 170                 175

Thr Phe Leu Thr Leu Arg Gln Val Phe Gly Lys Asp Leu Gly Tyr Ile
            180                 185                 190

Ile Thr Tyr Arg Lys Gly Ser Ser Thr Gly Lys Lys Thr Asn Ile Thr
        195                 200                 205

```
Asn Thr Asn Glu Phe Ser Ile Asp Val Glu Glu Gly Val Ser Tyr Cys
    210                 215                 220

Phe Phe Val Gln Ala Met Ile Phe Ser Arg Lys Thr Asn Gln Asn Ser
225                 230                 235                 240

Pro Gly Ser Ser Thr Val Cys Thr Glu Gln Trp Lys Ser Phe Leu Gly
                245                 250                 255

Glu Thr Leu Ile Ile Val Gly Ala Val Leu Leu Ala Thr Ile Phe
                260                 265                 270

Ile Ile Leu Leu Ser Ile Ser Leu Cys Lys Arg Arg Lys Asn Arg Ala
                275                 280                 285

Gly Gln Lys Gly Lys Asn Thr Pro Ser Arg Leu Ala
    290                 295                 300

<210> SEQ ID NO 126
<211> LENGTH: 294
<212> TYPE: PRT
<213> ORGANISM: Artificial Sequence
<220> FEATURE:
<223> OTHER INFORMATION: Synthetic: TFmm48-90hs/1-294

<400> SEQUENCE: 126

Met Ala Ile Leu Val Arg Pro Arg Leu Leu Ala Ala Leu Ala Pro Thr
1               5                   10                  15

Phe Leu Gly Cys Leu Leu Gln Val Ile Ala Gly Ala Gly Ile Pro
                20                  25                  30

Glu Lys Ala Phe Asn Leu Thr Trp Ile Ser Thr Asn Phe Lys Thr Ile
                35                  40                  45

Leu Glu Trp Glu Pro Lys Pro Val Asn Gln Val Tyr Thr Val Gln Ile
50                  55                  60

Ser Thr Lys Ser Gly Asp Trp Lys Ser Lys Cys Phe Tyr Thr Thr Asp
65                  70                  75                  80

Thr Glu Cys Asp Leu Thr Asp Glu Ile Val Lys Asp Val Thr Trp Ala
                85                  90                  95

Tyr Glu Ala Lys Val Leu Ser Val Pro Arg Arg Asn Ser Val His Gly
                100                 105                 110

Asp Gly Asp Gln Leu Val Ile His Gly Glu Pro Pro Phe Thr Asn
    115                 120                 125

Ala Pro Lys Phe Leu Pro Tyr Arg Asp Thr Asn Leu Gly Gln Pro Val
    130                 135                 140

Ile Gln Gln Phe Glu Gln Asp Gly Arg Lys Leu Asn Val Val Lys
145                 150                 155                 160

Asp Ser Leu Thr Leu Val Arg Lys Asn Gly Thr Phe Leu Thr Leu Arg
                165                 170                 175

Gln Val Phe Gly Lys Asp Leu Gly Tyr Ile Ile Thr Tyr Arg Lys Gly
                180                 185                 190

Ser Ser Thr Gly Lys Lys Thr Asn Ile Thr Asn Thr Asn Glu Phe Ser
                195                 200                 205

Ile Asp Val Glu Glu Gly Val Ser Tyr Cys Phe Phe Val Gln Ala Met
    210                 215                 220

Ile Phe Ser Arg Lys Thr Asn Gln Asn Ser Pro Gly Ser Ser Thr Val
225                 230                 235                 240

Cys Thr Glu Gln Trp Lys Ser Phe Leu Gly Glu Thr Leu Ile Ile Val
                245                 250                 255

Gly Ala Val Val Leu Leu Ala Thr Ile Phe Ile Ile Leu Leu Ser Ile
                260                 265                 270
```

Ser Leu Cys Lys Arg Arg Lys Asn Arg Ala Gly Gln Lys Gly Lys Asn
            275                 280                 285

Thr Pro Ser Arg Leu Ala
    290

<210> SEQ ID NO 127
<211> LENGTH: 288
<212> TYPE: PRT
<213> ORGANISM: Artificial Sequence
<220> FEATURE:
<223> OTHER INFORMATION: Synthetic: TFmm91-122hs/1-288

<400> SEQUENCE: 127

Met Ala Ile Leu Val Arg Pro Arg Leu Leu Ala Ala Leu Ala Pro Thr
1               5                   10                  15

Phe Leu Gly Cys Leu Leu Leu Gln Val Ile Ala Gly Ala Gly Ile Pro
            20                  25                  30

Glu Lys Ala Phe Asn Leu Thr Trp Ile Ser Thr Asp Phe Lys Thr Ile
        35                  40                  45

Leu Glu Trp Gln Pro Lys Pro Thr Asn Tyr Thr Tyr Thr Val Gln Ile
    50                  55                  60

Ser Asp Arg Ser Arg Asn Trp Lys Asn Lys Cys Phe Ser Thr Thr Asp
65                  70                  75                  80

Thr Glu Cys Asp Leu Thr Asp Glu Ile Val Lys Asp Val Lys Gln Thr
                85                  90                  95

Tyr Leu Ala Arg Val Phe Ser Tyr Pro Ala Gly Asn Val Glu Ser Thr
            100                 105                 110

Gly Ser Ala Gly Glu Pro Pro Phe Thr Asn Ala Pro Lys Phe Leu Pro
        115                 120                 125

Tyr Arg Asp Thr Asn Leu Gly Gln Pro Val Ile Gln Gln Phe Glu Gln
    130                 135                 140

Asp Gly Arg Lys Leu Asn Val Val Lys Asp Ser Leu Thr Leu Val
145                 150                 155                 160

Arg Lys Asn Gly Thr Phe Leu Thr Leu Arg Gln Val Phe Gly Lys Asp
                165                 170                 175

Leu Gly Tyr Ile Ile Thr Tyr Arg Lys Gly Ser Ser Thr Gly Lys Lys
            180                 185                 190

Thr Asn Ile Thr Asn Thr Asn Glu Phe Ser Ile Asp Val Glu Glu Gly
        195                 200                 205

Val Ser Tyr Cys Phe Phe Val Gln Ala Met Ile Phe Ser Arg Lys Thr
    210                 215                 220

Asn Gln Asn Ser Pro Gly Ser Ser Thr Val Cys Thr Glu Gln Trp Lys
225                 230                 235                 240

Ser Phe Leu Gly Glu Thr Leu Ile Ile Val Gly Ala Val Val Leu Leu
                245                 250                 255

Ala Thr Ile Phe Ile Ile Leu Leu Ser Ile Ser Leu Cys Lys Arg Arg
            260                 265                 270

Lys Asn Arg Ala Gly Gln Lys Gly Lys Asn Thr Pro Ser Arg Leu Ala
        275                 280                 285

<210> SEQ ID NO 128
<211> LENGTH: 294
<212> TYPE: PRT
<213> ORGANISM: Artificial Sequence
<220> FEATURE:
<223> OTHER INFORMATION: Synthetic: TFmm123-137hs/1-294

<400> SEQUENCE: 128

| Met | Ala | Ile | Leu | Val | Arg | Pro | Arg | Leu | Leu | Ala | Ala | Leu | Ala | Pro | Thr |
|---|---|---|---|---|---|---|---|---|---|---|---|---|---|---|---|
| 1 | | | | 5 | | | | | 10 | | | | | 15 | |

| Phe | Leu | Gly | Cys | Leu | Leu | Leu | Gln | Val | Ile | Ala | Gly | Ala | Gly | Ile | Pro |
|---|---|---|---|---|---|---|---|---|---|---|---|---|---|---|---|
| | | | 20 | | | | | 25 | | | | | 30 | | |

| Glu | Lys | Ala | Phe | Asn | Leu | Thr | Trp | Ile | Ser | Thr | Asp | Phe | Lys | Thr | Ile |
|---|---|---|---|---|---|---|---|---|---|---|---|---|---|---|---|
| | | 35 | | | | | 40 | | | | | 45 | | | |

| Leu | Glu | Trp | Gln | Pro | Lys | Pro | Thr | Asn | Tyr | Thr | Tyr | Thr | Val | Gln | Ile |
|---|---|---|---|---|---|---|---|---|---|---|---|---|---|---|---|
| | 50 | | | | | 55 | | | | | 60 | | | | |

| Ser | Asp | Arg | Ser | Arg | Asn | Trp | Lys | Asn | Lys | Cys | Phe | Ser | Thr | Thr | Asp |
|---|---|---|---|---|---|---|---|---|---|---|---|---|---|---|---|
| 65 | | | | | 70 | | | | | 75 | | | | | 80 |

| Thr | Glu | Cys | Asp | Leu | Thr | Asp | Glu | Ile | Val | Lys | Asp | Val | Thr | Trp | Ala |
|---|---|---|---|---|---|---|---|---|---|---|---|---|---|---|---|
| | | | | 85 | | | | | 90 | | | | | 95 | |

| Tyr | Glu | Ala | Lys | Val | Leu | Ser | Val | Pro | Arg | Arg | Asn | Ser | Val | His | Gly |
|---|---|---|---|---|---|---|---|---|---|---|---|---|---|---|---|
| | | | 100 | | | | | 105 | | | | | 110 | | |

| Asp | Gly | Asp | Gln | Leu | Val | Ile | His | Gly | Glu | Glu | Pro | Leu | Tyr | Glu | Asn |
|---|---|---|---|---|---|---|---|---|---|---|---|---|---|---|---|
| | | 115 | | | | | 120 | | | | | 125 | | | |

| Ser | Pro | Glu | Phe | Thr | Pro | Tyr | Leu | Glu | Thr | Asn | Leu | Gly | Gln | Pro | Val |
|---|---|---|---|---|---|---|---|---|---|---|---|---|---|---|---|
| | 130 | | | | | 135 | | | | | 140 | | | | |

| Ile | Gln | Gln | Phe | Glu | Gln | Asp | Gly | Arg | Lys | Leu | Asn | Val | Val | Lys |
|---|---|---|---|---|---|---|---|---|---|---|---|---|---|---|
| 145 | | | | | 150 | | | | | 155 | | | | 160 |

| Asp | Ser | Leu | Thr | Leu | Val | Arg | Lys | Asn | Gly | Thr | Phe | Leu | Thr | Leu | Arg |
|---|---|---|---|---|---|---|---|---|---|---|---|---|---|---|---|
| | | | | 165 | | | | | 170 | | | | | 175 | |

| Gln | Val | Phe | Gly | Lys | Asp | Leu | Gly | Tyr | Ile | Ile | Thr | Tyr | Arg | Lys | Gly |
|---|---|---|---|---|---|---|---|---|---|---|---|---|---|---|---|
| | | | 180 | | | | | 185 | | | | | 190 | | |

| Ser | Ser | Thr | Gly | Lys | Lys | Thr | Asn | Ile | Thr | Asn | Thr | Asn | Glu | Phe | Ser |
|---|---|---|---|---|---|---|---|---|---|---|---|---|---|---|---|
| | | 195 | | | | | 200 | | | | | 205 | | | |

| Ile | Asp | Val | Glu | Glu | Gly | Val | Ser | Tyr | Cys | Phe | Phe | Val | Gln | Ala | Met |
|---|---|---|---|---|---|---|---|---|---|---|---|---|---|---|---|
| 210 | | | | | 215 | | | | | 220 | | | | | |

| Ile | Phe | Ser | Arg | Lys | Thr | Asn | Gln | Asn | Ser | Pro | Gly | Ser | Ser | Thr | Val |
|---|---|---|---|---|---|---|---|---|---|---|---|---|---|---|---|
| 225 | | | | | 230 | | | | | 235 | | | | | 240 |

| Cys | Thr | Glu | Gln | Trp | Lys | Ser | Phe | Leu | Gly | Glu | Thr | Leu | Ile | Ile | Val |
|---|---|---|---|---|---|---|---|---|---|---|---|---|---|---|---|
| | | | | 245 | | | | | 250 | | | | | 255 | |

| Gly | Ala | Val | Val | Leu | Leu | Ala | Thr | Ile | Phe | Ile | Ile | Leu | Leu | Ser | Ile |
|---|---|---|---|---|---|---|---|---|---|---|---|---|---|---|---|
| | | | 260 | | | | | 265 | | | | | 270 | | |

| Ser | Leu | Cys | Lys | Arg | Arg | Lys | Asn | Arg | Ala | Gln | Lys | Gly | Lys | Asn |
|---|---|---|---|---|---|---|---|---|---|---|---|---|---|---|
| | | 275 | | | | | 280 | | | | | 285 | | |

| Thr | Pro | Ser | Arg | Leu | Ala |
|---|---|---|---|---|---|
| | | 290 | | | |

<210> SEQ ID NO 129
<211> LENGTH: 294
<212> TYPE: PRT
<213> ORGANISM: Artificial Sequence
<220> FEATURE:
<223> OTHER INFORMATION: Synthetic: TFmm138-159hs/1-294

<400> SEQUENCE: 129

| Met | Ala | Ile | Leu | Val | Arg | Pro | Arg | Leu | Leu | Ala | Ala | Leu | Ala | Pro | Thr |
|---|---|---|---|---|---|---|---|---|---|---|---|---|---|---|---|
| 1 | | | | 5 | | | | | 10 | | | | | 15 | |

| Phe | Leu | Gly | Cys | Leu | Leu | Leu | Gln | Val | Ile | Ala | Gly | Ala | Gly | Ile | Pro |
|---|---|---|---|---|---|---|---|---|---|---|---|---|---|---|---|
| | | | 20 | | | | | 25 | | | | | 30 | | |

| Glu | Lys | Ala | Phe | Asn | Leu | Thr | Trp | Ile | Ser | Thr | Asp | Phe | Lys | Thr | Ile |
|---|---|---|---|---|---|---|---|---|---|---|---|---|---|---|---|
| | | 35 | | | | | 40 | | | | | 45 | | | |

| Leu | Glu | Trp | Gln | Pro | Lys | Pro | Thr | Asn | Tyr | Thr | Tyr | Thr | Val | Gln | Ile |

```
            50                  55                  60
Ser Asp Arg Ser Arg Asn Trp Lys Asn Lys Cys Phe Ser Thr Thr Asp
 65                  70                  75                  80

Thr Glu Cys Asp Leu Thr Asp Glu Ile Val Lys Asp Val Thr Trp Ala
                 85                  90                  95

Tyr Glu Ala Lys Val Leu Ser Val Pro Arg Arg Asn Ser Val His Gly
                100                 105                 110

Asp Gly Asp Gln Leu Val Ile His Gly Glu Glu Pro Pro Phe Thr Asn
            115                 120                 125

Ala Pro Lys Phe Leu Pro Tyr Arg Asp Thr Asn Leu Gly Gln Pro Thr
        130                 135                 140

Ile Gln Ser Phe Glu Gln Val Gly Thr Lys Val Asn Val Thr Val Lys
145                 150                 155                 160

Asp Ser Leu Thr Leu Val Arg Lys Asn Gly Thr Phe Leu Thr Leu Arg
                165                 170                 175

Gln Val Phe Gly Lys Asp Leu Gly Tyr Ile Ile Thr Tyr Arg Lys Gly
                180                 185                 190

Ser Ser Thr Gly Lys Lys Thr Asn Ile Thr Asn Thr Asn Glu Phe Ser
            195                 200                 205

Ile Asp Val Glu Glu Gly Val Ser Tyr Cys Phe Phe Val Gln Ala Met
        210                 215                 220

Ile Phe Ser Arg Lys Thr Asn Gln Asn Ser Pro Gly Ser Ser Thr Val
225                 230                 235                 240

Cys Thr Glu Gln Trp Lys Ser Phe Leu Gly Glu Thr Leu Ile Ile Val
                245                 250                 255

Gly Ala Val Val Leu Leu Ala Thr Ile Phe Ile Ile Leu Leu Ser Ile
                260                 265                 270

Ser Leu Cys Lys Arg Arg Lys Asn Arg Ala Gly Gln Lys Gly Lys Asn
            275                 280                 285

Thr Pro Ser Arg Leu Ala
        290

<210> SEQ ID NO 130
<211> LENGTH: 294
<212> TYPE: PRT
<213> ORGANISM: Artificial Sequence
<220> FEATURE:
<223> OTHER INFORMATION: Synthetic: TFmm160-184hs/1-294

<400> SEQUENCE: 130

Met Ala Ile Leu Val Arg Pro Arg Leu Leu Ala Ala Leu Ala Pro Thr
  1               5                  10                  15

Phe Leu Gly Cys Leu Leu Leu Gln Val Ile Ala Gly Ala Gly Ile Pro
                 20                  25                  30

Glu Lys Ala Phe Asn Leu Thr Trp Ile Ser Thr Asp Phe Lys Thr Ile
             35                  40                  45

Leu Glu Trp Gln Pro Lys Pro Thr Asn Tyr Thr Tyr Thr Val Gln Ile
         50                  55                  60

Ser Asp Arg Ser Arg Asn Trp Lys Asn Lys Cys Phe Ser Thr Thr Asp
 65                  70                  75                  80

Thr Glu Cys Asp Leu Thr Asp Glu Ile Val Lys Asp Val Thr Trp Ala
                 85                  90                  95

Tyr Glu Ala Lys Val Leu Ser Val Pro Arg Arg Asn Ser Val His Gly
                100                 105                 110

Asp Gly Asp Gln Leu Val Ile His Gly Glu Glu Pro Pro Phe Thr Asn
```

-continued

```
            115                 120                 125
Ala Pro Lys Phe Leu Pro Tyr Arg Asp Thr Asn Leu Gly Gln Pro Val
    130                 135                 140
Ile Gln Gln Phe Glu Gln Asp Gly Arg Lys Leu Asn Val Val Glu
145                 150                 155                 160
Asp Glu Arg Thr Leu Val Arg Arg Asn Thr Phe Leu Ser Leu Arg
                165                 170                 175
Asp Val Phe Gly Lys Asp Leu Ile Tyr Ile Thr Tyr Arg Lys Gly
                180                 185                 190
Ser Ser Thr Gly Lys Lys Thr Asn Ile Thr Asn Thr Asn Glu Phe Ser
                195                 200                 205
Ile Asp Val Glu Glu Gly Val Ser Tyr Cys Phe Val Gln Ala Met
    210                 215                 220
Ile Phe Ser Arg Lys Thr Asn Gln Asn Ser Pro Gly Ser Ser Thr Val
225                 230                 235                 240
Cys Thr Glu Gln Trp Lys Ser Phe Leu Gly Glu Thr Leu Ile Ile Val
                245                 250                 255
Gly Ala Val Val Leu Leu Ala Thr Ile Phe Ile Ile Leu Leu Ser Ile
                260                 265                 270
Ser Leu Cys Lys Arg Arg Lys Asn Arg Ala Gly Gln Lys Gly Lys Asn
                275                 280                 285
Thr Pro Ser Arg Leu Ala
    290

<210> SEQ ID NO 131
<211> LENGTH: 294
<212> TYPE: PRT
<213> ORGANISM: Artificial Sequence
<220> FEATURE:
<223> OTHER INFORMATION: Synthetic: TFmm185-225hs/1-294

<400> SEQUENCE: 131

Met Ala Ile Leu Val Arg Pro Arg Leu Leu Ala Ala Leu Ala Pro Thr
1               5                   10                  15
Phe Leu Gly Cys Leu Leu Leu Gln Val Ile Ala Gly Ala Gly Ile Pro
                20                  25                  30
Glu Lys Ala Phe Asn Leu Thr Trp Ile Ser Thr Asp Phe Lys Thr Ile
            35                  40                  45
Leu Glu Trp Gln Pro Lys Pro Thr Asn Tyr Thr Tyr Thr Val Gln Ile
        50                  55                  60
Ser Asp Arg Ser Arg Asn Trp Lys Asn Lys Cys Phe Ser Thr Thr Asp
65                  70                  75                  80
Thr Glu Cys Asp Leu Thr Asp Glu Ile Val Lys Asp Val Thr Trp Ala
                85                  90                  95
Tyr Glu Ala Lys Val Leu Ser Val Pro Arg Arg Asn Ser Val His Gly
            100                 105                 110
Asp Gly Asp Gln Leu Val Ile His Gly Glu Glu Pro Pro Phe Thr Asn
        115                 120                 125
Ala Pro Lys Phe Leu Pro Tyr Arg Asp Thr Asn Leu Gly Gln Pro Val
    130                 135                 140
Ile Gln Gln Phe Glu Gln Asp Gly Arg Lys Leu Asn Val Val Lys
145                 150                 155                 160
Asp Ser Leu Thr Leu Val Arg Lys Asn Gly Thr Phe Leu Thr Leu Arg
                165                 170                 175
Gln Val Phe Gly Lys Asp Leu Gly Tyr Thr Leu Tyr Tyr Trp Lys Ser
```

```
                180                 185                 190
Ser Ser Ser Gly Lys Lys Thr Ala Lys Thr Asn Thr Asn Glu Phe Leu
            195                 200                 205

Ile Asp Val Asp Lys Gly Glu Asn Tyr Cys Phe Ser Val Gln Ala Val
        210                 215                 220

Ile Phe Ser Arg Lys Thr Asn Gln Asn Ser Pro Gly Ser Ser Thr Val
225                 230                 235                 240

Cys Thr Glu Gln Trp Lys Ser Phe Leu Gly Glu Thr Leu Ile Ile Val
            245                 250                 255

Gly Ala Val Val Leu Leu Ala Thr Ile Phe Ile Ile Leu Leu Ser Ile
        260                 265                 270

Ser Leu Cys Lys Arg Arg Lys Asn Arg Ala Gly Gln Lys Gly Lys Asn
            275                 280                 285

Thr Pro Ser Arg Leu Ala
        290

<210> SEQ ID NO 132
<211> LENGTH: 294
<212> TYPE: PRT
<213> ORGANISM: Artificial Sequence
<220> FEATURE:
<223> OTHER INFORMATION: Synthetic: TFmm226-250hs/1-294

<400> SEQUENCE: 132

Met Ala Ile Leu Val Arg Pro Arg Leu Leu Ala Ala Leu Ala Pro Thr
1               5                   10                  15

Phe Leu Gly Cys Leu Leu Leu Gln Val Ile Ala Gly Ala Gly Ile Pro
            20                  25                  30

Glu Lys Ala Phe Asn Leu Thr Trp Ile Ser Thr Asp Phe Lys Thr Ile
        35                  40                  45

Leu Glu Trp Gln Pro Lys Pro Thr Asn Tyr Thr Tyr Thr Val Gln Ile
50                  55                  60

Ser Asp Arg Ser Arg Asn Trp Lys Asn Lys Cys Phe Ser Thr Thr Asp
65                  70                  75                  80

Thr Glu Cys Asp Leu Thr Asp Glu Ile Val Lys Asp Val Thr Trp Ala
            85                  90                  95

Tyr Glu Ala Lys Val Leu Ser Val Pro Arg Arg Asn Ser Val His Gly
        100                 105                 110

Asp Gly Asp Gln Leu Val Ile His Gly Glu Pro Pro Phe Thr Asn
        115                 120                 125

Ala Pro Lys Phe Leu Pro Tyr Arg Asp Thr Asn Leu Gly Gln Pro Val
        130                 135                 140

Ile Gln Gln Phe Glu Gln Asp Gly Arg Lys Leu Asn Val Val Lys
145                 150                 155                 160

Asp Ser Leu Thr Leu Val Arg Lys Asn Gly Thr Phe Leu Thr Leu Arg
                165                 170                 175

Gln Val Phe Gly Lys Asp Leu Gly Tyr Ile Ile Thr Tyr Arg Lys Gly
            180                 185                 190

Ser Ser Thr Gly Lys Lys Thr Asn Ile Thr Asn Thr Asn Glu Phe Ser
        195                 200                 205

Ile Asp Val Glu Glu Gly Val Ser Tyr Cys Phe Val Gln Ala Met
        210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Thr Leu Ile Ile Val
```

```
                      245                 250                 255
Gly Ala Val Val Leu Leu Ala Thr Ile Phe Ile Ile Leu Leu Ser Ile
            260                 265                 270

Ser Leu Cys Lys Arg Arg Lys Asn Arg Ala Gly Gln Lys Gly Lys Asn
        275                 280                 285

Thr Pro Ser Arg Leu Ala
    290

<210> SEQ ID NO 133
<211> LENGTH: 4
<212> TYPE: PRT
<213> ORGANISM: Artificial Sequence
<220> FEATURE:
<223> OTHER INFORMATION: Synthetic

<400> SEQUENCE: 133

Cys Pro Pro Cys
1
```

HUMAN ANTIBODIES AGAINST TISSUE FACTOR AND METHODS OF USE THEREOF

This application is a 35 U.S.C. 371 national stage filing of International Application No. PCT/EP2009/066755 filed Dec. 9, 2009 (International Publication No. WO 2010/066803), which claims priority to Danish Patent Application No. PA 2008 01744 filed on Dec. 9, 2008, and U.S. Provisional Application No. 61/201,335 filed on Dec. 9, 2008. The contents of the aforementioned applications are hereby incorporated by reference.

FIELD OF THE INVENTION

The present invention relates to antibodies directed to tissue factor in particular to human tissue factor, and uses of such antibodies, in particular their use in the treatment of cancer, inflammation and vascular diseases.

BACKGROUND OF THE INVENTION

Tissue factor (TF), also called thromboplastin, factor III or CD142 is a protein present in subendothelial tissue, platelets, and leukocytes necessary for the initiation of thrombin formation from the zymogen prothrombin. Thrombin formation ultimately leads to the coagulation of blood. Tissue factor enables cells to initiate the blood coagulation cascades, and it functions as the high-affinity receptor for the coagulation factor VII. The resulting complex provides a catalytic event that is responsible for initiation of the coagulation protease cascades by specific limited proteolysis. Unlike the other cofactors of these protease cascades, which circulate as non-functional precursors, this factor is a potent initiator that is fully functional when expressed on cell surfaces.

Tissue factor is the cell surface receptor for the serine protease factor VIIa (FVIIa). Binding of FVIIa to tissue factor has been found to start signaling processes inside the cell said signaling function playing a role in angiogenesis. Whereas angiogenesis is a normal process in growth and development, as well as in wound healing it is also a fundamental step in the transition of tumors from a dormant state to a malignant state: when cancer cells gain the ability to produce proteins that participate in angiogenesis, so called angiogenic growth factors, these proteins are released by the tumor into nearby tissues, and stimulate new blood vessels to sprout from existing healthy blood vessels toward and into the tumor. Once new blood vessels enter the tumor it can rapidly expand its size and invade local tissue and organs. Through the new blood vessels cancer cells may further escape into the circulation and lodge in other organs to form new tumors (metastases).

Further TF plays a role in inflammation. The role of TF is assumed to be mediated by blood coagulation (A. J. Chu: "Tissue factor mediates inflammation" in Archives of biochemistry and biophysics, 2005, vol. 440, No. 2, pp. 123-132). Accordingly, the inhibition of TF e.g. by monoclonal anti-TF antibodies is of significance in interrupting the coagulation-inflammation cycle in contribution to not only anti-inflammation but also to vascular diseases.

TF expression is observed in many types of cancer and is associated with more aggressive disease. Furthermore, human TF also exist in a soluble alternatively-spliced form, asHTF. It has recently been found that asHTF promotes tumor growth (Hobbs et al. 2007 Thrombosis Res. 120(2) S13-S21).

Antibodies binding to TF have been disclosed in the prior art:

WO98/40408 discloses antibodies that can bind native human TF, either alone or present in a TF:VIIa complex, effectively preventing factor X binding to TF or that complex, and thereby reducing blood coagulation. It is disclosed that the antibodies may be used to alleviate thromboses following an invasive medical procedure such as arterial or cardiac surgery or to eliminate blood coagulation arising from us of medical implementation. Further antibodies are disclosed to be employed in in vivo diagnostic methods including in vivo diagnostic imaging of native human TF.

WO04/094475 provides antibodies capable of binding to human tissue factor, which do not inhibit factor mediated blood coagulation compared to a normal plasma control. Human antibodies are not described. It is alleged that the antibody may be used for treatment of cancer.

WO03/093422 relates to antibodies that bind with greater affinity to the TF:VIIa complex than to TF alone. Use of the antibodies as anticoagulant in the treatment of certain diseases, such as sepsis, disseminated intravascular coagulation, ischemic stroke, thrombosis, acute coronary syndromes and coagulopathy in advanced cancer is proposed.

WO01/27079 discloses compositions and methods for inhibiting abnormal cell proliferation, particularly endothelial cell proliferation, such as cancer, abnormal development of embryos, malfunctioning of immune responses, as well as angiogenesis related to neovasularization and tumor growth. Many active substances, including antibodies, are proposed, but no specific antibodies are disclosed.

WO03/037361 relates to us of TF agonist or antagonist for treatment related to apoptosis.

WO03/029295 relates to isolated human antibodies that immunoreact with human TF to inhibit the binding of coagulation factor VIIa. However, the application does not disclose a single example of an antibody having these properties.

A number of monoclonal antibody therapies are approved to treat different tumor types, including e.g. bevacizumab (Avastin®), cetuximab (Erbitux®), panitumumab (Vectibix™) and trastuzumab (Herceptin®).

SUMMARY OF THE INVENTION

Although much progress has been made, there remains a need for improved methods of treating serious diseases, e.g. improved treatment of cancer, based on therapeutic antibodies.

It is an object of the present invention to provide novel highly specific and effective human anti-TF antibodies for medical use. The antibodies of the invention exhibit TF binding characteristics that differ from the antibodies described in the art. In preferred embodiments, the antibodies of the invention have a high affinity towards human tissue factor, mediate antibody-dependent cellular cytotoxicity (ADCC), inhibit FVIIa binding to TF, inhibit FVIIa-induced ERK phosphorylation and IL8 release, do not or poorly inhibit coagulation.

BRIEF DESCRIPTION OF THE DRAWINGS

FIG. 1: Alignment of sequences of the antibodies of the present invention. CDR1, CDR2 and CDR3 according to IMGT are highlighted: sequences in italics represent the CDR1 region, underlined sequences represent the CDR2 region, bold sequences represent the CDR3 region.

FIG. 2: IgG4 sequences (SEQ ID NO: 113-114)

SEQ ID NO: 113: The amino acid sequence of the wild-type CH region of human IgG4. The Sequence in italics represents the CH1 region, highlighted sequence represents the hinge region, regular sequence represents the CH2 region and underlined sequence represents the CH3 region.

SEQ ID NO: 114: The amino acid sequence of the hinge-less CH region of a human IgG4

Figure 3:
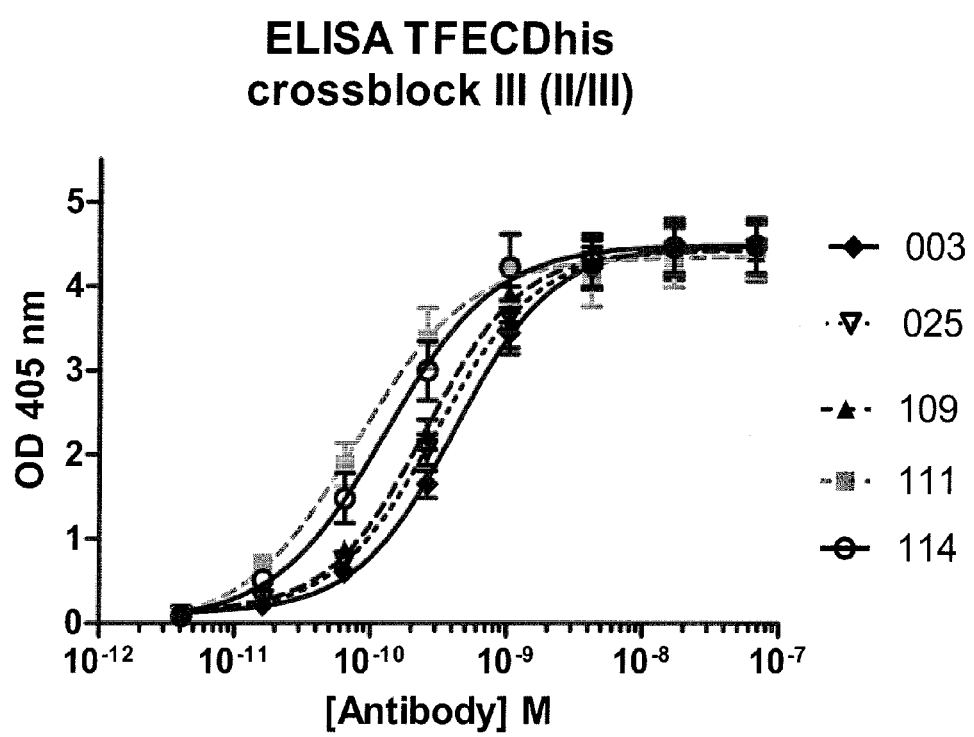

FIG. 3: Binding of anti-TF HuMabs to the extracellular domain of TF.

Figure 4:
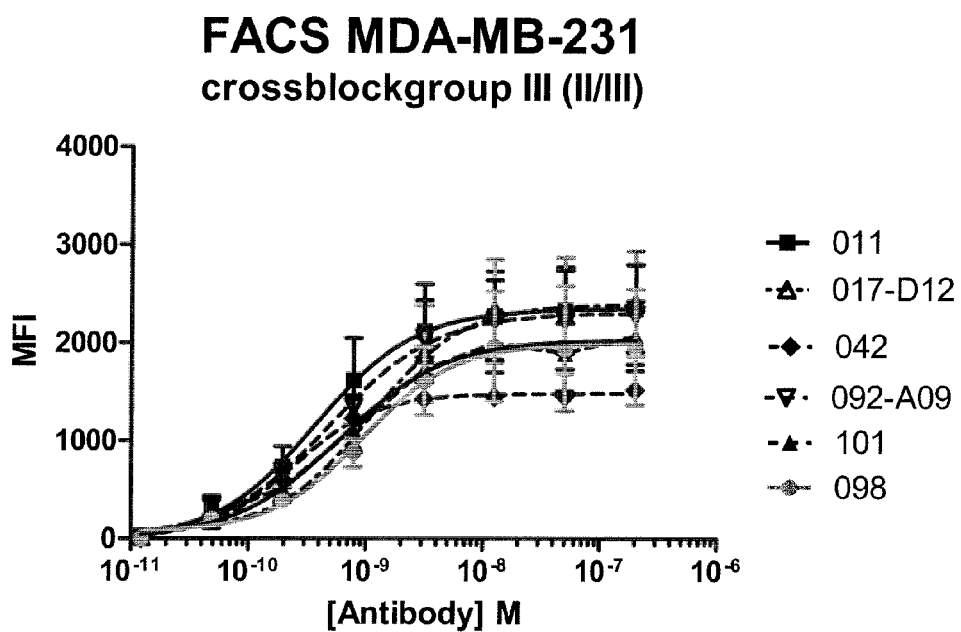

FIG. 4: Binding of anti-TF HuMabs to membrane bound TF.

Figure 5:
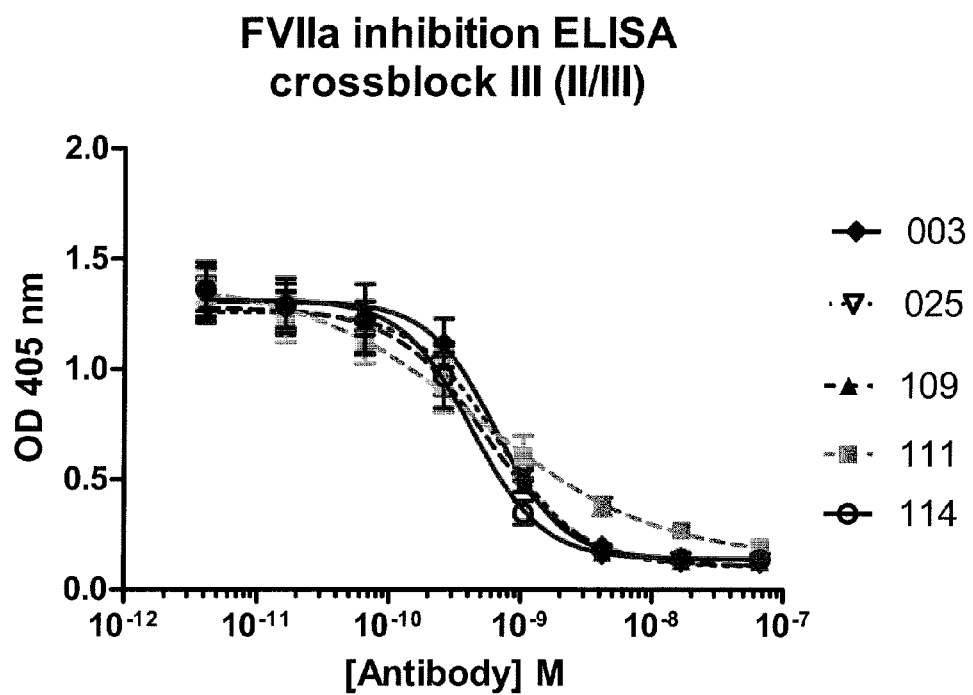

FIG. 5: Inhibition of FVIIa binding to TF.

FIG. 6: Inhibition of FVIIa induced ERK phosphorylation

FIG. 6a: Inhibition of FVIIa induced ERK phosphylation

FIG. 7: Inhibition of FVIIa induced IL-8 release.

Figure 8:
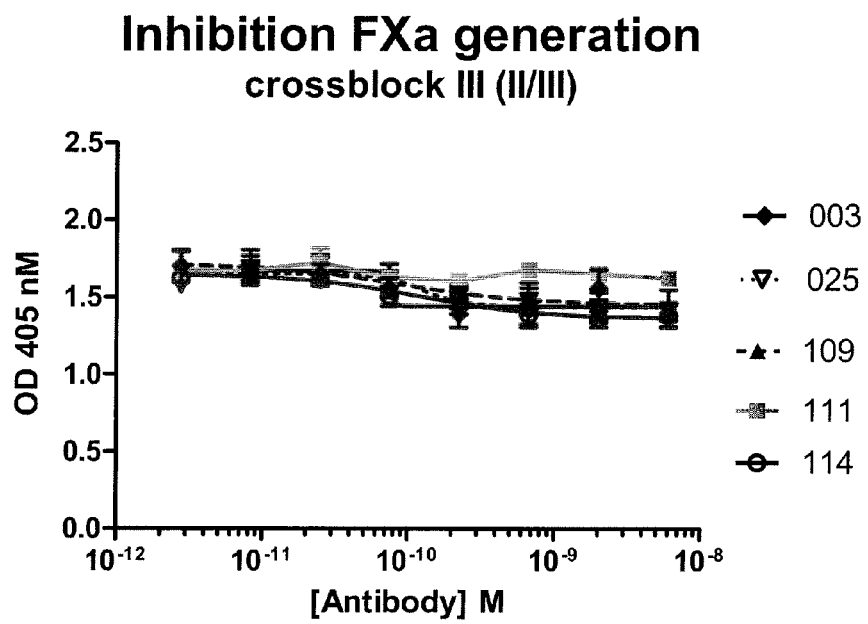

FIG. 8: Inhibition of FXa generation.

Figure 9:
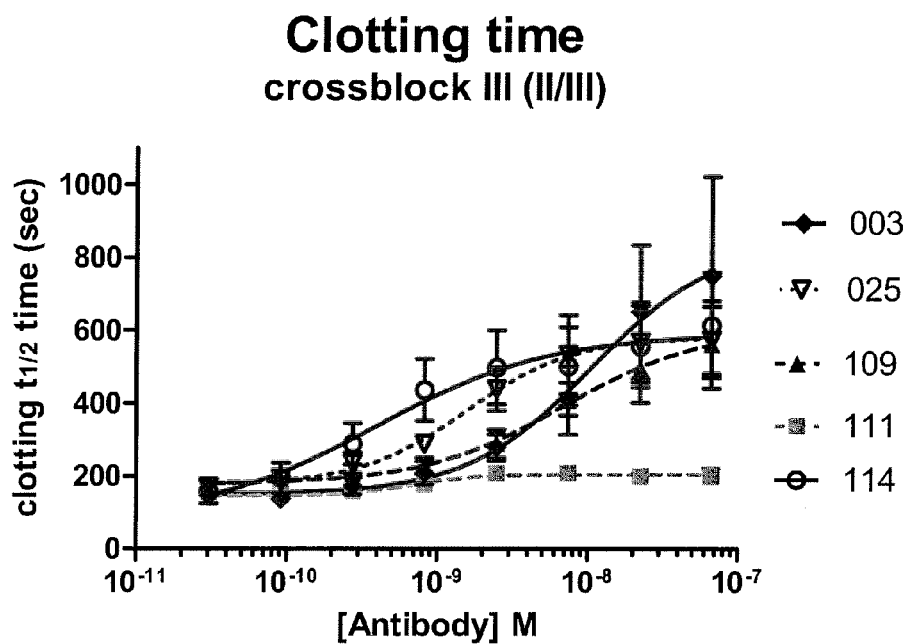

FIG. 9: Inhibition of blood coagulation.

Figure 10:
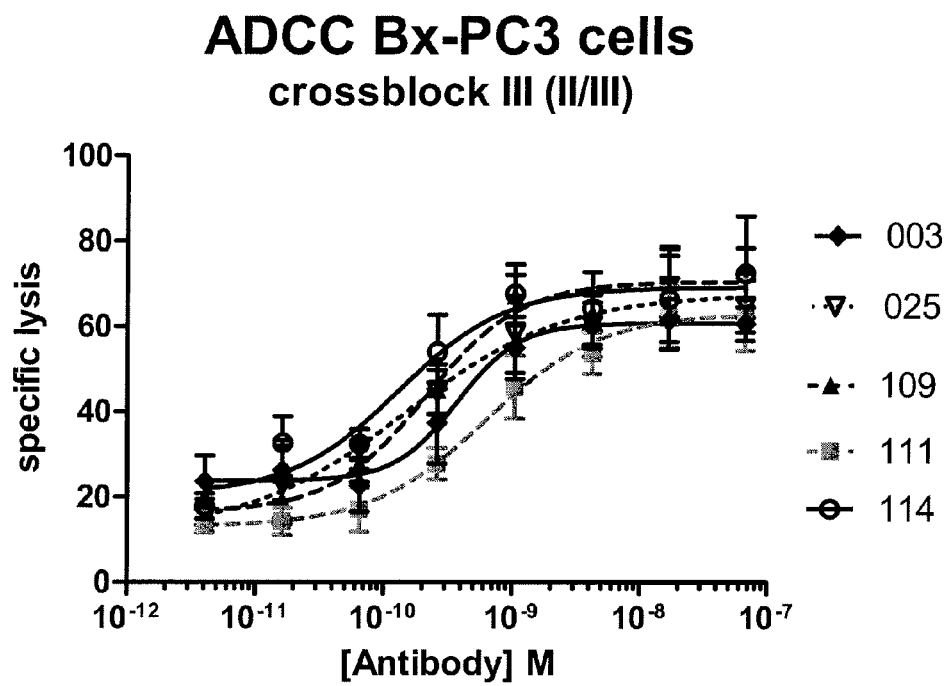

FIG. 10: TF-HuMabs induces lysis of Bx-PC3 cells by ADCC

Figure 11:
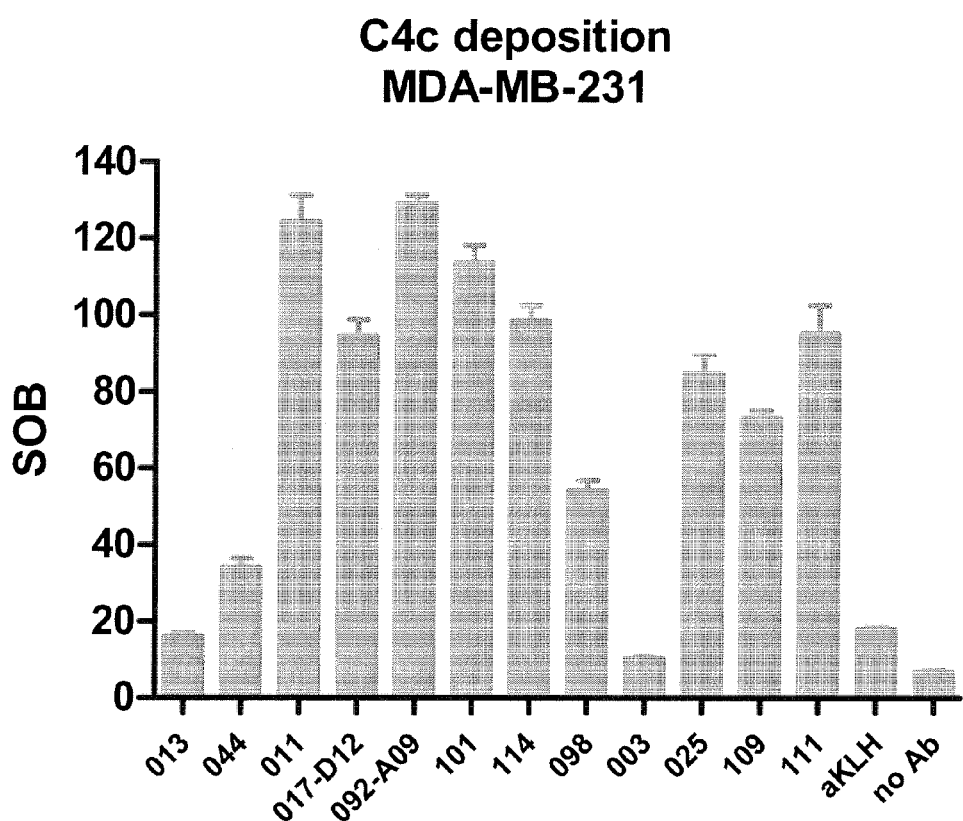
Figure 11:
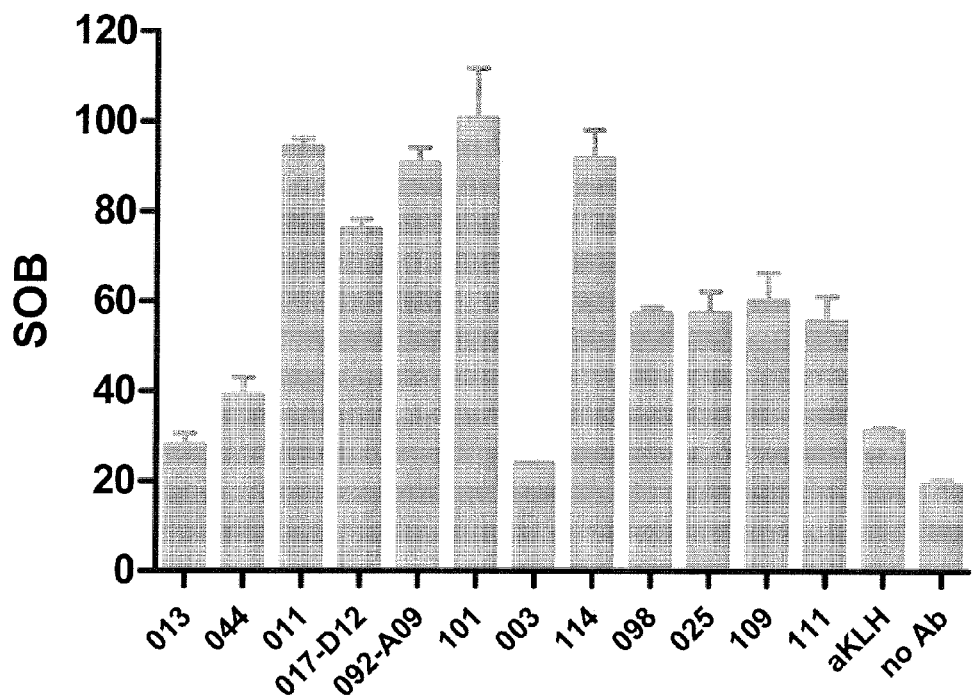
Figure 11:
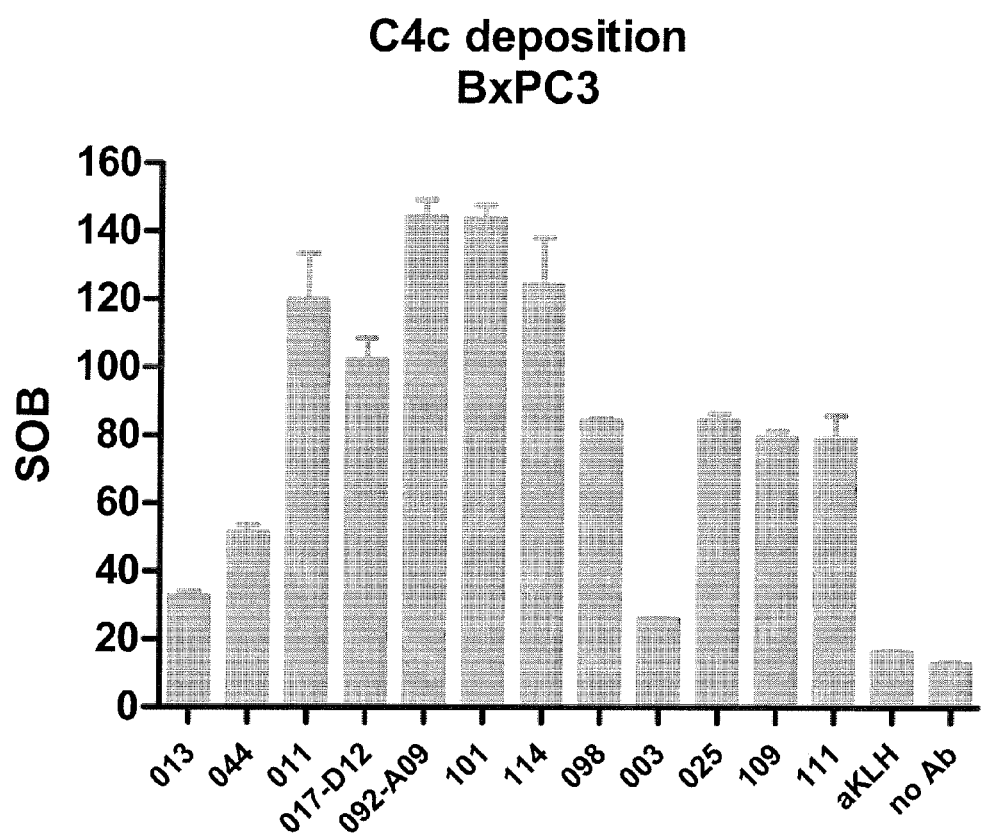
Figure 11:
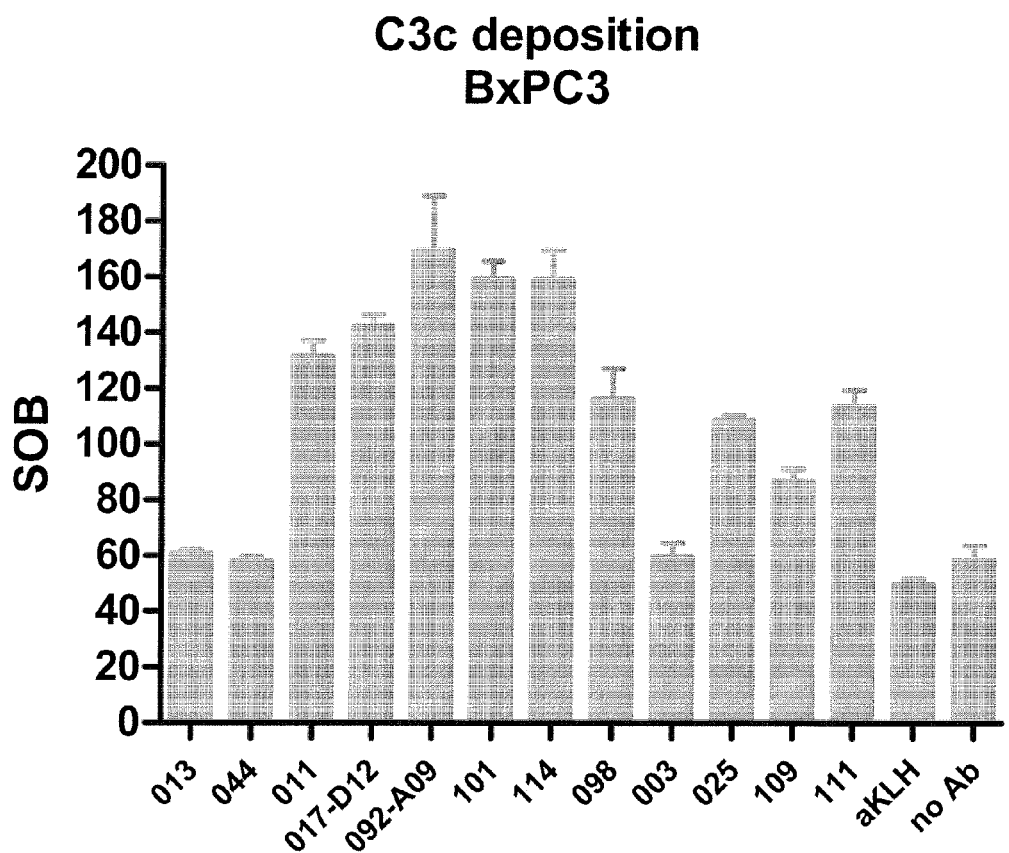

FIG. 11: Deposition of complement components C3c and C4c on target cells.

Figure 12:
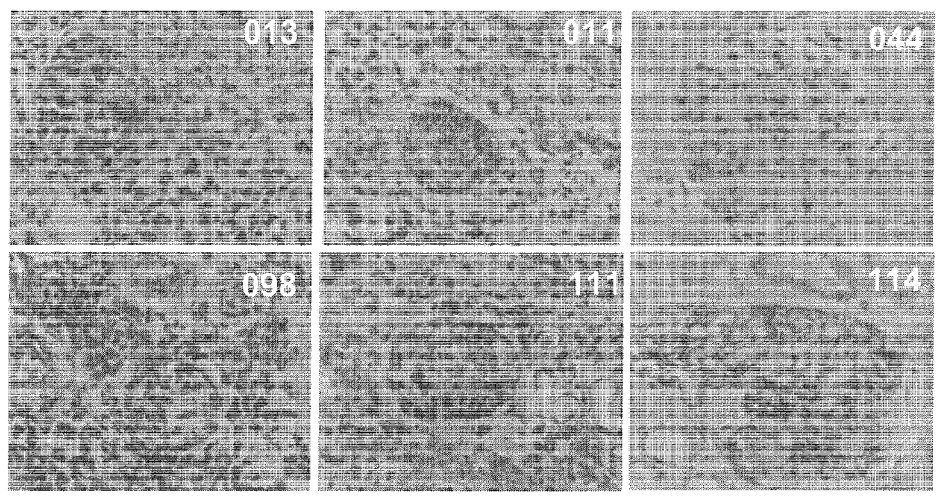

FIG. 12: Immunohistochemical analysis of binding of TF-HuMabs to glomeruli.

Figure 13:
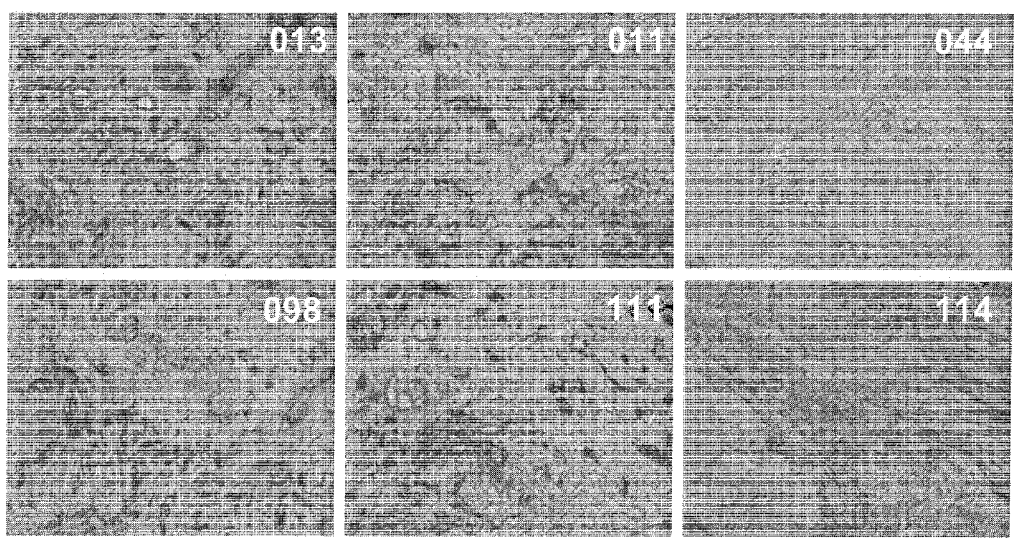

FIG. 13: Immunohistochemical analysis of binding of TF-HuMabs to pancreatic tumors.

Figure 14:
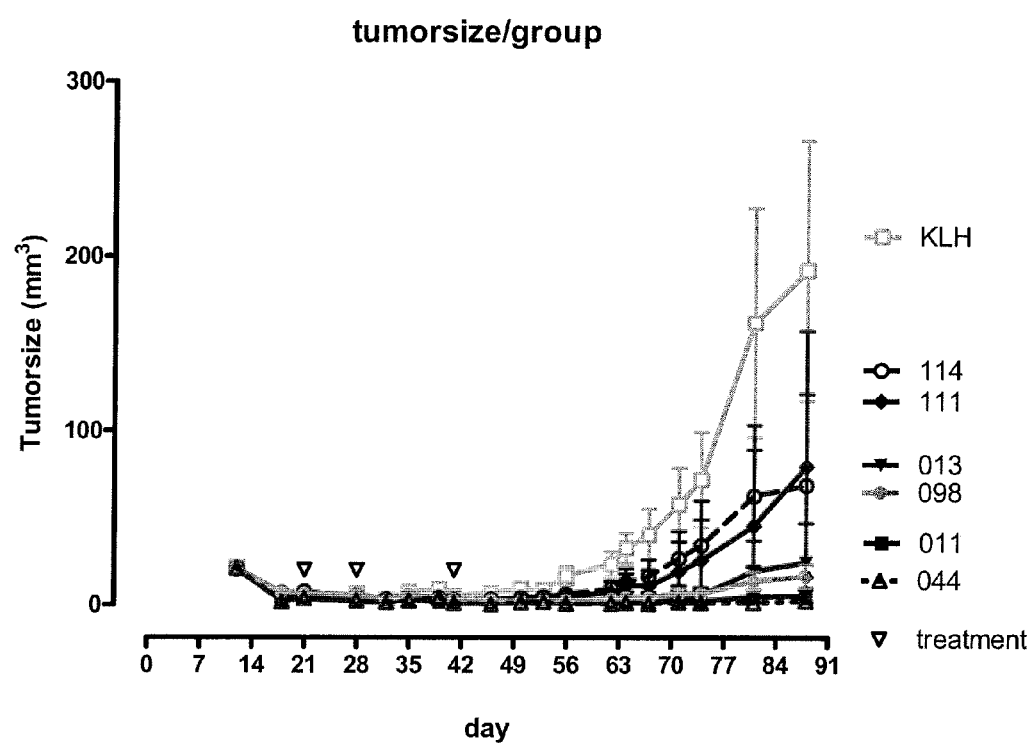
Figure 14:
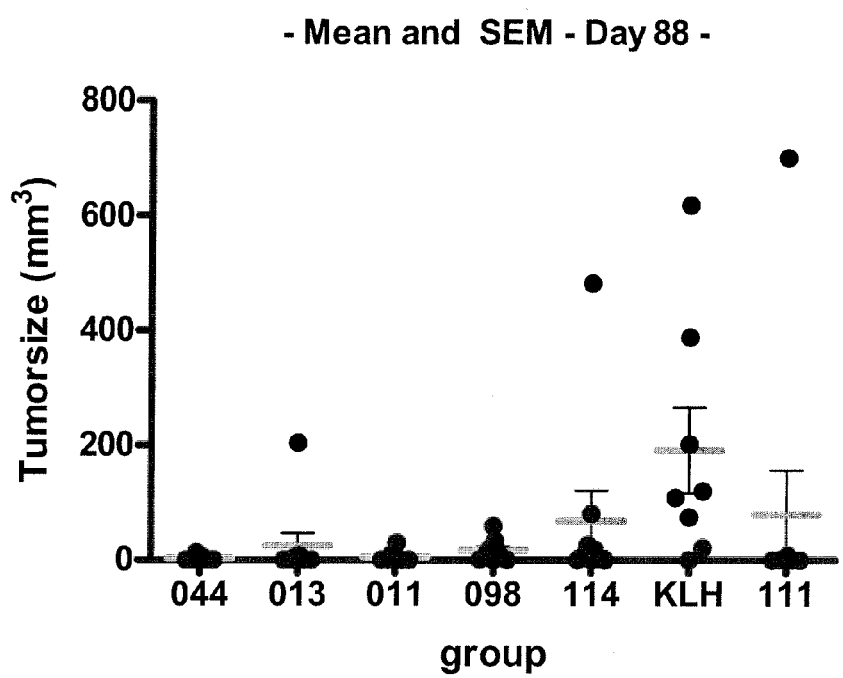

FIG. 14: In vivo efficacy of TF-HuMabs in established MDA-MB-231 tumor xenograft.

Figure 15:
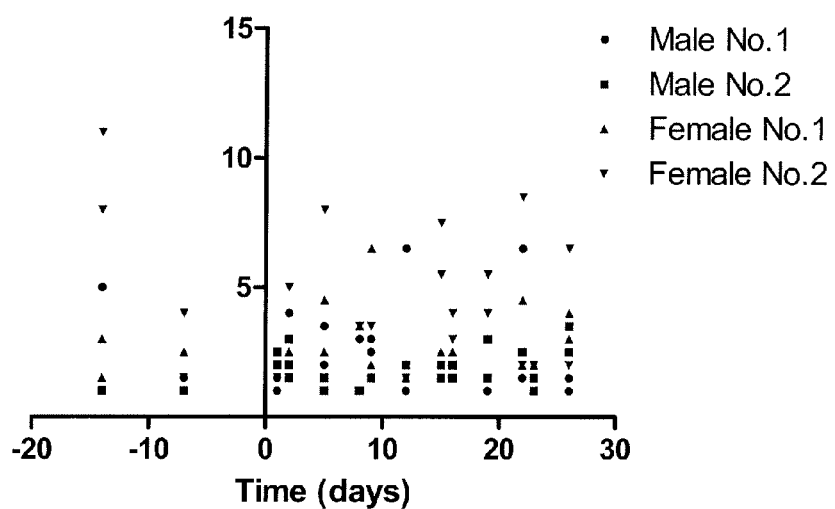

FIG. 15: Bleeding time determined in cynomolgus monkeys upon intravenous injections of TF-specific HuMab 011. The antibody was administered on day 1 (0 mg/kg), 8 (1 mg/kg), (10 mg/kg) and 22 (100 mg/kg).

Figure 16:
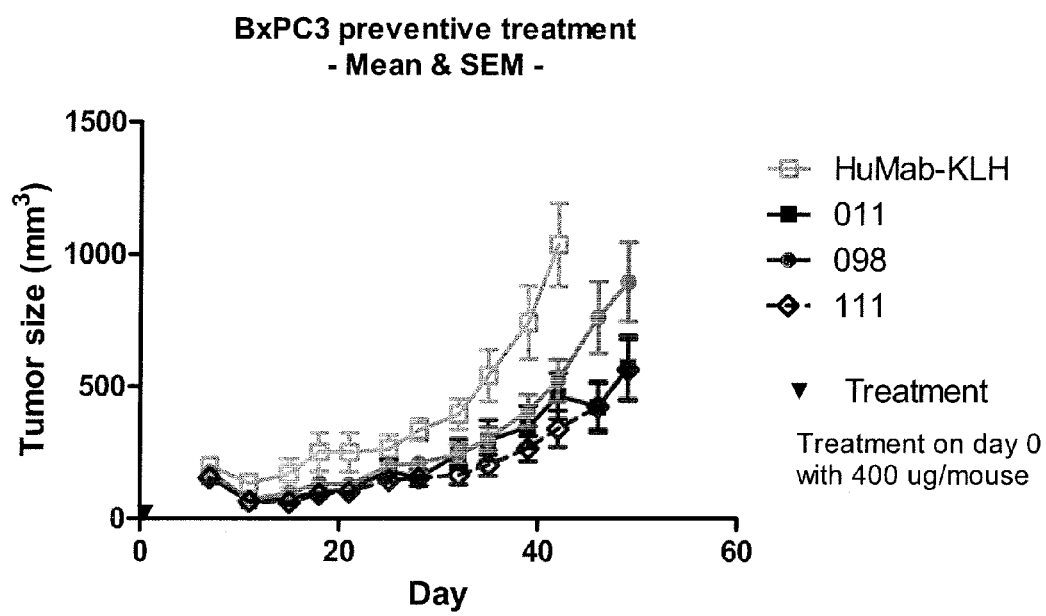

FIG. 16: In vivo efficacy of TF-HuMabs in a prophylactic and established BX-PC3 tumor xenograft.

FIGS. 17A-17B: Shuffle construct and TF domains. FIG. 17A: TFhs/1-295: SEQ ID NO: 113, TFhs1-41 mm/1-289: SEQ ID NO: 114, TFhs42-84 mm/1-295: SEQ ID NO: 115, TFhs85-122 mm/1-301: SEQ ID NO: 116, TFhs123-137 mm/1-295: SEQ ID NO: 117, TFhs138-159 mm/1-295: SEQ ID NO: 118, TFhs160-184 mm/1-295: SEQ ID NO: 119, TFhs185-225 mm/1-295: SEQ ID NO: 120, TFhs226-250 mm/1-295: SEQ ID NO: 121, TFhsmm/1-294: SEQ ID NO: 122. FIG. 17B: TFmm/1-294: SEQ ID NO: 123, TFmmhs/1-295: SEQ ID NO: 124, TFmm1-47hs/1-300: SEQ ID NO: 125, TFmm48-90hs/1-294: SEQ ID NO: 126, TFmm91-122hs/1-288: SEQ ID NO: 127, TFmm123-137hs/1-294: SEQ ID NO: 128, TFmm138-159hs/1-294: SEQ ID NO: 129, TFmm160-184hs/1-294: SEQ ID NO: 130, TFmm185-225hs/1-294: SEQ ID NO: 131, TFmm226-250hs/1-294: SEQ ID NO: 132.

FIGS. 18A-18O: binding of anti-TF antibodies to TF shuffle constructs

FIG. 19: Binding of HuMab-TF Fab fragments to extracellular domain of TF, ELISA

FIG. 20: Binding of HuMab-TF Fab fragments to extracellular domain of TF, FACS

FIG. 21: Binding profile of anti-TF HuMabs dependent on the number of TF molecules expressed.

DETAILED DESCRIPTION OF THE INVENTION

Definitions

The terms "tissue factor", "TF", "CD142", "tissue factor antigen", "TF antigen" and "CD142 antigen are used interchangeably herein, and, unless specified otherwise, include any variants, isoforms and species homologs of human tissue factor which are naturally expressed by cells or are expressed on cells transfected with the tissue factor gene.

The term "immunoglobulin" refers to a class of structurally related glycoproteins consisting of two pairs of polypeptide chains, one pair of light (L) low molecular weight chains and one pair of heavy (H) chains, which may all four be interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region. The heavy chain constant region typically is comprised of three domains, $C_H1$, $C_H2$, and $C_H3$. Each light chain typically is comprised of a light chain variable region (abbreviated herein as $V_L$ or VL) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is according to IMGT., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. An anti-TF antibody may also be a bispecific antibody, diabody, or similar molecule (see for instance PNAS USA 90(14), 6444-8 (1993) for a description of diabodies). Indeed, bispecific antibodies, diabodies, and the like, provided by the present invention may bind any suitable target in addition to a portion of tissue factor or tissue factor FVIIa complex. As indicated above, the term antibody herein, unless otherwise stated or clearly contradicted by context, includes fragments of an antibody that retain the ability to specifically bind to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab); (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of a $V_L$ and $V_H$ domains, (v) a dAb fragment (Ward et al., Nature 341, 544-546 (1989)), which consists essentially of a $V_H$ domain and also called domain antibodies (Holt et al; Trends Biotechnol. 2003 November; 21(11):484-90); (vi) camelid or nanobodies (Revets et al; Expert Opin Biol Ther. 2005 January; 5(1):111-24) and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

An "anti-TF antibody" is an antibody as described above, which binds specifically to the antigen tissue factor.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or during gene rearrangement or by somatic mutation in vivo). However, the term "human antibody", as used herein, is not intended to include antibodies in which CDR sequences derived from the germline of another mammalian species, such as a mouse, have been grafted onto human framework sequences.

In a preferred embodiment, the antibody of the invention is isolated. An "isolated antibody," as used herein, is intended to refer to an antibody which is substantially free of other antibodies having different antigenic specificities (for instance an isolated antibody that specifically binds to tissue factor is substantially free of antibodies that specifically bind antigens other than tissue factor). An isolated antibody that specifically binds to an epitope, isoform or variant of human tissue factor may, however, have cross-reactivity to other related antigens, for instance from other species (such as tissue factor species homologs). Moreover, an isolated antibody may be substantially free of other cellular material and/or chemicals. In one embodiment of the present invention, two or more "isolated" monoclonal antibodies having different antigen-binding specificities are combined in a well-defined composition.

When used herein in the context of two or more antibodies, the term "competes with" or "cross-competes with" indicates that the two or more antibodies compete for binding to TF, e.g. compete for TF binding in the assay described in Example 6 herein. For some pairs of antibodies, competition in the assay of Example 6 is only observed when one antibody is coated on the plate and the other is used to compete, and not vice versa. The term "competes with" when used herein is also intended to cover such combinations antibodies.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

As used herein, the term "binding" in the context of the binding of an antibody to a predetermined antigen typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore® 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "$k_d$" (sec$^{-1}$), as used herein, refers to the dissociation rate constant of a particular antibody-antigen interaction. Said value is also referred to as the $k_{off}$ value.

The term "$k_a$" (M$^{-1}$×sec$^{-1}$), as used herein, refers to the association rate constant of a particular antibody-antigen interaction.

The term "$k_D$" (M), as used herein, refers to the dissociation equilibrium constant of a particular antibody-antigen interaction.

The term "$K_A$" (M$^{-1}$), as used herein, refers to the association equilibrium constant of a particular antibody-antigen interaction and is obtained by dividing the $k_a$ by the $k_d$.

The present invention also provides antibodies comprising functional variants of the $V_L$ region, $V_H$ region, or one or more CDRs of the antibodies of the examples. A functional variant of a $V_L$, $V_H$, or CDR used in the context of an anti-TF antibody still allows the antibody to retain at least a substantial proportion (at least about 50%, 60%, 70%, 80%, 90%, 95% or more) of the affinity/avidity and/or the specificity/selectivity of the parent antibody and in some cases such an anti-TF antibody may be associated with greater affinity, selectivity and/or specificity than the parent antibody.

Such functional variants typically retain significant sequence identity to the parent antibody. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences may be accomplished using a mathematical algorithm, as described in the non-limiting examples below.

The percent identity between two nucleotide sequences may be determined using the GAP program in the GCG software package (available on the world wide web at gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences may also be determined using the algorithm of E. Meyers and W. Miller, Comput. Appl. Biosci 4,11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970)) algorithm which has been incorporated into the GAP program in the GCG software package (available on the world wide web at gcg.com), using either a Blossum 62 matrix or a PAM250 matrix, and a gap weight of 16, 14, 12, 10, 8, 6, or 4 and a length weight of 1, 2, 3, 4, 5, or 6.

The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, about 95% or more (e.g., about 65-99%, such as about 96%, 97% or 98%) of the substitutions in the variant are conservative amino acid residue replacements.

The sequence of CDR variants may differ from the sequence of the CDR of the parent antibody sequences through mostly conservative substitutions; for instance at least 10, such as at least 9, 8, 7, 6, 5, 4, 3, 2 or 1 of the substitutions in the variant are conservative amino acid residue replacements.

In the context of the present invention, conservative substitutions may be defined by substitutions within the classes of amino acids reflected in one or more of the following three tables:

| Amino acid residue classes for conservative substitutions | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

| Alternative conservative amino acid residue substitution classes | | | |
|---|---|---|---|
| 1 | A | S | T |
| 2 | D | E | |
| 3 | N | Q | |
| 4 | R | K | |
| 5 | I | L | M |
| 6 | F | Y | W |

| Alternative Physical and Functional Classifications of Amino Acid Residues | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) Proteins: Structure and Molecular Properties (2d Ed. 1993), W.H. Freeman and Company.

In one embodiment of the present invention, conservation in terms of hydropathic/hydrophilic properties and residue weight/size also is substantially retained in a variant CDR as compared to a CDR of an antibody of the examples (e.g., the weight class, hydropathic score, or both of the sequences are at least about 50%, at least about 60%, at least about 70%, at least about 75%, at least about 80%, at least about 85%, at least about 90%, at least about 95%, or more (e.g., about 65-99%) retained). For example, conservative residue substitutions may also or alternatively be based on the replacement of strong or weak based weight based conservation groups, which are known in the art.

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45%, such as at least about 55%, at least about 65%, at least about 75%, at least about 85%, at least about 90%, at least about 95%, or more (e.g., about 70-99%) similarity to the parent peptide.

As used herein, "isotype" refers to the immunoglobulin class (for instance IgG1, IgG2, IgG3, IgG4, IgD, IgA, IgE, or IgM) that is encoded by heavy chain constant region genes.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody V domain sequence is at least 90%, such as at least 95%, for instance at least 96%, such as at least 97%, for instance at least 98%, or such as at least 99% identical in amino acid V domain sequence to the amino acid sequence encoded by the germline immunoglobulin gene. Typically, outside the heavy chain CDR3, a human antibody derived from a particular human germline sequence will display no more than 20 amino acid differences, e.g. no more than 10 amino acid differences, such as no more than 9, 8, 7, 6 or 5, for instance no more than 4, 3, 2, or 1 amino acid difference from the amino acid sequence encoded by the germline immunoglobulin gene.

As used herein, the term "inhibits growth" (e.g. referring to cells, such as tumor cells) is intended to include any measurable decrease in the cell growth when contacted with an anti-TF antibody as compared to the growth of the same cells not in contact with an anti-TF antibody, e.g., the inhibition of growth of a cell culture by at least about 10%, 20%, 30%, 40%, 50%, 60%, 70%, 80%, 90%, 99%, or 100%. Such a decrease in cell growth can occur by a variety of mechanisms, e.g. effector cell phagocytosis, ADCC, CDC, and/or apoptosis.

The term "bispecific molecule" is intended to include any agent, such as a protein, peptide, or protein or peptide complex, which has two different binding specificities. For example, the molecule may bind to, or interact with, (a) a cell surface antigen and (b) an Fc receptor on the surface of an effector cell. The term "bispecific antibody" is intended to include any anti-TF antibody, which is a bispecific molecule. The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see for instance Holliger, P. et al., PNAS USA 90, 6444-6448 (1993), Poljak, R. J. et al., Structure 2, 1121-1123 (1994)).

An "antibody deficient in effector function" or an "effector-function-deficient antibody" refers to an antibody which has a significantly reduced or no ability to activate one or more effector mechanisms, such as complement activation or Fc receptor binding. Thus, effector-function deficient antibodies have significantly reduced or no ability to mediate antibody-dependent cell-mediated cytotoxicity (ADCC) and/or complement-dependent cytotoxicity (CDC). An example of such an antibody is IgG4.

The term "monovalent antibody" means in the context of the present invention that an antibody molecule is capable of binding a single molecule of the antigen, and thus is not able of antigen crosslinking.

The term "stabilized IgG4 antibody" refers to an IgG4 antibody which has been modified to reduce half-molecule exchange (see van der Neut Kolfschoten M et al. (2007) Science 14; 317(5844) and references therein, and also Labrijn et al. (2009) Nature Biotechnology, 27, 767-771.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express specific Fc receptors and carry out specific immune functions. In some embodiments, an effector cell is capable of inducing antibody-dependent cellular cytotoxicity (ADCC), such as a natural killer cell, capable of inducing ADCC. For example, monocytes, macrophages, which express FcR are involved in specific killing of target cells and presenting antigens to other components of the immune system, or binding to cells that present antigens. In some embodiments, an effector cell may phagocytose a target antigen or target cell. The expression of a particular FcR on an effector cell may be regulated by humoral factors such as cytokines. For example, expression of FcγRI has been found to be upregulated by interferon γ (IFN-γ) and/or G-CSF. This enhanced expression increases the cytotoxic activity of FcγRI-bearing cells against targets. An effector cell can phagocytose or lyse a target antigen or a target cell.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication defective retroviruses, adenoviruses and adeno-associated viruses), which serve equivalent functions.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK293 cells, NS/0 cells, and lymphocytic cells.

The term "transfectoma", as used herein, includes recombinant eukaryotic host cells expressing the antibody, such as CHO cells, NS/0 cells, HEK293 cells, plant cells, or fungi, including yeast cells.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-TF antibodies when immunized with TF antigen and/or cells expressing TF. The human heavy chain transgene may be integrated into the chromosomal DNA of the mouse, as is the case for transgenic mice, for instance HuMAb mice, such as HCo7 or HCo12 mice, or the human heavy chain transgene may be maintained extrachromosomally, as is the case for transchromosomal KM mice as described in WO02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, nonhuman animal can also be used for production of antibodies against a specific antigen by introducing genes encoding such specific antibody, for example by operatively linking the genes to a gene which is expressed in the milk of the animal.

"Treatment" refers to the administration of an effective amount of a therapeutically active compound of the present invention with the purpose of easing, ameliorating, arresting or eradicating (curing) symptoms or disease states.

An "effective amount" refers to an amount effective, at dosages and for periods of time necessary, to achieve a desired therapeutic result. A therapeutically effective amount of an anti-TF antibody may vary according to factors such as the disease state, age, sex, and weight of the individual, and the ability of the anti-TF antibody to elicit a desired response in the individual. A therapeutically effective amount is also one in which any toxic or detrimental effects of the antibody or antibody portion are outweighed by the therapeutically beneficial effects.

An "anti-idiotypic" (Id) antibody is an antibody which recognizes unique determinants generally associated with the antigen-binding site of an antibody.

FURTHER ASPECTS AND EMBODIMENTS OF THE INVENTION

As described above, in a first aspect, the invention relates to a human antibody which binds human Tissue Factor.

In one embodiment, the antibody binds to the extracellular domain of Tissue Factor with an apparent affinity ($EC_{50}$) of 3 nM or less, such as 0.50 nM or less, e.g. 0.35 nM or less, such as 0.20 nM or less, e.g. 0.1 nM or less, when determined as described in the assay in Example 13.

In another embodiment, the antibody binds to mammalian cells expressing Tissue Factor, such as A431 cells transfected with a construct encoding Tissue Factor, preferably with an apparent affinity ($EC_{50}$) of 10 nM or less, e.g. 8 nM or less, such as 5 nM or less, e.g. 2 nM or less, such as 1 nM or less, e.g. 0.5 nM or less, such as 0.3 nM or less, when determined as described in the assay in Example 14.

In another embodiment, the antibody is capable of inducing antibody-dependent cellular cytotoxicity in A431 cells, preferably with an $EC_{50}$ value of 2 nM or less, e.g. 1 nM or less, such as 0.7 nM or less or 0.3 nM or less, such as 0.2 nM or less, or 0.1 nM or less, or 0.05 nM or less, when determined as described in the assay in Example 20.

In another embodiment, the antibody is effective in inhibiting growth of established MDA-MB-231 tumors, when determined by the method described in Example 24 and/or in inhibiting growth of established BxPC3 tumors, when determined by the method described in Example 26.

In another embodiment, the antibody inhibits tissue factor induced blood coagulation, preferably with a median inhibition concentration of less than 10 nM, such as less than 5 nM, e.g. less than 2 nM, such as less than 1 nM when determined as described in the assay in Example 19.

In another embodiment, the antibody does not inhibit coagulation. In an embodiment the coagulation is inhibited with a maximum of 30%, such as 25%, such as 20%, such as 15%, such as 10% or such as 5% compared to native level.

In a further embodiment, the antibody inhibits FVIIa binding to Tissue Factor, preferably with a maximum inhibition value of inhibition of more than 80%, such as more than 90% when determined as described in the assay in Example 15.

In a further embodiment, the antibody inhibits FVIIa-induced IL-8 release by MDA-MB-231 cells, preferably with a maximum inhibition value of inhibition of more than 40%, such as more than 50%, e.g. more than 60%, when determined in as described in the assay in Example 17.

In a further embodiment, the antibody inhibits conversion of FX into FXa by the TF/FVIIa complex, preferably by less than 50%, e.g. less than 40%, such as in the range of 1-30%, when determined as described in the assay in Example 18.

In a further embodiment, the antibody competes for Tissue Factor binding with an antibody comprising a VH region comprising the sequence of SEQ ID NO:9 and a VL region comprising the sequence of SEQ ID NO:65.

In a further embodiment, the binding of the antibody of the invention to Tissue Factor does not involve all three of the following residues: W in position 45, K in position 46 or Y in position 94 of Tissue Factor. In an even further embodiment, the binding does not involve any of the following residues: W in position 45, K in position 46 or Y in position 94 (these number refer to mature TF, the equivalent positions in Genbank entry NP_001984 are 77, 78 and 126).

In another embodiment of the antibody of the invention, the antibody competes for Tissue Factor binding with an antibody comprising a VH region comprising the sequence of SEQ ID NO:37 and a VL region comprising the sequence of SEQ ID NO:93.

In a further embodiment, the antibody inhibits FVIIa induced ERK phosphorylation, preferably with a median inhibition concentration of less than 10 nM, such as less than 5 nM, e.g. less than 2 nM when determined as described in the assay in Example 16.

In a further embodiment, the antibody inhibits ERK phosphorylation preferably with a median inhibition concentration of less than 10 nM, such as less than 5 nM, e.g. less than 2 nM when determined as described in the assay in Example 16 and do not inhibit FVII induced IL-8 release as described in the assay in Example 17 by more than maximum 10%

In a further embodiment, the antibody is capable of inducing C3c and C4c deposition, preferably wherein the antibody is capable of inducing C3c and C4c deposition as determined in Example 21.

In a further embodiment, the antibody Fab fragments binds to the extracellular domain of tissue factor as described in example 28 with an EC50 value of below 0.1 μg/mL., such as below 0.05 μg/mL., e.g. below 0.04 μg/mL. as measured by ELISA.

In a further embodiment, the antibody Fab fragments binds to the extracellular domain of tissue factor as described in example 28 with an EC50 value of above 1.0 μg/mL. as measured by ELISA.

In a further embodiment, the antibody Fab fragments binds to the extracellular domain of tissue factor as described in example 28 with an EC50 value of below 10 μg/mL, such as below 1 μg/mL, e.g. below 0.5 μg/mL, or below 0.2 μg/mL.

In a further embodiment, the antibody binds to human tissue factor and not murine tissue factor and shows reduced binding as compared to binding to human TF to the shuffle construct 42-84 mm, containing the human sequence for TF except for amino acid 42-84, which has been replaced with mouse sequence, as described in example 27.

In a further embodiment, the antibody binds to human tissue factor and not murine tissue factor and shows reduced binding as compared to binding to human TF to the shuffle construct 85-122, containing the human sequence for TF except for amino acid 85-122, which has been replaced with mouse sequence, as described in example 27.

In a further embodiment, the antibody binds to human tissue factor and not murine tissue factor and shows reduced binding as compared to binding to human TF to the shuffle construct 123-137 mm containing the human sequence for TF except for amino acid 123-137, which has been replaced with mouse sequence, as described in example 27.

In a further embodiment, the antibody binds to human tissue factor and not murine tissue factor and shows reduced binding as compared to binding to human TF to the shuffle construct 185-225 mm containing the human sequence for TF except for amino acid 185-225, which has been replaced with mouse sequence, as described in example 27.

In a further embodiment, the antibody binds to human tissue factor and not murine tissue factor and shows reduced binding as compared to binding to human TF to both the shuffle construct 226-250 mm containing the human sequence for TF except for amino acid 226-250, which has been replaced with mouse sequence, as described in example 27.

In a further embodiment, the antibody shows reduced binding as compared to binding to human TF to more than one shuffle construct. In an embodiment an antibody shows reduced binding to construct 42-84 mm as well as to 85-122 mm. In an embodiment an antibody shows reduced binding to 123-137 mm as well as to construct 185-225 mm. In an embodiment an antibody shows reduced binding to construct 123-137 mm as well as to construct 185-225 mm and further to construct 226-250 mm.

In a further embodiment, the antibody is capable of inducing C3c and C4c deposition, preferably wherein the antibody is capable of inducing C3c and C4c deposition as determined in Example 21.

In one embodiment of the antibody of the invention, said antibody
- competes for Tissue Factor binding with an antibody comprising a VH region comprising the sequence of SEQ ID NO:9 and a VL region comprising the sequence of SEQ ID NO:65, and
- does not compete for Tissue Factor binding with an antibody comprising a VH region comprising the sequence of SEQ ID NO:37 and a VL region comprising the sequence of SEQ ID NO:93.

In a further embodiment, the antibody comprises a VH CDR3 region having
  a) the sequence as set forth in
    SEQ ID No: 12,
    SEQ ID No: 16,
    SEQ ID No: 20,
    SEQ ID No: 24,
    SEQ ID No: 28,
  or
  b) a variant of any of said sequences, such as a variant having at most 1, 2, 3, 4 or 5 amino-acid modifications, preferably substitutions, such as conservative substitutions.

In a further embodiment, the antibody comprises a VH CDR3 region having the sequence as set forth in SEQ ID NO: 12 or a variant thereof, wherein the variant comprises modification in one or more of the positions 2, 3, 6, 9 and 11, preferably where the modification is a substitution, more preferably where the substitution is selected from the group consisting of
  a. R is substituted with K when in position 2,
  b. S is substituted with A or T when in position 3,
  c. G is substituted with T when in position 6,
  d. L is substituted with F when in position 9, and
  e. S is substituted with Y when in position 11.

In another embodiment, the antibody comprises:
  a) a VH region comprising the CDR1, 2 and 3 sequences of SEQ ID NO:10, 11 and 12 and a VL region comprising the CDR1, 2 and 3 sequences of SEQ ID NO:66, 67 and 68,
  b) a VH region comprising the CDR1, 2 and 3 sequences of SEQ ID NO:14, 15 and 16 and a VL region comprising the CDR1, 2 and 3 sequences of SEQ ID NO:70, 71 and 72,
  c) a VH region comprising the CDR1, 2 and 3 sequences of SEQ ID NO:18, 19, 20 and a VL region comprising the CDR1, 2 and 3 sequences of SEQ ID NO:74, 75 and 76,
  d) a VH region comprising the CDR1, 2 and 3 sequences of SEQ ID NO:22, 23 and 24 and a VL region comprising the CDR1, 2 and 3 sequences of SEQ ID NO:78, 79 and 80,
  e) a VH region comprising the CDR1, 2 and 3 sequences of SEQ ID NO: 26, 27 and 28 and a VL region comprising the CDR1, 2 and 3 sequences of SEQ ID NO: 82, 83 and 84, or
  f) a variant of any of said antibodies, wherein said variant preferably has at most 1, 2 or 3 amino-acid modifications, more preferably amino-acid substitutions, such as conservative amino-acid substitutions in said sequences.

In a further embodiment, the antibody comprises a VH having
  a) at least 80% identity, such as at least 90%, at least 95%, or at least 98% or 100% identity to a VH region sequence selected from the group consisting of: SEQ ID NO:9, 13, 17, 21 and 25, or
  b) at most 20, such as 15, or 10, or 5, 4, 3, 2 or 1 amino-acid modifications, more preferably amino-acid substitutions, such as conservative amino-acid substitutions as compared to a VH region sequence selected from the group consisting of: SEQ ID NO:9, 13, 17, 21, 21 and 25.

In a further embodiment, the antibody comprises a VL having
  a) at least 80% identity, such as at least 90%, at least 95%, or at least 98% or 100% identity to a VL region sequence selected from the group consisting of: SEQ ID NO:65, 69, 73, 77 and 81, or
  b) at most 20, such as 15, or 10, or 5, 4, 3, 2 or 1 amino-acid modifications, more preferably amino-acid substitutions, such as conservative amino-acid substitutions as compared to a VH region sequence selected from the group consisting of: SEQ ID NO:65, 69, 73, 77 and 81.

In a further embodiment, the antibody comprises:
a) a VH region comprising the sequence of SEQ ID NO:9 and a VL region comprising the sequence of SEQ ID NO: 65,
b) a VH region comprising the sequence of SEQ ID NO:13 and a VL region comprising the sequence of SEQ ID NO:69,
c) a VH region comprising the sequence of SEQ ID NO:17 and a VL region comprising the sequence of SEQ ID NO:73,
d) a VH region comprising the sequence of SEQ ID NO:21 and a VL region comprising the sequence of SEQ ID NO:77,
e) a VH region comprising the sequence of SEQ ID NO:25 and a VL region comprising the sequence of SEQ ID NO:81, or
f) a variant of any of said antibodies, wherein said variant preferably has at most 1, 2 or 3 amino-acid modifications, more preferably amino-acid substitutions, such as conservative amino-acid substitutions in said sequences.

In a further embodiment, the antibody
competes for Tissue Factor binding with an antibody comprising a VH region comprising the sequence of SEQ ID NO:9 and a VL region comprising the sequence of SEQ ID NO:65, and
competes for Tissue Factor binding with an antibody comprising a VH region comprising the sequence of SEQ ID NO:37 and a VL region comprising the sequence of SEQ ID NO:93.

In a further embodiment, the antibody comprises a VH CDR3 region having
a) the sequence as set forth in
SEQ ID No: 8,
SEQ ID No: 52,
or
b) a variant of any of said sequences, such as a variant having at most 1, 2 or 3 amino-acid modifications, preferably substitutions, such as conservative substitutions.

In a further embodiment, the antibody comprises:
a) a VH region comprising the CDR1, 2 and 3 sequences of SEQ ID NO:6, 7 and 8 and a VL region comprising the CDR1, 2 and 3 sequences of SEQ ID NO:62, 63 and 64,
b) a VH region comprising the CDR1, 2 and 3 sequences of SEQ ID NO:50, 51 and 52 and a VL region comprising the CDR1, 2 and 3 sequences of SEQ ID NO:106, 107 and 108, or
c) a variant of any of said antibodies, wherein said variant preferably has at most 1, 2 or 3 amino-acid modifications, more preferably amino-acid substitutions, such as conservative amino-acid substitutions in said sequences.

In a further embodiment, the antibody comprises a VH having
a) at least 80% identity, such as at least 90%, at least 95%, or at least 98% or 100% identity to a VH region sequence selected from the group consisting of: SEQ ID NO:5 and 49, or
b) at most 20, such as 15, or 10, or 5, 4, 3, 2 or 1 amino-acid modifications, more preferably amino-acid substitutions, such as conservative amino-acid substitutions as compared to a VH region sequence selected from the group consisting of: SEQ ID NO:5 and 49.

In a further embodiment, the antibody comprises a VL having
c) at least 80% identity, such as at least 90%, at least 95%, or at least 98% or 100% identity to a VL region sequence selected from the group consisting of: SEQ ID NO: 61 and 105, or
d) at most 20, such as 15, or 10, or 5, 4, 3, 2 or 1 amino-acid modifications, more preferably amino-acid substitutions, such as conservative amino-acid substitutions as compared to a VH region sequence selected from the group consisting of: SEQ ID NO:61 and 105.

In a further embodiment, the antibody comprises:
a) a VH region comprising the sequence of SEQ ID NO:5 and a VL region comprising the sequence of SEQ ID NO:61,
b) a VH region comprising the sequence of SEQ ID NO:49 and a VL region comprising the sequence of SEQ ID NO:105, or
c) a variant of any of said antibodies, wherein said variant preferably has at most 1, 2 or 3 amino-acid modifications, more preferably amino-acid substitutions, such as conservative amino-acid substitutions in said sequences.

In a further embodiment, the antibody
does not compete for Tissue Factor binding with an antibody comprising a VH region comprising the sequence of SEQ ID NO:9 and a VL region comprising the sequence of SEQ ID NO:65, and
competes for Tissue Factor binding with an antibody comprising a VH region comprising the sequence of SEQ ID NO:37 and a VL region comprising the sequence of SEQ ID NO:93.

In a further embodiment, the antibody comprises a VH CDR3 region having
a) the sequence as set forth in
SEQ ID No: 32,
SEQ ID No: 36,
SEQ ID No: 40,
SEQ ID No: 56,
or
b) a variant of any of said sequences, such as a variant having at most 1, 2 or 3 amino-acid modifications, preferably substitutions, such as conservative substitutions.

In a further embodiment, the antibody comprises:
a) a VH region comprising the CDR1, 2 and 3 sequences of SEQ ID NO: 30, 31 and 32 and a VL region comprising the CDR1, 2 and 3 sequences of SEQ ID NO: 86, 87 and 88,
b) a VH region comprising the CDR1, 2 and 3 sequences of SEQ ID NO:34, 35 and 36 and a VL region comprising the CDR1, 2 and 3 sequences of SEQ ID NO:90, 91 and 92,
c) a VH region comprising the CDR1, 2 and 3 sequences of SEQ ID NO:38, 39 and 40 and a VL region comprising the CDR1, 2 and 3 sequences of SEQ ID NO:94, 95 and 96,
d) a VH region comprising the CDR1, 2 and 3 sequences of SEQ ID NO:54, 55 and 56 and a VL region comprising the CDR1, 2 and 3 sequences of SEQ ID NO:110, 11 and 112, or
e) a variant of any of said antibodies, wherein said variant preferably has at most 1, 2 or 3 amino-acid modifications, more preferably amino-acid substitutions, such as conservative amino-acid substitutions in said sequences.

In a further embodiment, the antibody comprises a VH having
a) at least 80% identity, such as at least 90%, at least 95%, or at least 98% or 100% identity to a VH region sequence selected from the group consisting of: SEQ ID NO:29, 33, 37 and 53, or
b) at most 20, such as 15, or 10, or 5, 4, 3, 2 or 1 amino-acid modifications, more preferably amino-acid substitutions, such as conservative amino-acid substitutions as compared to a VH region sequence selected from the group consisting of: SEQ ID NO:29, 33, 37 and 53.

In a further embodiment, the antibody comprises a VL having
- a) at least 80% identity, such as at least 90%, at least 95%, or at least 98% or 100% identity to a VL region sequence selected from the group consisting of: SEQ ID NO:85, 89, 93 and 109, or
- b) at most 20, such as 15, or 10, or 5, 4, 3, 2 or 1 amino-acid modifications, more preferably amino-acid substitutions, such as conservative amino-acid substitutions as compared to a VH region sequence selected from the group consisting of: SEQ ID NO:85, 89, 93 and 109.

In a further embodiment, the antibody comprises:
- a) a VH region comprising the sequence of SEQ ID NO:29 and a VL region comprising the sequence of SEQ ID NO:85,
- b) a VH region comprising the sequence of SEQ ID NO:33 and a VL region comprising the sequence of SEQ ID NO:89,
- c) a VH region comprising the sequence of SEQ ID NO:37 and a VL region comprising the sequence of SEQ ID NO:93,
- d) a VH region comprising the sequence of SEQ ID NO:53 and a VL region comprising the sequence of SEQ ID NO:109, or
- e) a variant of any of said antibodies, wherein said variant preferably has at most 1, 2 or 3 amino-acid modifications, more preferably amino-acid substitutions, such as conservative amino-acid substitutions in said sequences.

In a further embodiment, the antibody comprises antibody competes for Tissue Factor binding with an antibody comprising a VH region comprising the sequence of SEQ ID NO:41 and a VL region comprising the sequence of SEQ ID NO:97.

In a further embodiment, the antibody comprises a VH CDR3 region having
- a) the sequence as set forth in
  SEQ ID No: 4,
  SEQ ID No: 44,
  SEQ ID No: 48,
  or
- b) a variant of any of said sequences, such as a variant having at most 1, 2 or 3 amino-acid modifications, preferably substitutions, such as conservative substitutions.

In a further embodiment, the antibody comprises:
- a) a VH region comprising the CDR1, 2 and 3 sequences of SEQ ID NO:2, 3 and 4 and a VL region comprising the CDR1, 2 and 3 sequences of SEQ ID NO:58, 59 and 60,
- b) a VH region comprising the CDR1, 2 and 3 sequences of SEQ ID NO:42, 43 and 44 and a VL region comprising the CDR1, 2 and 3 sequences of SEQ ID NO:98, 99 and 100,
- c) a VH region comprising the CDR1, 2 and 3 sequences of SEQ ID NO:46, 47 and 48 and a VL region comprising the CDR1, 2 and 3 sequences of SEQ ID NO:102, 103 and 104, or
- d) a variant of any of said antibodies, wherein said variant preferably has at most 1, 2 or 3 amino-acid modifications, more preferably amino-acid substitutions, such as conservative amino-acid substitutions in said sequences.

In a further embodiment, the antibody comprises a VH having
- a) at least 80% identity, such as at least 90%, at least 95%, or at least 98% or 100% identity to a VH region sequence selected from the group consisting of: SEQ ID NO:1, 41 and 45, or
- b) at most 20, such as 15, or 10, or 5, 4, 3, 2 or 1 amino-acid modifications, more preferably amino-acid substitutions, such as conservative amino-acid substitutions as compared to a VH region sequence selected from the group consisting of: SEQ ID NO:1, 41 and 45.

In a further embodiment, the antibody comprises a VL having
- c) at least 80% identity, such as at least 90%, at least 95%, or at least 98% or 100% identity to a VL region sequence selected from the group consisting of: SEQ ID NO:57, 97 and 101, or
- d) at most 20, such as 15, or 10, or 5, 4, 3, 2 or 1 amino-acid modifications, more preferably amino-acid substitutions, such as conservative amino-acid substitutions as compared to a VH region sequence selected from the group consisting of: SEQ ID NO:57, 97 and 101.

In a further embodiment, the antibody comprises:
- a) a VH region comprising the sequence of SEQ ID NO:1 and a VL region comprising the sequence of SEQ ID NO:57,
- b) a VH region comprising the sequence of SEQ ID NO:41 and a VL region comprising the sequence of SEQ ID NO: 97,
- c) a VH region comprising the sequence of SEQ ID NO:45 and a VL region comprising the sequence of SEQ ID NO:101, or
- d) a variant of any of said antibodies, wherein said variant preferably has at most 1, 2 or 3 amino-acid modifications, more preferably amino-acid substitutions, such as conservative amino-acid substitutions in said sequences.

In an even further embodiment, the antibody of the invention has an affinity to tissue factor which is less than 5 nM, such as less than 3.5 nM, e.g. less than 2 nM when determined by the method described in Example 22 herein.

A particularly interesting group of antibodies of the invention has a binding to Tissue Factor which is characterized by a normal or high avidity and a high off-rate (kd). As demonstrated herein, such antibodies may exhibit tumor specific binding in that they bind cancerous tissue, but do not bind, or bind less to healthy tissues. Without being bound by any specific theory, it is hypothesized that this group of antibodies only binds well to cells that express high levels of TF, because the binding is only efficient if it is bivalent. Examples of these antibodies include antibody 044, 098 and 111, described herein.

Accordingly, in one embodiment, the antibody of the invention has a kd of more than $10^{-3}$ $sec^{-1}$ when determined by the affinity method described in Example 22 herein, and an avidity of less than 5 nM, such as less than 1 nM, e.g. less than 0.2 nM when determined by the avidity method described in Example 22 herein.

In another embodiment, the antibody of the invention has a kd of more than $10^{-3}$ $sec^{-1}$, when determined by the affinity method described in Example 22 herein and/or a ka of more than $5\times10^4$, $Mol^{-1}$ $sec^{-1}$ when determined by the affinity method described in Example 22 herein.

In a further embodiment, the antibody exhibits no binding to healthy tissue, in particular no binding to human glomeruli, e.g. as determined in the assay described in Example 23, but does exhibit binding to pancreatic tumors, e.g. as determined in the assay described in Example 23 herein.

In an even further embodiment, the antibody is effective in inhibiting growth of established BX-PC3 tumors when determined by the method described in Example 26 herein.

In another embodiment, the antibody of the invention has one or more of the following properties: inhibition of proliferation, inhibition of tumor angiogenesis, induction of apoptosis of tumor cells, binding to alternatively spliced Tissue Factor.

In a further embodiment, the antibody of the invention competes for Tissue Factor binding with an antibody comprising
  a) a VH region comprising the sequence of SEQ ID NO:9 and a VL region comprising the sequence of SEQ ID NO: 65,
  b) a VH region comprising the sequence of SEQ ID NO:1 and a VL region comprising the sequence of SEQ ID NO:57,
  c) a VH region comprising the sequence of SEQ ID NO:5 and a VL region comprising the sequence of SEQ ID NO:61,
  d) a VH region comprising the sequence of SEQ ID NO:13 and a VL region comprising the sequence of SEQ ID NO:69,
  e) a VH region comprising the sequence of SEQ ID NO:17 and a VL region comprising the sequence of SEQ ID NO:73,
  f) a VH region comprising the sequence of SEQ ID NO:21 and a VL region comprising the sequence of SEQ ID NO:77,
  g) a VH region comprising the sequence of SEQ ID NO:25 and a VL region comprising the sequence of SEQ ID NO:81,
  h) a VH region comprising the sequence of SEQ ID NO:29 and a VL region comprising the sequence of SEQ ID NO:85,
  i) a VH region comprising the sequence of SEQ ID NO:33 and a VL region comprising the sequence of SEQ ID NO:89,
  j) a VH region comprising the sequence of SEQ ID NO:37 and a VL region comprising the sequence of SEQ ID NO:93,
  k) a VH region comprising the sequence of SEQ ID NO:41 and a VL region comprising the sequence of SEQ ID NO: 97,
  l) a VH region comprising the sequence of SEQ ID NO:45 and a VL region comprising the sequence of SEQ ID NO:101,
  m) a VH region comprising the sequence of SEQ ID NO:49 and a VL region comprising the sequence of SEQ ID NO:105, or
  n) a VH region comprising the sequence of SEQ ID NO:53 and a VL region comprising the sequence of SEQ ID NO:109

In a further embodiment, the antibody of the invention binds to the same epitope on Tissue Factor as an antibody having:
  a) a VH region comprising the sequence of SEQ ID NO:9 and a VL region comprising the sequence of SEQ ID NO: 65,
  b) a VH region comprising the sequence of SEQ ID NO:1 and a VL region comprising the sequence of SEQ ID NO:57,
  c) a VH region comprising the sequence of SEQ ID NO:5 and a VL region comprising the sequence of SEQ ID NO:61,
  d) a VH region comprising the sequence of SEQ ID NO:13 and a VL region comprising the sequence of SEQ ID NO:69,
  e) a VH region comprising the sequence of SEQ ID NO:17 and a VL region comprising the sequence of SEQ ID NO:73,
  f) a VH region comprising the sequence of SEQ ID NO:21 and a VL region comprising the sequence of SEQ ID NO:77,
  g) a VH region comprising the sequence of SEQ ID NO:25 and a VL region comprising the sequence of SEQ ID NO:81,
  h) a VH region comprising the sequence of SEQ ID NO:29 and a VL region comprising the sequence of SEQ ID NO:85,
  i) a VH region comprising the sequence of SEQ ID NO:33 and a VL region comprising the sequence of SEQ ID NO:89,
  j) a VH region comprising the sequence of SEQ ID NO:37 and a VL region comprising the sequence of SEQ ID NO:93,
  k) a VH region comprising the sequence of SEQ ID NO:41 and a VL region comprising the sequence of SEQ ID NO: 97,
  l) a VH region comprising the sequence of SEQ ID NO:45 and a VL region comprising the sequence of SEQ ID NO:101,
  m) a VH region comprising the sequence of SEQ ID NO:49 and a VL region comprising the sequence of SEQ ID NO:105, or
  n) a VH region comprising the sequence of SEQ ID NO:53 and a VL region comprising the sequence of SEQ ID NO:109.

In a further embodiment, the antibody of the invention comprises:
  a heavy chain variable region derived from a human germline $V_H$ sequence selected from the group consisting of: IGHV1-18*01, IGHV3-23*01, IGHV3-30*01, IGHV3-33*01, IGHV3-33*03, IGHV1-69*02, IGHV1-69*04 and IGHV5-51*01 and/or
  a light chain variable region derived from a human germline VK sequence selected from the group consisting of: IGKV3-20*01, IGKV1-13*02, IGKV3-11*01, and IGKV1D-16*01.

In a further aspect, the invention relates to a monoclonal anti-TF antibody comprising a VH region having the sequence as set forth in seq id no 9, 1, 5, 13, 17, 21, 25, 29, 33, 37, 41, 45, 49 or 53, or a variant of any of said sequences, such as a variant having at most 25 amino acid modifications, such as 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions.

The variant of the sequence as set forth in seq id no 9, 1, 5, 13, 17, 21, 25, 29, 33, 37, 41, 45, 49 or 53 may have at least 80% identity to any of said sequences, such as at least 85% identity or 90% identity or 95% identity, such as 96% identity or 97% identity or 98% identity or 99% identity.

In an aspect of the invention the isolated monoclonal anti-TF antibody comprises a VL sequence as set forth in SEQ ID NO: 65, 57, 61, 69, 73, 77, 81, 85, 89, 93, 97, 101, or 105 or a variant of any of said sequences, such as a variant having at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions.

The variant of the sequence as set forth in seq id no 65, 57, 61, 69, 73, 77, 81, 85, 89, 93, 97, 101, or 105 may have at least 80% identity to any of said sequences, such as at least 85% identity or 90% identity or 95% identity, such as 96% identity or 97% identity or 98% identity or 99% identity.

In another embodiment, the antibody comprises
a) a VL region having the sequence selected from the group consisting of SEQ ID No: 65, 57, 61, 69, 73, 77, 81, 85, 89, 93, 97, 101, or 105 and a VH region having a sequence selected from the group consisting of SEQ ID No: 9, 1, 5, 13, 17, 21, 25, 29, 33, 37, 41, 45, 49 or 53,
b) a variant of any of the above, wherein said variant preferably only has conservative substitutions in said sequences.

In a preferred embodiment the antibody comprises a VL region having the sequence as set forth in SEQ ID No: 65 and a VH region having the sequence as set forth SEQ ID No: 9, or a variant of any of the two sequences, the variants having either
a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
b) at least 80% identity to SEQ ID NO: 9 or SEQ ID NO: 65 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 57 and a VH region having the sequence as set forth SEQ ID No: 1, or a variant of any of the two sequences, the variants having either
a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
b) at least 80% identity to SEQ ID NO: 1 or SEQ ID NO: 57 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 61 and a VH region having the sequence as set forth SEQ ID No: 5, or a variant of any of the two sequences, the variants having either
a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
b) at least 80% identity to SEQ ID NO: 5 or SEQ ID NO: 61 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 69 and a VH region having the sequence as set forth SEQ ID No: 13, or a variant of any of the two sequences, the variants having either
a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
b) at least 80% identity to SEQ ID NO: 13 or SEQ ID NO: 69 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 73 and a VH region having the sequence as set forth SEQ ID No: 17, or a variant of any of the two sequences, the variants having either
a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
b) at least 80% identity to SEQ ID NO: 17 or SEQ ID NO: 73 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 77 and a VH region having the sequence as set forth SEQ ID No: 21, or a variant of any of the two sequences, the variants having either
a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
b) at least 80% identity to SEQ ID NO: 21 or SEQ ID NO: 77 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 81 and a VH region having the sequence as set forth SEQ ID No: 25, or a variant of any of the two sequences, the variants having either
a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
b) at least 80% identity to SEQ ID NO: 25 or SEQ ID NO: 81 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 85 and a VH region having the sequence as set forth SEQ ID No: 29, or a variant of any of the two sequences, the variants having either
a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
b) at least 80% identity to SEQ ID NO: 29 or SEQ ID NO: 85 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 89 and a VH region having the sequence as set forth SEQ ID No: 33, or a variant of any of the two sequences, the variants having either
a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
b) at least 80% identity to SEQ ID NO: 33 or SEQ ID NO: 89 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 93 and a VH region having the sequence as set forth SEQ ID No: 37, or a variant of any of the two sequences, the variants having either
 a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
 b) at least 80% identity to SEQ ID NO: 37 or SEQ ID NO: 93 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 97 and a VH region having the sequence as set forth SEQ ID No: 41, or a variant of any of the two sequences, the variants having either
 a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
 b) at least 80% identity to SEQ ID NO: 41 or SEQ ID NO: 97 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 101 and a VH region having the sequence as set forth SEQ ID No: 45, or a variant of any of the two sequences, the variants having either
 a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
 b) at least 80% identity to SEQ ID NO: 45 or SEQ ID NO: 101 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 105 and a VH region having the sequence as set forth SEQ ID No: 49, or a variant of any of the two sequences, the variants having either
 a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
 b) at least 80% identity to SEQ ID NO: 49 or SEQ ID NO: 105 respectively, such as at least 85% identity or 90% identity or 95% identity, such as 96% identity or 97% identity or 98% identity or 99% identity.

In another preferred embodiment the antibody comprises a VL region having the sequence as set forth in SEQ ID No: 109 and a VH region having the sequence as set forth SEQ ID No: 53, or a variant of any of the two sequences, the variants having either
 a) at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions, or
 b) at least 80% identity to SEQ ID NO: 53 or SEQ ID NO: 109 respectively, such as at least 85% identity or 90% identity or 95% identity, such as 96% identity or 97% identity or 98% identity or 99% identity.

Monoclonal antibodies of the present invention may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, rabbits, dogs, primates, etc.

In one embodiment, the antibody of the invention is a human antibody. Human monoclonal antibodies directed against tissue factor may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy variable and constant (μ and γ) and light variable and constant (κ) chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci. 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. No. 5,545,806, U.S. Pat. No. 5,569,825, U.S. Pat. No. 5,625,126, U.S. Pat. No. 5,633,425, U.S. Pat. No. 5,789,650, U.S. Pat. No. 5,877,397, U.S. Pat. No. 5,661,016, U.S. Pat. No. 5,814,318, U.S. Pat. No. 5,874,299, U.S. Pat. No. 5,770,429, U.S. Pat. No. 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424).

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

Splenocytes from these transgenic mice may be used to generate hybridomas that secrete human monoclonal antibodies according to well known techniques. Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. No. 5,827,690, U.S. Pat. No. 5,756,687, U.S. Pat. No. 5,750,172 and U.S. Pat. No. 5,741,957.

Further, human antibodies of the present invention or antibodies of the present invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

The antibody of the invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of an anti-TF antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1,κ.

In one embodiment, the antibody of the invention is a full-length antibody, preferably an IgG1 antibody, in particular an IgG1,κ antibody. In another embodiment, the antibody of the invention is an antibody fragment or a single-chain antibody.

Antibodies fragments may e.g. be obtained by fragmentation using conventional techniques, and the fragments screened for utility in the same manner as described herein for whole antibodies. For example, $F(ab')_2$ fragments may be generated by treating antibody with pepsin. The resulting $F(ab')_2$ fragment may be treated to reduce disulfide bridges to produce Fab' fragments. Fab fragments may be obtained by treating an IgG antibody with papain; Fab' fragments may be obtained with pepsin digestion of IgG antibody. An F(ab') fragment may also be produced by binding Fab' described below via a thioether bond or a disulfide bond. A Fab' fragment is an antibody fragment obtained by cutting a disulfide bond of the hinge region of the $F(ab')_2$. A Fab' fragment may be obtained by treating an $F(ab')_2$ fragment with a reducing agent, such as dithiothreitol. Antibody fragment may also be generated by expression of nucleic acids encoding such fragments in recombinant cells (see for instance Evans et al., J. Immunol. Meth. 184, 123-38 (1995)). For example, a chimeric gene encoding a portion of an $F(ab')_2$ fragment could include DNA sequences encoding the $C_H1$ domain and hinge region of the H chain, followed by a translational stop codon to yield such a truncated antibody fragment molecule.

In one embodiment, the anti-TF antibody is a monovalent antibody, preferably a monovalent antibody as described in WO2007059782 (Genmab) (incorporated herein by reference) having a deletion of the hinge region. Accordingly, in one embodiment, the antibody is a monovalent antibody, wherein said anti-TF antibody is constructed by a method comprising:

i) providing a nucleic acid construct encoding the light chain of said monovalent antibody, said construct comprising a nucleotide sequence encoding the VL region of a selected antigen specific anti-TF antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being;

ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together;
iii) providing a cell expression system for producing said monovalent antibody;
iv) producing said monovalent antibody by co-expressing the nucleic acid constructs of (i) and (ii) in cells of the cell expression system of (iii).

Similarly, in one embodiment, the anti-TF antibody is a monovalent antibody, which comprises
(i) a variable region of an antibody of the invention as described herein or an antigen binding part of the said region, and
(ii) a $C_H$ region of an immunoglobulin or a fragment thereof comprising the $C_H2$ and $C_H3$ regions, wherein the $C_H$ region or fragment thereof has been modified such that the region corresponding to the hinge region and, if the immunoglobulin is not an IgG4 subtype, other regions of the $C_H$ region, such as the $C_H3$ region, do not comprise any amino acid residues, which are capable of forming disulfide bonds with an identical $C_H$ region or other covalent or stable non-covalent inter-heavy chain bonds with an identical $C_H$ region in the presence of polyclonal human IgG.

In a further embodiment, the heavy chain of the monovalent anti-TF antibody has been modified such that the entire hinge has been deleted.

In a further embodiment, said monovalent antibody is of the IgG4 subtype (see SEQ ID NO: 114, a hinge-less variant of SEQ ID NO:113), but the $C_H3$ region has been modified so that one or more of the following amino acid substitutions have been made: Thr (T) in position 234 has been replaced by Ala (A); Leu (L) in position 236 has been replaced by Ala (A); Leu (L) in position 236 has been replaced by Val (V); Phe (F) in position 273 has been replaced by Ala (A); Phe (F) in position 273 has been replaced by Leu (L); Tyr (Y) in position 275 has been replaced by Ala (A).

In another further embodiment, the sequence of said monovalent antibody has been modified so that it does not comprise any acceptor sites for N-linked glycosylation.

Anti-TF antibodies of the invention also include single chain antibodies. Single chain antibodies are peptides in which the heavy and light chain Fv regions are connected. In one embodiment, the present invention provides a single-chain Fv (scFv) wherein the heavy and light chains in the Fv of an anti-TF antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used.

In one embodiment, the anti-TF antibody of the invention is an effector-function-deficient antibody. Such antibodies are particularly useful when the antibody is for use in stimulation of the immune system through blocking of the inhibitory effects of TF. For such applications, it may be advantages that the antibody has no effector functions, such as ADCC, as they may lead to undesired cytotoxicity.

In one embodiment, the effector-function-deficient anti-TF antibody is a stabilized IgG4 antibody. Examples of suitable stabilized IgG4 antibodies are antibodies, wherein arginine at position 409 in a heavy chain constant region of human IgG4, which is indicated in the EU index as in Kabat et al., is substituted with lysine, threonine, methionine, or leucine, preferably lysine (described in WO2006033386 (Kirin)) and/or wherein the hinge region comprises a Cys-Pro-Pro-Cys (SEQ ID NO: 133) sequence.

In a further embodiment, the stabilized IgG4 anti-TF antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions, but does not comprise a Cys-Pro-Pro-Cys (SEQ ID NO: 133) sequence in the hinge region. Preferably, said antibody comprises a Lys or Ala residue at the position corresponding to 409 or the CH3 region of the antibody has been replaced by the CH3 region of human IgG1, of human IgG2 or of human IgG3.

In an even further embodiment, the stabilized IgG4 anti-TF antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions and wherein said antibody comprises a Cys-Pro-Pro-Cys sequence (SEQ ID NO: 133) in the hinge region. Preferably, said antibody comprises a Lys or Ala residue at the position corresponding to 409 or the CH3 region of the antibody has been replaced by the CH3 region of human IgG1, of human IgG2 or of human IgG3.

In a further embodiment, the effector-function-deficient anti-TF antibody is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J. Immunol. 177(2):1129-1138 (2006) and Hezareh M, J Virol.; 75(24):12161-12168 (2001).

In a further embodiment, the antibody of the invention is conjugated to another moiety, such as a cytotoxic moiety, a radioisotope or a drug. Such antibodies may be produced by chemically conjugating the other moiety to the N-terminal side or C-terminal side of the anti-TF antibody or fragment thereof (e.g., an anti-TF antibody H chain, L chain, or anti-TF specific/selective fragment thereof) (see, e.g., Antibody Engineering Handbook, edited by Osamu Kanemitsu, published by Chijin Shokan (1994)). Such conjugated antibody derivatives may also be generated by conjugation at internal residues or sugars, where appropriate.

In general, anti-TF antibodies described herein may be modified by inclusion of any suitable number of such modified amino acids and/or associations with such conjugated substituents. Suitability in this context is generally determined by the ability to at least substantially retain TF selectivity and/or specificity associated with the non-derivatized parent anti-TF antibody. The inclusion of one or more modified amino acids may be advantageous in, for example, increasing polypeptide serum half-life, reducing polypeptide antigenicity, or increasing polypeptide storage stability. Amino acid(s) are modified, for example, co-translationally or post-translationally during recombinant production (e.g., N-linked glycosylation at N—X—S/T motifs during expression in mammalian cells) or modified by synthetic means.

Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On Cd-Rom, Humana Press, Towata, N.J. The modified amino acid may for instance be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

Anti-TF antibodies may also be chemically modified by covalent conjugation to a polymer to for instance increase their circulating half-life. Exemplary polymers, and methods to attach them to peptides, are illustrated in for instance U.S. Pat. No. 4,766,106, U.S. Pat. No. 4,179,337, U.S. Pat. No. 4,495,285 and U.S. Pat. No. 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000 g/mol).

In one embodiment, the present invention provides an anti-TF antibody that is conjugated to a second molecule that is selected from a radionuclide, an enzyme, an enzyme substrate, a cofactor, a fluorescent marker, a chemiluminescent marker, a peptide tag, or a magnetic particle. In one embodiment, an anti-TF antibody may be conjugated to one or more antibody fragments, nucleic acids (oligonucleotides), nucleases, hormones, immunomodulators, chelators, boron compounds, photoactive agents, dyes, and the like. These and other suitable agents may be coupled either directly or indirectly to an anti-TF antibody of the present invention. One example of indirect coupling of a second agent is coupling by a spacer moiety. These spacers, in turn, may be either insoluble or soluble (see for instance Diener et al., Science 231, 148 (1986)) and may be selected to enable drug release from the anti-TF antibody at a target site and/or under particular conditions. Additional examples of agents that may be coupled to an anti-TF antibody include lectins and fluorescent peptides.

In one embodiment, anti-TF antibodies comprising one or more radiolabeled amino acids are provided. A radiolabeled anti-TF antibody may be used for both diagnostic and therapeutic purposes (conjugation to radiolabeled molecules is another possible feature). Nonlimiting examples of labels for polypeptides include, but are not limited to 3H, 14C, 15N, 35S, 90Y, 99Tc, and 125I, 131I, and 186Re. Methods for preparing radiolabeled amino acids and related peptide derivatives are known in the art (see for instance Junghans et al., in Cancer Chemotherapy and Biotherapy 655-686 (2d edition, Chafner and Longo, eds., Lippincott Raven (1996)) and U.S. Pat. No. 4,681,581, U.S. Pat. No. 4,735,210, U.S. Pat. No. 5,101,827, U.S. Pat. No. 5,102,990 (U.S. RE35,500), U.S. Pat. No. 5,648,471 and U.S. Pat. No. 5,697,902. For example, a radioisotope may be conjugated by a chloramine T method.

In one embodiment, an anti-TF antibody of the invention comprises a conjugated nucleic acid or nucleic acid-associated molecule. In one such facet of the present invention, the conjugated nucleic acid is a cytotoxic ribonuclease. In one embodiment, the conjugated nucleic acid is an antisense nucleic acid (for instance a S100A10 targeted antisense molecule, which may also be an independent component in a combination composition or combination administration method of the present invention—see for instance Zhang et al., J Biol Chem. 279(3), 2053-62 (2004)). In one embodiment, the conjugated nucleic acid is an inhibitory RNA molecule (e.g., a siRNA molecule). In one embodiment, the conjugated nucleic acid is an immunostimulatory nucleic acid (e.g., an immunostimulatory CpG motif-containing DNA molecule). In one embodiment, the conjugated nucleic acid is an expression cassette coding for expression of a tumor suppressor gene, anti-cancer vaccine, anti-cancer cytokine, or apoptotic agent. Such derivatives also may comprise conjugation of a nucleic acid coding for expression of one or more cytotoxic proteins, such as plant and bacterial toxins.

In one embodiment, an anti-TF antibody is conjugated to a functional nucleic acid molecule. Functional nucleic acids include antisense molecules, interfering nucleic acid molecules (e.g., siRNA molecules), aptamers, ribozymes, triplex forming molecules, and external guide sequences. The functional nucleic acid molecules may act as effectors, inhibitors, modulators, and stimulators of a specific activity possessed by a target molecule, or the functional nucleic acid molecules may possess a de novo activity independent of any other molecules.

In another embodiment, an anti-TF antibody of the invention is conjugated to an aptamer.

In another embodiment, the present invention provides an anti-TF antibody which is conjugated to a ribozyme.

Any method known in the art for conjugating the anti-TF antibody to the conjugated molecule(s), such as those described above, may be employed, including those methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Numerous types of cytotoxic compounds may be joined to proteins through the use of a reactive group on the cytotoxic compound or through the use of a cross-linking agent. A common reactive group that will form a stable covalent bond in vivo with an amine is isothiocyanate (Means et al., Chemical modifications of proteins (Holden-Day, San Francisco 1971) pp. 105-110). This group preferentially reacts with the ϵ-amine group of lysine. Maleimide is a commonly used reactive group to form a stable in vivo covalent bond with the sulfhydryl group on cysteine (Ji., Methods Enzymol 91, 580-609 (1983)). Monoclonal antibodies typically are incapable of forming covalent bonds with radiometal ions, but they may be attached to the antibody indirectly through the use of chelating agents that are covalently linked to the antibodies. Chelating agents may be attached through amines (Meares et al., Anal. Biochem. 142, 68-78 (1984)) and sulfhydral groups (Koyama, Chem. Abstr. 120, 217262t (1994)) of amino acid residues and also through carbohydrate groups (Rodwell et al., PNAS USA 83, 2632-2636 (1986), Quadri et al., Nucl. Med. Biol. 20, 559-570 (1993)). Since these chelating agents contain two types of functional groups, one to bind metal ions and the other to joining the chelate to the antibody, they are commonly referred as bifunctional chelating agents (Sundberg et al., Nature 250, 587-588 (1974)).

In one embodiment, the present invention provides an anti-TF antibody, such as a human anti-TF antibody, conjugated to a therapeutic moiety, such as a cytotoxin, a chemotherapeutic drug, an immunosuppressant, or a radioisotope. Such conjugates are referred to herein as "immunoconjugates". Immunoconjugates which include one or more cytotoxins are referred to as "immunotoxins".

A cytotoxin or cytotoxic agent includes any agent that is detrimental to (e.g., kills) cells. For a description of these classes of drugs which are well known in the art, and their mechanisms of action, see Goodman et al., Goodman and Gilman's The Pharmacological Basis Of Therapeutics, 8th Ed., Macmillan Publishing Co., 1990. Additional techniques relevant to the preparation of antibody immunotoxins are provided in for instance Vitetta, Immunol. Today 14, 252 (1993) and U.S. Pat. No. 5,194,594.

Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, sapaonaria officinalis inhibitor, gelonin, mitogellin, restrictocin, phenomycin, and enomycin toxins. Other suitable conjugated molecules include ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Therapeutic agents, which may be administered in combination with a an anti-TF antibody of the present invention as described elsewhere herein, may also be candidates for therapeutic moieties useful for conjugation to an anti-TF antibody of the present invention.

In one embodiment, the anti-TF antibody of the present invention is attached to a chelator linker, e.g. tiuxetan, which allows for the antibody to be conjugated to a radioisotope.

In a further aspect, the invention relates to a bispecific molecule comprising an anti-TF antibody of the invention as described herein above and a second binding specificity such as a binding specificity for a human effector cell, a human Fc receptor or a T cell receptor. Or a binding specificity for another epitope of TF.

Bispecific molecules of the present invention may further include a third binding specificity, in addition to an anti-TF binding specificity and a binding specificity for a human effector cell, a human Fc receptor or a T cell receptor.

Exemplary bispecific antibody molecules of the invention comprise (i) two antibodies one with a specificity to TF and another to a second target that are conjugated together, (ii) a single antibody that has one chain specific to TF and a second chain specific to a second molecule, and (iii) a single chain antibody that has specificity to TF and a second molecule. Typically, the second target/second molecule is a molecule other than TF. In one embodiment, the second molecule is a cancer antigen/tumor-associated antigen such as carcinoembryonic antigen (CEA), prostate specific antigen (PSA), RAGE (renal antigen), α-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, C-myc, Mart1, MelanA, MUM-1, MUM-2, MUM-3, HLA-B7, and Ep-CAM. In one embodiment, the second molecule is a cancer-associated integrin, such as α5β3 integrin. In one embodiment, the second molecule is an angiogenic factor or other cancer-associated growth factor, such as a vascular endothelial growth factor (VEGF), a fibroblast growth factor (FGF), epidermal growth factor (EGF), epidermal growth factor receptor (EGFR), angiogenin, and receptors thereof, particularly receptors associated with cancer progression (for instance one of the HER1-HER4 receptors, c-met or RON). Other cancer progression-associated proteins discussed herein may also be suitable second molecules.

In one embodiment, a bispecific antibody of the present invention is a diabody. Bispecific antibodies also include cross-linked or "heteroconjugate" antibodies. For example, one of the antibodies in a heteroconjugate may be coupled to avidin and the other to biotin. Such antibodies have, for example, been proposed to target immune system cells to unwanted cells (see for instance U.S. Pat. No. 4,676,980). Heteroconjugate antibodies may be made using any convenient cross-linking methods.

In a further aspect, the invention relates to an expression vector encoding an antibody of the invention.

In one embodiment, the expression vector of the invention comprises a nucleotide sequence encoding one or more of the amino acid sequences selected from the group consisting of: SEQ ID NO: 1-112.

In another particular embodiment, the expression vector of the invention comprises a nucleotide sequence encoding one or more of the VH amino acid sequences selected from the group consisting of: SEQ ID NO: 9, 1, 5, 13, 17, 21, 25, 29, 33, 37, 41, 45, 49 and 53.

In a particular embodiment, the expression vector of the invention comprises a nucleotide sequence encoding one or more of the VH CDR3 amino acid sequences selected from the group consisting of: SEQ ID NO 4, 8, 12, 16, 20, 24, 28, 32, 36, 40, 44, 48, 52 and 56.

In another particular embodiment, the expression vector of the invention comprises a nucleotide sequence encoding one or more of the VL amino acid sequences selected from the group consisting of: SEQ ID NO: 65, 57, 61, 69, 73, 77, 81, 85, 89, 93, 97, 101 and 105.

In another embodiment, the expression vector of the invention comprises a nucleotide sequence encoding one or more of the VL CDR3 amino acid sequences selected from the group consisting of: SEQ ID NO: 60, 64, 68, 72, 76, 80, 84, 88, 92, 96, 100, 104 and 108.

In a particular embodiment the expression vector of the invention comprises a nucleotide sequence encoding variants of one or more of the above amino acid sequences, said variants having at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions or at least 80% identity to any of said sequences, such as at least 85% identity or 90% identity or 95% identity, such as 96% identity or 97% identity or 98% identity or 99% identity to any of the afore mentioned amino acid sequences.

In a further embodiment, the expression vector further comprises a nucleotide sequence encoding the constant region of a light chain, a heavy chain or both light and heavy chains of an antibody, e.g. a human antibody.

Such expression vectors may be used for recombinant production of antibodies of the invention.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-TF antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC19/18, or pUC118/119, a "midge" minimally-sized nucleic acid vector (as described in for instance Schakowski et al., Mol Ther 3, 793-800 (2001)), or as a precipitated nucleic acid vector construct, such as a CaPO4-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. No. 5,589,466 and U.S. Pat. No. 5,973,972).

In one embodiment, the vector is suitable for expression of the anti-TF antibody in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley Inter-Science New York (1987), and Grant et al., Methods in Enzymol 153, 516-544 (1987)).

A nucleic acid and/or vector may also comprises a nucleic acid sequence encoding a secretion/localization sequence, which can target a polypeptide, such as a nascent polypeptide chain, to the periplasmic space or into cell culture media. Such sequences are known in the art, and include secretion leader or signal peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

In an expression vector of the invention, anti-TF antibody-encoding nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in E. coli, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In one embodiment, the anti-TF-antibody-encoding expression vector may be positioned in and/or delivered to the host cell or host animal via a viral vector.

In an even further aspect, the invention relates to a recombinant eukaryotic or prokaryotic host cell, such as a transfectoma, which produces an antibody of the invention as defined herein or a bispecific molecule of the invention as defined herein. Examples of host cells include yeast, bacterial, and mammalian cells, such as CHO or HEK cells. For example, in one embodiment, the present invention provides a cell comprising a nucleic acid stably integrated into the cellular genome that comprises a sequence coding for expression of an anti-TF antibody of the present invention. In another embodiment, the present invention provides a cell comprising a non-integrated nucleic acid, such as a plasmid, cosmid, phagemid, or linear expression element, which comprises a sequence coding for expression of an anti-TF antibody of the invention.

In a further aspect, the invention relates to a hybridoma which produces an antibody of the invention as defined herein. In an even further aspect, the invention relates to a transgenic non-human animal comprising nucleic acids encoding a human heavy chain and a human light chain, wherein the animal or plant produces an antibody of the invention of the invention. Generation of such hybridomas and transgenic animals has been described above.

In a further aspect, the invention relates to a method for producing an anti-TF antibody of the invention, said method comprising the steps of a) culturing a hybridoma or a host cell of the invention as described herein above, and b) purifying the antibody of the invention from the culture media.

In a further main aspect, the invention relates to an anti-TF antibody as defined herein or a bispecific molecule as defined herein for use as a medicament.

In an even further aspect, the invention relates to a pharmaceutical composition comprising:
 an anti-TF antibody as defined herein or a bispecific molecule as defined herein, and
 a pharmaceutically-acceptable carrier.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding.

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

It has been reported that in cancer cells, such as human colorectal cancer cells, TF expression is under control of 2 major transforming events driving disease progression (activation of K-ras oncogene and inactivation of the p53 tumor suppressor), in a manner dependent on MEK/mitogen-activated protein kinase (MAPK) and phosphatidylinositol 3'-kinase (PI3K) (Yu et al. (2005) Blood 105:1734.

Cancer cells overexpressing TF may be particularly good targets for anti-TF antibodies of the invention, since more antibodies may be bound per cell. Thus, in one embodiment, a cancer patient to be treated with an anti-TF antibody of the invention is a patient, e.g. a pancreatic cancer, lung cancer or colorectal cancer patient who has been diagnosed to have one or more mutations in K-Ras and/or one or more mutations in p53 in their tumor cells.

In an alternative embodiment, the patient to be treated with an anti-TF antibody of the invention is a patient, e.g. a pancreatic cancer, lung cancer or colorectal cancer patient, who does not have a mutation in K-Ras. Without being bound by any specific theory, it is possible that some tumor cells having K-Ras activation are less susceptible to anti-TF antibody treatment, because the effects of anti-TF antibodies on intracellular signaling mechanisms may be less effective in cells in which K-Ras is activated.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a compound of the present invention in vivo and in vitro are well known in the art and may be selected by those of ordinary skill in the art.

In one embodiment, a pharmaceutical composition of the present invention is administered parenterally.

The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or nonaqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

The pharmaceutical composition of the present invention may contain one compound of the present invention or a combination of compounds of the present invention.

As described above, in another aspect, the invention relates to the antibody of the invention as defined herein or a bispecific molecule of the invention as defined herein for use as a medicament.

The anti-TF antibodies of the invention may be used for a number of purposes. In particular, the antibodies of the invention may be used for the treatment of various forms of cancer. In one aspect the anti-TF monoclonal antibodies of the invention are used for the treatment of various solid cancer types such as: tumors of the central nervous system, head and neck cancer, lung cancer (such as non-small cell lung cancer), breast cancer, esophageal cancer, stomach cancer, liver and biliary cancer, pancreatic cancer, colorectal cancer, bladder cancer, kidney cancer, prostate cancer, endometrial cancer, ovarian cancer, malignant melanoma, sarcoma (soft tissue eg. bone and muscle), tumors of unknown primary origin (i.e. unknown primarys), leukemia, bone marrow cancer (such as multiple myeloma) acute lymphoblastic leukemia, chronic lymphoblastic leukemia and non-Hodgkin lymphoma, skin cancer, glioma, cancer of the brain, uterus, and rectum.

Further autoimmune inflammation, such as myopathies or multiple sclerose may be targeted with the anti-TF monoclonal antibodies of the present invention.

The anti-TF monoclonal antibodies of the present invention may also be useful for the treatment of haemostatis.

Cancer related hemostatic disorders may also be targeted with the present intervention.

Further diseases with inflammation, such as myopathies, Rheumatoid Arthritis, osteoarthritis, ankylosing spondylitis, gout, spondylarthropathris, ankylosing spondylitis, Reiter's syndrome, psoriatic arthropathy, enterapathric spondylitis, juvenile arthropathy, reactive arthropathy, infectious or post-infectious arthritis, tuberculous arthritis, viral arthritis, fungal arthritis, syphilitic arthritis, glomerulonephritis, end stage renal disease, systemic lupus erythematosus, mb. Crohn, ulcerative colitis, inflammatory bowel disease, cystic fibrosis, chronic obstructive pulmonary disease (COPD), astma, allergic astma, bronchitis, acute bronchiolitis, chronic bronchiolitis, idiopathic pulmonary fibrosis, or multiple sclerose may be targeted with the anti-TF monoclonal antibodies of the present invention.

The anti-TF monoclonal antibodies of the present invention may also be useful for the treatment of haemostatis.

Cancer related hemostatic disorders may also be targeted with the present intervention.

Also vascular diseases such as vascular restenosis, myocardial vascular disease, cerebral vascular disease, retinopathia and macular degeneration, including but not limited to wet AMD can be treated with anti-TF monoclonal antibodies.

The anti-TF monoclonal antibodies of the present invention may also be useful for the treatment of patients with cardiovascular risk, such as atherosclerosis, hypertension, diabetis, dyslipidemia, and acute coronary syndrome, including but not limited to Acute Myocardial Infarct, stroke.

The anti-TF monoclonal antibodies of the present invention may also be useful for inhibition of thrombosis, such as DVT, renal embolism, lung embolism, arterial thrombosis, or to treat thrombosis occurring following arteriel surgical, peripheral vascular bypass grafts or coronary artery bypass grafts, arterio-venous shunts, removal of an implementation, such as a stent or catheter The anti-TF monoclonal antibodies of the present invention may also be useful for inhibition of renal ischemic reperfusion injury The anti-TF monoclonal antibodies of the present invention may also be useful for treatment of hyperlipoproteineimia, hyperparathyroidism, The anti-TF monoclonal antibodies of the present invention may also be useful for treatment of vasculitis, ANCA-positive vasculitis, Behcet's disease The anti-TF monoclonal antibodies of the present invention may also be useful for blocking traume-induced respiratory failure, such as Acute Respitory Distress Syndrome, Acute lung Injury.

The anti-TF monoclonal antibodies of the present invention may also be useful for blocking infection-induced organ dysfunction, such as renal failure, Acute Respiratory Distress Syndrome, Acute Lung Injury The anti-TF monoclonal antibodies of the present invention may also be useful to treat various thromboembolic disorders such as those arising from angioplasty, myocardial infarction, unstable angina and coronary artery stenoses.

The anti-TF monoclonal antibodies of the present invention may also be useful in a prophylactic setting to treat TF-mediated complications to systemic infections, such as sepsis or pneumonia.

The anti-TF monoclonal antibodies of the present invention may also be useful as prophylactic treatment of patients with atherosclerotic vessels at risk for thrombosis The anti-TF monoclonal antibodies of the present invention may also be useful for treatment of Graft-versus-host disease.

The anti-TF monoclonal antibodies of the present invention may also be useful for increasing beta cell engraftment in islet transplantation, to prevent cardiac allograft vasculopathy (CAV), to prevent acute graft rejection The anti-TF monoclonal antibodies of the present invention may also be useful for treatment of diseases where circulating tissue-factor exposing microparticles are present, such as but not limited to vascular thrombosis, type II diabetis, AMI, pulmonary arterial hypertension Similarly, the invention relates to a method for inhibiting growth and/or proliferation of a tumor cell expressing TF, comprising administration, to an individual in need thereof, of an antibody or a bispecific molecule of the invention. In one embodiment, said tumor cell is involved in cancer, such as prostate cancer, lung cancer (such as non-small cell lung cancer), breast cancer, colorectal cancer (such as metastatic colorectal cancer), pancreatic cancer, endometrial cancer, ovarian cancer, cutaneous melanoma, leukemia bone marrow cancer (such as multiple myeloma), acute lymphoblastic leukemia, chronic lymphoblastic leukemia and non-Hodgkin lymphoma, skin cancer, prostate cancer, glioma, cancer of the brain, kidneys, uterus, bladder, and rectum.

Also, the invention relates to the use of a monoclonal antibody that binds to human TF for the preparation of a medicament for the treatment of cancer, such as one of the specific cancer indications mentioned above.

In an embodiment selection of patients to be treated with anti-TF antibody is based on the level of tissue factor (TF) in their urine and/or blood. In a particular embodiment the patient to be treated has a relatively high level of TF in urine and/or blood. For example, the patient to be treated may have a TF level in urine of more than 20 ng/ml, such as more than 40 ng/ml, e.g. more than 100 ng/ml, such as more than 200 ng/ml. Alternatively, or in addition, the TF level in serum of the patients may be more than 100 pg/ml, such as more than 200 pg/ml. This may e.g. be determined using an ELISA.

In a further embodiment of the methods of treatment of the present invention, the efficacy of the treatment is being monitored during the therapy, e.g. at predefined points in time. In one embodiment, the efficacy may be monitored by measuring the level of TF in urine or blood, for example by ELISA. In another embodiment, the efficacy may be determined by visualization of the disease area, e.g. by performing one or more PET-CT scans, for example using a labeled anti-TF antibody, such as a labeled anti-TF antibody of the present invention. Furthermore, labeled anti-TF antibodies, such as labeled anti-TF antibodies of the invention, could be used to detect TF-producing tumors e.g. using a PET-CT scan.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the anti-TF antibodies depend on the disease or condition to be treated and may be determined by the persons skilled in the art. An exemplary, non-limiting range for a therapeutically effective amount of a compound of the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg.

A physician or veterinarian having ordinary skill in the art may readily determine and prescribe the effective amount of the pharmaceutical composition required. For example, the physician or veterinarian could start doses of the anti-TF antibody employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

In one embodiment, the anti-TF antibodies may be administered by infusion in a weekly dosage of from 10 to 500 mg/m$^2$, such as of from 200 to 400 mg/m$^2$. Such administration may be repeated, e.g., 1 to 8 times, such as 3 to 5 times. The administration may be performed by continuous infusion over a period of from 2 to 24 hours, such as of from 2 to 12 hours.

In one embodiment, the anti-TF antibodies may be administered by slow continuous infusion over a long period, such as more than 24 hours, in order to reduce toxic side effects.

In one embodiment the anti-TF antibodies may be administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the anti-TF antibodies of the present invention.

In one embodiment, the anti-TF antibodies may be administered by maintenance therapy, such as, e.g., once a week for a period of 6 months or more.

In one embodiment, the anti-TF antibodies may be administered by a regimen including one infusion of an anti-TF antibody of the present invention followed by an infusion of an anti-TF antibody of the present invention conjugated to a radioisotope. The regimen may be repeated, e.g., 7 to 9 days later.

As non-limiting examples, treatment according to the present invention may be provided as a daily dosage of a compound of the present invention in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

An "effective amount" for tumor therapy may also be measured by its ability to stabilize the progression of disease. The ability of a compound to inhibit cancer may be evaluated in an animal model system predictive of efficacy in human tumors. Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

An anti-TF antibody may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

Anti-TF antibodies may also be administered in combination therapy, i.e., combined with other therapeutic agents relevant for the disease or condition to be treated. Accordingly, in one embodiment, the antibody-containing medicament is for combination with one or more further therapeutic agent, such as a cytotoxic, chemotherapeutic or anti-angiogenic agent.

Such combined administration may be simultaneous, separate or sequential. For simultaneous administration the agents may be administered as one composition or as separate compositions, as appropriate. The present invention thus also provides methods for treating a disorder involving cells expressing TF as described above, which methods comprise administration of an anti-TF antibody of the present invention combined with one or more additional therapeutic agents as described below.

In one embodiment, the present invention provides a method for treating a disorder involving cells expressing TF in a subject, which method comprises administration of a therapeutically effective amount of an anti-TF antibody of the present invention and at least one chemotherapeutic agent to a subject in need thereof.

In one embodiment, the present invention provides a method for treating or preventing cancer, which method comprises administration of a therapeutically effective amount of an anti-TF antibody of the present invention and at least one chemotherapeutic agent to a subject in need thereof.

In one embodiment, the present invention provides the use of an anti-TF antibody of the present invention for the preparation of a pharmaceutical composition to be administered with at least one chemotherapeutic agent for treating cancer.

In one embodiment, such a chemotherapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine, cladribine and similar agents.

In one embodiment, such a chemotherapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin, and similar agents.

In one embodiment, such a chemotherapeutic agent may be selected from an anti-mitotic agent, such as taxanes, for instance docetaxel, and paclitaxel, and vinca alkaloids, for instance vindesine, vincristine, vinblastine, and vinorelbine.

In one embodiment, such a chemotherapeutic agent may be selected from a topoisomerase inhibitor, such as topotecan or irinotecan.

In one embodiment, such a chemotherapeutic agent may be selected from a cytostatic drug, such as etoposide and teniposide.

In one embodiment, such a chemotherapeutic agent may be selected from a growth factor inhibitor, such as an inhibitor of ErbB1 (EGFR) (such as Iressa, erbitux (cetuximab), tarceva and similar agents), an inhibitor of ErbB2 (Her2/neu) (such as herceptin and similar agents) and similar agents.

In one embodiment, such a chemotherapeutic agent may be selected from a tyrosine kinase inhibitor, such as imatinib (Glivec®, Gleevec STI571), lapatinib, PTK787/ZK222584 and similar agents.

In one embodiment, the present invention provides a method for treating a disorder involving cells expressing TF in a subject, which method comprises administration of a therapeutically effective amount of an anti-TF antibody of the present invention and at least one inhibitor of angiogenesis, neovascularization, and/or other vascularization to a subject in need thereof.

Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF, bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents.

Other examples of such inhibitors of angiogenesis, neovascularization, and/or other vascularization are anti-angiogenic heparin derivatives and related molecules (e.g., heperinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

In one embodiment, a therapeutic agent for use in combination with an anti-TF antibody for treating the disorders as described above may be an anti-cancer immunogen, such as a cancer antigen/tumor-associated antigen (e.g., epithelial cell adhesion molecule (EpCAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines), tumor-derived heat shock proteins, and similar agents. A number of other suitable cancer antigens/tumor-associated antigens described elsewhere herein and similar molecules known in the art may also or alternatively be used in such embodiment. Anti-cancer immunogenic peptides also include anti-idiotypic "vaccines" such as BEC2 anti-idiotypic antibodies, Mitumomab, CeaVac and related anti-idiotypic antibodies, anti-idiotypic antibody to MG7 antibody, and other anti-cancer anti-idiotypic antibodies (see for instance Birebent et al., Vaccine. 21(15), 1601-12 (2003), Li et al., Chin Med J (Engl). 114(9), 962-6 (2001), Schmitt et al., Hybridoma. 13(5), 389-96 (1994), Maloney et al., Hybridoma. 4(3), 191-209 (1985), Raychardhuri et al., J Immunol. 137(5), 1743-9 (1986), Pohl et al., Int J Cancer. 50(6), 958-67 (1992), Bohlen et al., Cytokines Mol Ther. 2(4), 231-8 (1996) and Maruyama, J Immunol Methods. 264 (1-2), 121-33 (2002)). Such anti-idiotypic Abs may optionally be conjugated to a carrier, which may be a synthetic (typically inert) molecule carrier, a protein (for instance keyhole limpet hemocyanin (KLH) (see for instance Ochi et al., Eur J Immunol. 17(11), 1645-8 (1987)), or a cell (for instance a red blood cell—see for instance Wi et al., J Immunol Methods. 122(2), 227-34 (1989)).

In one embodiment, a therapeutic agent for use in combination with an anti-TF antibody for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFα2b), IFNβ, GM-CSF, CD40L, Flt3 ligand, stem cell factor, ancestim, and TNFα. Suitable chemokines may include Glu-Leu-Arg (ELR)-negative chemokines such as IP-10, MCP-3, MIG, and SDF-1a from the human CXC and C-C chemokine families. Suitable cytokines include cytokine derivatives, cytokine variants, cytokine fragments, and cytokine fusion proteins. These and other methods or uses involving naturally occurring peptide-encoding nucleic acids herein may alternatively or additionally be performed by "gene activation" and homologous recombination gene upregulation techniques, such as are described in U.S. Pat. No. 5,968,502, U.S. Pat. No. 6,063,630 and U.S. Pat. No. 6,187,305 and EP 0505500.

In one embodiment, a therapeutic agent for use in combination with an anti-TF antibody for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. No. 6,440,735 and U.S. Pat. No. 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In one embodiment, a therapeutic agent for use in combination with an anti-TF antibody for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane), a hormone inhibitor (such as octreotide/sandostatin) and similar agents.

In one embodiment, a therapeutic agent for use in combination with an anti-TF antibody for treating the disorders as described above may be an anti-anergic agent (for instance small molecule compounds, proteins, glycoproteins, or antibodies that break tolerance to tumor and cancer antigens). Examples of such compounds are molecules that block the activity of CTLA-4, such as MDX-010 (ipilimumab) (Phan et al., PNAS USA 100, 8372 (2003)).

In one embodiment, a therapeutic agent for use in combination with an anti-TF antibody for treating the disorders as described above may be a tumor suppressor gene-containing nucleic acid or vector such as a replication-deficient adenovirus encoding human recombinant wild-type p53/SCH58500, etc.; antisense nucleic acids targeted to oncogenes, mutated, or deregulated genes; or siRNA targeted to mutated or deregulated genes. Examples of tumor suppressor targets include, for example, BRCA1, RB1, BRCA2, DPC4 (Smad4), MSH2, MLH1, and DCC.

In one embodiment, a therapeutic agent for use in combination with an anti-TF antibody for treating the disorders as described above may be an anti-cancer nucleic acid, such as genasense (augmerosen/G3139), LY900003 (ISIS 3521), ISIS 2503, OGX-011 (ISIS 112989), LE-AON/LEraf-AON (liposome encapsulated c-raf antisense oligonucleotide/ISIS-5132), MG98, and other antisense nucleic acids that target PKCα, clusterin, IGFBPs, protein kinase A, cyclin D1, or Bcl-2h.

In one embodiment, a therapeutic agent for use in combination with an anti-TF antibody for treating the disorders as described above may be an anti-cancer inhibitory RNA molecule (see for instance Lin et al., Curr Cancer Drug Targets. 1(3), 241-7 (2001), Erratum in: Curr Cancer Drug Targets. 3(3), 237 (2003), Lima et al., Cancer Gene Ther. 11(5), 309-16 (2004), Grzmil et al., Int J Oncol. 4(1), 97-105 (2004), Collis et al., Int J Radiat Oncol Biol Phys. 57(2 Suppl), S144

(2003), Yang et al., Oncogene. 22(36), 5694-701 (2003) and Zhang et al., Biochem Biophys Res Commun. 303(4), 1169-78 (2003)).

Compositions and combination administration methods of the present invention also include the administration of nucleic acid vaccines, such as naked DNA vaccines encoding such cancer antigens/tumor-associated antigens (see for instance U.S. Pat. No. 5,589,466, U.S. Pat. No. 5,593,972, U.S. Pat. No. 5,703,057, U.S. Pat. No. 5,879,687, U.S. Pat. No. 6,235,523, and U.S. Pat. No. 6,387,888). In one embodiment, the combination administration method and/or combination composition comprises an autologous vaccine composition. In one embodiment, the combination composition and/or combination administration method comprises a whole cell vaccine or cytokine-expressing cell (for instance a recombinant IL-2 expressing fibroblast, recombinant cytokine-expressing dendritic cell, and the like) (see for instance Kowalczyk et al., Acta Biochim Pol. 50(3), 613-24 (2003), Reilly et al., Methods Mol Med. 69, 233-57 (2002) and Tirapu et al., Curr Gene Ther. 2(1), 79-89 (2002). Another example of such an autologous cell approach that may be useful in combination methods of the present invention is the MyVax® Personalized Immunotherapy method (previously referred to as GTOP-99) (Genitope Corporation—Redwood City, Calif., USA).

In one embodiment, the present invention provides combination compositions and combination administration methods wherein an anti-TF antibody is combined or co-administered with a virus, viral proteins, and the like. Replication-deficient viruses, that generally are capable of one or only a few rounds of replication in vivo, and that are targeted to tumor cells, may for instance be useful components of such compositions and methods. Such viral agents may comprise or be associated with nucleic acids encoding immunostimulants, such as GM-CSF and/or IL-2. Both naturally oncolytic and such recombinant oncolytic viruses (for instance HSV-1 viruses, reoviruses, replication-deficient and replication-sensitive adenovirus, etc.) may be useful components of such methods and compositions. Accordingly, in one embodiment, the present invention provides combination compositions and combination administration methods wherein an anti-TF antibody is combined or co-administered with an oncolytic virus. Examples of such viruses include oncolytic adenoviruses and herpes viruses, which may or may not be modified viruses (see for instance Shah et al., J Neurooncol. 65(3), 203-26 (2003), Stiles et al., Surgery. 134(2), 357-64 (2003), Sunarmura et al., Pancreas. 28(3), 326-9 (2004), Teshigahara et al., J Surg Oncol. 85(1), 42-7 (2004), Varghese et al., Cancer Gene Ther. 9(12), 967-78 (2002), Wildner et al., Cancer Res. 59(2), 410-3 (1999), Yamanaka, Int J Oncol. 24(4), 919-23 (2004) and Zwiebel et al., Semin Oncol. 28(4), 336-43 (2001).

Combination compositions and combination administration methods of the present invention may also involve "whole cell and "adoptive" immunotherapy methods. For instance, such methods may comprise infusion or re-infusion of immune system cells (for instance tumor-infiltrating lymphocytes (TILs), such as $CD4^+$ and/or $CD8^+$ T cells (for instance T cells expanded with tumor-specific antigens and/or genetic enhancements), antibody-expressing B cells or other antibody producing/presenting cells, dendritic cells (e.g., anti-cytokine expressing recombinant dendritic cells, dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions.

In one embodiment, an anti-TF antibody may be delivered to a patient in combination with the application of an internal vaccination method. Internal vaccination refers to induced tumor or cancer cell death, such as drug-induced or radiation-induced cell death of tumor cells, in a patient, that typically leads to elicitation of an immune response directed towards (i) the tumor cells as a whole or (ii) parts of the tumor cells including (a) secreted proteins, glycoproteins or other products, (b) membrane-associated proteins or glycoproteins or other components associated with or inserted in membranes, and/or (c) intracellular proteins or other intracellular components. An internal vaccination-induced immune response may be humoral (i.e. antibody—complement-mediated) or cell-mediated (e.g., the development and/or increase of endogenous cytotoxic T lymphocytes that recognize the internally killed tumor cells or parts thereof). In addition to radiotherapy, non-limiting examples of drugs and agents that may be used to induce said tumor cell-death and internal vaccination are conventional chemotherapeutic agents, cell-cycle inhibitors, anti-angiogenesis drugs, monoclonal antibodies, apoptosis-inducing agents, and signal transduction inhibitors.

Examples of other anti-cancer agents, which may be relevant as therapeutic agents for use in combination with an anti-TF antibody for treating the disorders as described above are differentiation inducing agents, retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRa, PDGFRbeta, Flk2, Flt4, FGFR1, FGFR2, FGFR3, FGFR4, TRKA, TRKC, c-met, Ron, Sea, Tie, Tie2, Eph, Ret, Ros, Alk, LTK, PTK7 and similar agents.

Examples of other anti-cancer agents, which may be relevant as therapeutic agents for use in combination with an anti-TF antibody for treating the disorders as described above are cathepsin B, modulators of cathepsin D dehydrogenase activity, glutathione-S-transferase (such as glutacylcysteine synthetase and lactate dehydrogenase), and similar agents.

Examples of other anti-cancer agents, which may be relevant as therapeutic agents for use in combination with an anti-TF antibody for treating the disorders as described above are estramustine and epirubicin.

Examples of other anti-cancer agents, which may be relevant as therapeutic agents for use in combination with an anti-TF antibody for treating the disorders as described above are a HSP90 inhibitor like 17-allyl amino geld-anamycin, antibodies directed against a tumor antigen such as PSA, CA125, KSA, etc., integrins like integrin β1, inhibitors of VCAM and similar agents.

Examples of other anti-cancer agents, which may be relevant as therapeutic agents for use in combination with an anti-TF antibody for treating the disorders as described above are calcineurin-inhibitors (such as valspodar, PSC 833 and other MDR-1 or p-glycoprotein inhibitors), TOR-inhibitors (such as sirolimus, everolimus and rapamcyin). and inhibitors of "lymphocyte homing" mechanisms (such as FTY720), and agents with effects on cell signaling such as adhesion molecule inhibitors (for instance anti-LFA, etc.).

In one embodiment, the anti-TF antibody of the invention is for use in combination with one or more other therapeutic antibodies, such as bevacizumab (Avastin®), zalutumumab, cetuximab (Erbitux®), panitumumab (Vectibix™), ofatumumab, zanolimumab, daratumumab, ranibizumab (Lucentis®), Zenapax, Simulect, Remicade, Humira, Tysabri, Xolair, raptiva, nimotuzumab, rituximab and/or trastuzumab (Herceptin®). Other therapeutic antibodies which may be used in combination with the antibody of the present invention are those disclosed in WO98/40408 (antibodies that can bind native human TF), WO04/094475 (antibodies capable of binding to human tissue factor, which do not inhibit factor mediated blood coagulation compared to a normal plasma control), WO03/093422 (antibodies that bind with greater affinity to the TF:VIIa complex than to TF alone), or WO03/037361 (TF agonist or antagonist for treatment related to apoptosis).

In another embodiment, two or more different antibodies of the invention as described herein are used in combination for the treatment of disease. Particularly interesting combinations include two or more non-competing antibodies. Thus, in one embodiment, a patient is treated with a combination of an antibody of cross-block Group I defined herein with an antibody of Group II or III, as defined herein. In another embodiment, a patient is treated with a combination of an antibody of Group II as defined herein below, with an antibody of Group III. Such combination therapy may lead to binding of an increased number of antibody molecules per cell, which may give increase efficacy, e.g. via activation of complement-mediated lysis.

In one embodiment, an anti-TF antibody may be administered in connection with the delivery of one or more agents that promote access of the anti-TF antibody or combination composition to the interior of a tumor. Such methods may for example be performed in association with the delivery of a relaxin, which is capable of relaxing a tumor (see for instance U.S. Pat. No. 6,719,977). In one embodiment, an anti-TF antibody of the present invention may be bonded to a cell penetrating peptide (CPP). Cell penetrating peptides and related peptides (such as engineered cell penetrating antibodies) are described in for instance Zhao et al., J Immunol Methods. 254(1-2), 137-45 (2001), Hong et al., Cancer Res. 60(23), 6551-6 (2000). Lindgren et al., Biochem J. 377(Pt 1), 69-76 (2004), Buerger et al., J Cancer Res Clin Oncol. 129 (12), 669-75 (2003), Pooga et al., FASEB J. 12(1), 67-77 (1998) and Tseng et al., Mol Pharmacol. 62(4), 864-72 (2002).

In one embodiment, the present invention provides a method for treating a disorder involving cells expressing TF in a subject, which method comprises administration of a therapeutically effective amount of an anti-TF antibody and at least one anti-inflammatory agent to a subject in need thereof.

In one embodiment such an anti-inflammatory agent may be selected from aspirin and other salicylates, Cox-2 inhibitors (such as rofecoxib and celecoxib), NSAIDs (such as ibuprofen, fenoprofen, naproxen, sulindac, diclofenac, piroxicam, ketoprofen, diflunisal, nabumetone, etodolac, oxaprozin, and indomethacin), anti-IL6R antibodies, anti-IL8 antibodies (e.g. antibodies described in WO2004058797, e.g. 10F8), anti-IL15 antibodies (e.g. antibodies described in WO03017935 and WO2004076620), anti-IL15R antibodies, anti-CD4 antibodies (e.g. zanolimumab), anti-CD11a antibodies (e.g., efalizumab), anti-alpha-4/beta-1 integrin (VLA4) antibodies (e.g. natalizumab), CTLA4-Ig for the treatment of inflammatory diseases, prednisolone, prednisone, disease modifying antirheumatic drugs (DMARDs) such as methotrexate, hydroxychloroquine, sulfasalazine, pyrimidine synthesis inhibitors (such as leflunomide), IL-1 receptor blocking agents (such as anakinra), TNF-α blocking agents (such as etanercept, infliximab, and adalimumab) and similar agents.

In one embodiment, such an immunosuppressive and/or immunomodulatory agent may be selected from cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, thymopentin, thymosin-α and similar agents.

In one embodiment, such an immunosuppressive and/or immunomodulatory agent may be selected from immunosuppressive antibodies, such as antibodies binding to p75 of the IL-2 receptor, antibodies against CD25 (e.g. those described in WO2004045512, such as AB1, AB7, AB11, and AB12), or antibodies binding to for instance MHC, CD2, CD3, CD4, CD7, CD28, B7, CD40, CD45, IFNγ, TNF-α, IL-4, IL-5, IL-6R, IL-7, IL-8, IL-10, CD11a, or CD58, or antibodies binding to their ligands.

In one embodiment, such an immunosuppressive and/or immunomodulatory agent may be selected from soluble IL-15R, IL-10, B7 molecules (B7-1, B7-2, variants thereof, and fragments thereof), ICOS, and OX40, an inhibitor of a negative T cell regulator (such as an antibody against CTLA4) and similar agents.

In one embodiment, the present invention provides a method for treating a disorder involving cells expressing TF in a subject, which method comprises administration of a therapeutically effective amount of an anti-TF antibody and an anti-C3b(i) antibody to a subject in need thereof.

In one embodiment, a therapeutic agent for use in combination with anti-TF antibodies for treating the disorders as described above may be selected from histone deacetylase inhibitors (for instance phenylbutyrate) and/or DNA repair agents (for instance DNA repair enzymes and related compositions such as dimericine).

Methods of the present invention for treating a disorder as described above comprising administration of a therapeutically effective amount of an anti-TF antibody may also comprise anti-cancer directed photodynamic therapy (for instance anti-cancer laser therapy—which optionally may be practiced with the use of photosensitizing agent, see, for instance Zhang et al., J Control Release. 93(2), 141-50 (2003)), anti-cancer sound-wave and shock-wave therapies (see for instance Kambe et al., Hum Cell. 10(1), 87-94 (1997)), and/or anti-cancer nutraceutical therapy (see for instance Roudebush et al., Vet Clin North Am Small Anim Pract. 34(1), 249-69, viii (2004) and Rafi, Nutrition. 20(1), 78-82 (2004). Likewise, an anti-TF antibody may be used for the preparation of a pharmaceutical composition for treating a disorder as described above to be administered with anti-cancer directed photodynamic therapy (for instance anti-cancer laser therapy—which optionally may be practiced with the use of photosensitizing agent, anti-cancer sound-wave and shockwave therapies, and/or anti-cancer nutraceutical therapy.

In one embodiment, the present invention provides a method for treating a disorder involving cells expressing TF in a subject, which method comprises administration of a therapeutically effective amount of an anti-TF antibody, such as an anti-TF antibody of the present invention, and radiotherapy to a subject in need thereof.

In one embodiment, the present invention provides a method for treating or preventing cancer, which method comprises administration of a therapeutically effective amount of an anti-TF antibody, such as an anti-TF antibody of the present invention, and radiotherapy to a subject in need thereof.

In one embodiment, the present invention provides the use of an anti-TF antibody, such as an anti-TF antibody of the present invention, for the preparation of a pharmaceutical composition for treating cancer to be administered in combination with radiotherapy.

Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In a further embodiment, the present invention provides a method for treating or preventing cancer, which method comprises administration to a subject in need thereof of a therapeutically effective amount of an anti-TF antibody, such as an anti-TF antibody of the present invention, in combination with surgery.

As described above, a pharmaceutical composition of the present invention may be administered in combination therapy, i.e., combined with one or more agents relevant for the disease or condition to be treated either as separate pharmaceutical compositions or with a compound of the present invention coformulated with one or more additional therapeutic agents as described above. Such combination therapies may require lower dosages of the compound of the present invention and/or the co-administered agents, thus avoiding possible toxicities or complications associated with the various monotherapies.

In addition to the above, other interesting combination therapies include the following:

For the treatment of pancreatic cancer an anti-TF antibody in combination with an antimetabolite, such as 5-fluorouracil and/or gemcitabine, possibly in combination with one or more compounds selected from: 90Y-hPAM4, ARC-100, ARQ-197, AZD-6244, bardoxolone methyl, cixutumumab, (IMC-A12), folitixorin calcium, GVAX, ipilimumab, KRX-0601, merbarone, MGCD-0103, MORAb-009, PX-12, Rh-Apo2L, TLN-4601, trabedersen, volociximab (M200), WX-671, pemetrexed, rubitecan, ixabepilone, OCX-0191Vion, 216586-46-8, lapatinib, matuzumab, imatinib, sorafinib, trastuzumab, exabepilone, erlotinib, avastin and cetuximab For the treatment of colorectal cancer an anti-TF antibody in combination with one or more compounds selected from: gemcitabine, bevacizumab, FOLFOX, FOLFIRI, XELOX, IFL, oxaliplatin, irinotecan, 5-FU/LV, Capecitabine, UFT, EGFR targeting agents, such as cetuximab. panitumumab, zalutumumab, nimotuzumab; VEGF inhibitors, or tyrosine kinase inhibitors such as sunitinib.

For the treatment of breast cancer an anti-TF antibody in combination with one or more compounds selected from: antimetabolites, anthracyclines, taxanes, alkylating agents, epothilones anti-hormonal (femar, tamoxifen etc), inhibitors of ErbB2 (Her2/neu) (such as herceptin and similar agents), CAF/FAC (cyclofosfamide, doxorubicine, 5FU) AC (cyclo, doxo), CMF (cyclo, methotrexate, 5FU), Docetaxel+capecitabine, GT (paclitaxel, gemcitabine) FEC (cyclo, epi, 5FU) in combination with herceptine: Paclitaxel+/−carboplatin, Vinorelbine, Docetaxel, CT in combination with lapatinib; Capecitabine For the treatment of bladder an anti-TF antibody in combination with one or more compounds selected from: antimetabolites (gemcitabine, alimta, methotrexate), platinum analogues (cisplatin, carboplatin), EGFr inhibitors (such as cetuximab or zalutumumab), VEGF inhibitors (such as Avastin) doxorubicin, tyrosine kinase inhibitors such as gefitinib, trastuzumab, anti-mitotic agent, such as taxanes, for instance paclitaxel, and vinca alkaloids, for instance vinblastine.

For the treatment of prostate cancer an anti-TF antibody in combination with one or more compounds selected from: hormonal/antihormonal therapies; such as antiandrogens, Luteinizing hormone releasing hormone (LHRH) agonists, and chemotherapeutics such as taxanes, mitoxantrone, estramustine, 5FU, vinblastine, ixabepilone, For the treatment of ovarian cancer an anti-TF antibody in combination with one or more compounds selected from: an anti-mitotic agent, such as taxanes, and vinca alkaloids, caelyx, topotecan.

Diagnostic Uses

The anti-TF antibodies of the invention may also be used for diagnostic purposes. Thus, in a further aspect, the invention relates to a diagnostic composition comprising an anti-TF antibody as defined herein.

In one embodiment, the anti-TF antibodies of the present invention may be used in vivo or in vitro for diagnosing diseases wherein activated cells expressing TF play an active role in the pathogenesis, by detecting levels of TF, or levels of cells which contain TF on their membrane surface. This may be achieved, for example, by contacting a sample to be tested, optionally along with a control sample, with the anti-TF antibody under conditions that allow for formation of a complex between the antibody and TF. Complex formation is then detected (e.g., using an ELISA). When using a control sample along with the test sample, complex is detected in both samples and any statistically significant difference in the formation of complexes between the samples is indicative of the presence of TF in the test sample.

Thus, in a further aspect, the invention relates to a method for detecting the presence of TF antigen, or a cell expressing TF, in a sample comprising:
  contacting the sample with an anti-TF antibody of the invention or a bispecific molecule of the invention, under conditions that allow for formation of a complex between the antibody and TF; and
  analyzing whether a complex has been formed.

In one embodiment, the method is performed in vitro.

More specifically, the present invention provides methods for the identification of, and diagnosis of invasive cells and tissues, and other cells targeted by anti-TF antibodies of the present invention, and for the monitoring of the progress of therapeutic treatments, status after treatment, risk of developing cancer, cancer progression, and the like.

In one example of such a diagnostic assay, the present invention provides a method of diagnosing the level of invasive cells in a tissue comprising forming an immunocomplex between an anti-TF antibody and potential TF-containing tissues, and detecting formation of the immunocomplex, wherein the formation of the immunocomplex correlates with the presence of invasive cells in the tissue. The contacting may be performed in vivo, using labeled isolated antibodies and standard imaging techniques, or may be performed in vitro on tissue samples.

Anti-TF antibodies may be used to detect TF-containing peptides and peptide fragments in any suitable biological sample by any suitable technique. Examples of conventional immunoassays provided by the present invention include, without limitation, an ELISA, an RIA, FACS assays, plasmon resonance assays, chromatographic assays, tissue immunohistochemistry, Western blot, and/or immunoprecipitation using an anti-TF antibody. Anti-TF antibodies of the present invention may be used to detect TF and TF-fragments from humans. Suitable labels for the anti-TF antibody and/or secondary antibodies used in such techniques include, without limitation, various enzymes, prosthetic groups, fluorescent materials, luminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S, and $^{3}$H.

Anti-TF antibodies may also be assayed in a biological sample by a competition immunoassay utilizing TF peptide standards labeled with a detectable substance and an unlabeled anti-TF antibody. In such an assay, the biological sample, the labeled TF peptide standard(s) and the anti-TF antibodies are combined and the amount of labeled TF standard bound to the unlabeled anti-TF antibody is determined. The amount of TF peptide in the biological sample is inversely proportional to the amount of labeled TF standard bound to the anti-TF antibody.

The anti-TF antibodies are particularly useful in the in vivo imaging of tumors. In vivo imaging of tumors associated with TF may be performed by any suitable technique. For example, $^{99}$Tc-labeling or labeling with another gamma-ray emitting isotope may be used to label anti-TF antibodies in tumors or secondary labeled (e.g., FITC labeled) anti-TF antibody:TF complexes from tumors and imaged with a gamma scintillation camera (e.g., an Elscint Apex 409ECT device), typically using low-energy, high resolution collimator or a low-energy all-purpose collimator. Stained tissues may then be assessed for radioactivity counting as an indicator of the amount of TF-associated peptides in the tumor. The images obtained by the use of such techniques may be used to assess biodistribution of TF in a patient, mammal, or tissue, for example in the context of using TF or TF-fragments as a biomarker for the presence of invasive cancer cells. Variations on this technique may include the use of magnetic resonance imaging (MRI) to improve imaging over gamma camera techniques. Similar immunoscintigraphy methods and principles are described in, e.g., Srivastava (ed.), Radiolabeled Monoclonal Antibodies For Imaging And Therapy (Plenum Press 1988), Chase, "Medical Applications of Radioisotopes," in Remington's Pharmaceutical Sciences, 18th Edition, Gennaro et al., (eds.), pp. 624-652 (Mack Publishing Co., 1990), and Brown, "Clinical Use of Monoclonal Antibodies," in Biotechnology And Pharmacy 227-49, Pezzuto et al., (eds.) (Chapman & Hall 1993). Such images may also be used for targeted delivery of other anti-cancer agents, examples of which are described herein (e.g., apoptotic agents, toxins, or CHOP chemotherapy compositions). Moreover, such images may also or alternatively serve as the basis for surgical techniques to remove tumors. Furthermore, such in vivo imaging techniques may allow for the identification and localization of a tumor in a situation where a patient is identified as having a tumor (due to the presence of other biomarkers, metastases, etc.), but the tumor cannot be identified by traditional analytical techniques. All of these methods are features of the present invention.

The in vivo imaging and other diagnostic methods provided by the present invention are particularly useful in the detection of micrometastases in a human patient (e.g., a patient not previously diagnosed with cancer or a patient in a period of recovery/remission from a cancer). Carcinoma cancer cells, which may make up to 90% of all cancer cells, for example, have been demonstrated to stain very well with anti-TF antibody conjugate compositions. Detection with monoclonal anti-TF antibodies described herein may be indicative of the presence of carcinomas that are aggressive/invasive and also or alternatively provide an indication of the feasibility of using related monoclonal anti-TF antibody against such micrometastases.

In one embodiment, the present invention provides an in vivo imaging method wherein an anti-TF antibody of the present invention is conjugated to a detection-promoting radio-opaque agent, the conjugated antibody is administered to a host, such as by injection into the bloodstream, and the presence and location of the labeled antibody in the host is assayed. Through this technique and any other diagnostic method provided herein, the present invention provides a method for screening for the presence of disease-related cells in a human patient or a biological sample taken from a human patient.

For diagnostic imaging, radioisotopes may be bound to a anti-TF antibody either directly, or indirectly by using an intermediary functional group. Useful intermediary functional groups include chelators, such as ethylenediaminetetraacetic acid and diethylenetriaminepentaacetic acid (see for instance U.S. Pat. No. 5,057,313).

In addition to radioisotopes and radio-opaque agents, diagnostic methods may be performed using anti-TF antibodies that are conjugated to dyes (such as with the biotin-streptavidin complex), contrast agents, fluorescent compounds or molecules and enhancing agents (e.g. paramagnetic ions) for magnetic resonance imaging (MRI) (see, e.g., U.S. Pat. No. 6,331,175, which describes MRI techniques and the preparation of antibodies conjugated to a MRI enhancing agent). Such diagnostic/detection agents may be selected from agents for use in magnetic resonance imaging, and fluorescent compounds. In order to load an anti-TF antibody with radioactive metals or paramagnetic ions, it may be necessary to react it with a reagent having a long tail to which are attached a multiplicity of chelating groups for binding the ions. Such a tail may be a polymer such as a polylysine, polysaccharide, or other derivatized or derivatizable chain having pendant groups to which may be bound chelating groups such as, e.g., porphyrins, polyamines, crown ethers, bisthiosemicarbazones, polyoximes, and like groups known to be useful for this purpose. Chelates may be coupled to anti-TF antibodies using standard chemistries.

Thus, the present invention provides diagnostic anti-TF antibody conjugates, wherein the anti-TF antibody is conjugated to a contrast agent (such as for magnetic resonance imaging, computed tomography, or ultrasound contrast-enhancing agent) or a radionuclide that may be, for example, a gamma-, beta-, alpha-, Auger electron-, or positron-emitting isotope.

In a further aspect, the invention relates to a kit for detecting the presence of TF antigen, or a cell expressing TF, in a sample comprising
  an anti-TF antibody of the invention or a bispecific molecule of the invention; and
  instructions for use of the kit.

In one embodiment, the present invention provides a kit for diagnosis of cancer comprising a container comprising an anti-TF antibody, and one or more reagents for detecting binding of the anti-TF antibody to a TF peptide. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. In one embodiment, the present invention provides a diagnostic kit comprising one or more anti-TF antibodies, of the present invention in labeled or unlabeled form in suitable container(s), reagents for the incubations for an indirect assay, and substrates or derivatizing agents for detection in such an assay, depending on the nature of the label. Control reagent(s) and instructions for use also may be included.

Diagnostic kits may also be supplied for use with an anti-TF antibody, such as a conjugated/labeled anti-TF antibody, for the detection of a cellular activity or for detecting the presence of TF peptides in a tissue sample or host. In such diagnostic kits, as well as in kits for therapeutic uses described elsewhere herein, an anti-TF antibody typically may be provided in a lyophilized form in a container, either alone or in conjunction with additional antibodies specific for a target cell or peptide. Typically, a pharmaceutical acceptable carrier (e.g., an inert diluent) and/or components thereof, such as a Tris, phosphate, or carbonate buffer, stabilizers, preservatives, biocides, biocides, inert proteins, e.g., serum albumin, or the like, also are included (typically in a separate container for mixing) and additional reagents (also typically in separate container(s)). In certain kits, a secondary antibody capable of binding to the anti-TF antibody, which typically is present in a separate container, is also included. The second antibody is typically conjugated to a label and formulated in manner similar to the anti-TF antibody the present invention. Using the methods described above and elsewhere herein anti-TF antibodies may be used to define subsets of cancer/tumor cells and characterize such cells and related tissues/growths.

In situ detection may be accomplished by removing a histological specimen from a patient, and providing the combination of labeled anti-TF antibodies, of the present invention to such a specimen. The anti-TF antibody of the present invention may be provided by applying or by overlaying the labeled anti-TF antibody of the present invention to a biological sample. Through the use of such a procedure, it is possible to determine not only the presence of TF or TF-fragments but also the distribution of such peptides in the examined tissue (e.g., in the context of assessing the spread of cancer cells). Using the present invention, those of ordinary skill will readily perceive that any of a wide variety of histological methods (such as staining procedures) may be modified in order to achieve such in situ detection.

In a further aspect, the invention relates to an anti-idiotypic antibody which binds to an anti-TF antibody of the invention as described herein.

An anti-idiotypic (Id) antibody is an antibody which recognizes unique determinants generally associated with the antigen-binding site of an antibody. An Id antibody may be prepared by immunizing an animal of the same species and genetic type as the source of an anti-TF mAb with the mAb to which an anti-Id is being prepared. The immunized animal typically can recognize and respond to the idiotypic determinants of the immunizing antibody by producing an antibody to these idiotypic determinants (the anti-Id antibody). Such antibodies are described in for instance U.S. Pat. No. 4,699,880. Such antibodies are further features of the present invention.

An anti-Id antibody may also be used as an "immunogen" to induce an immune response in yet another animal, producing a so-called anti-anti-Id antibody. An anti-anti-Id may be epitopically identical to the original mAb, which induced the anti-Id. Thus, by using antibodies to the idiotypic determinants of a mAb, it is possible to identify other clones expressing antibodies of identical specificity. Anti-Id antibodies may be varied (thereby producing anti-Id antibody variants) and/or derivatized by any suitable technique, such as those described elsewhere herein with respect to anti-TF antibodies of the present invention. For example, anti-Id mAbs may be coupled to a carrier such as keyhole limpet hemocyanin (KLH) and used to immunize BALB/c mice. Sera from these mice typically will contain anti-anti-Id antibodies that have the binding properties similar if not identical to an original/parent TF antibody.

The present invention is further illustrated by the following examples which should not be construed as further limiting.

EXAMPLES

Example 1

Expression Constructs for Tissue Factor (TF)

Fully codon-optimized constructs for expression of TF or its extracellular domains in HEK, NS0 or CHO cells, were generated. The proteins encoded by these constructs are identical to Genbank accession NP_001984 for TF. The constructs contained suitable restriction sites for cloning and an optimal Kozak sequence (Kozak, 1987). The constructs were cloned in the mammalian expression vector pEE13.4 (Lonza Biologics) (Bebbington, Renner et al. 1992), obtaining pEE13.4TF. PCR was used to amplify the part, encoding the extracellular domain (ECD) (amino acid 1-251) of TF, from the synthetic construct, adding a C-terminal His tag containing 6 His residues (TFECDHis). The construct was cloned in pEE13.4 and fully sequenced to confirm the correctness of the construct.

Example 2

Transient Expression in HEK-293F Cells

Freestyle™ 293-F (a HEK-293 subclone adapted to suspension growth and chemically defined Freestyle medium, (HEK-293F)) cells were obtained from Invitrogen and transfected with the appropriate plasmid DNA, using 293fectin (Invitrogen) according to the manufacturer's instructions. In the case of antibody expression, the appropriate heavy chain and light chain vectors, as described in Example 10, were co-expressed.

Example 3

Semi-Stable Expression in NS0 Cells pEE13.4TF was stably transfected in NS0 cells and stable clones were selected on growth in the absence of glutamine and in the presence of 7.5 μM of methylsulphoximine (MSX). A pool of clones was grown in suspension culture while maintaining selection pressure. Pools were tested for TF expression by FACS analysis and secured for further use.

Example 4

Stable Expression in CHO Cells pEE13.4TF was stably transfected in CHO-K1SV (Lonza Biologics) cells and stable clones were selected on growth in the absence of glutamine and in the presence of 50 µM MSX. Single clones were picked and expanded and tested for TF expression by FACS analysis as described below. High expressing clones were chosen and secured for further use.

Example 5

Purification of His-Tagged TF

TFECDhis was expressed I HEK-293F cells. The his-tag in TFECDHis enables purification with immobilized metal affinity chromatography. In this process, a chelator fixed onto the chromatographic resin is charged with $Co^{2+}$ cations. TFECDHis-containing supernatant is incubated with the resin in batch mode (i.e. solution). The His-tagged protein binds strongly to the resin beads, while other proteins present in the culture supernatant do not bind strongly. After incubation the beads are retrieved from the supernatant and packed into a column. The column is washed in order to remove weakly bound proteins. The strongly bound TFECDHis proteins are then eluted with a buffer containing imidazole, which competes with the binding of His to $Co^{2+}$. The eluent is removed from the protein by buffer exchange on a desalting column.

Example 6

Immunization Procedure of Transgenic Mice

HuMab mice were immunized every fortnight alternating with $5 \times 10^6$ semi-stable transfected NS0-TF cells, or with 20 µg of TFECDHis protein. Eight immunizations were performed in total, four intraperitoneal (IP) and four subcutaneous (SC) immunizations at the tail base. The first immunization with cells was done in complete Freunds' adjuvant (CFA; Difco Laboratories, Detroit, Mich., USA). For all other immunizations, cells were injected IP in PBS and TFECDHis was injected SC using incomplete Freunds' adjuvant (IFA; Difco Laboratories, Detroit, Mich., USA). When serum titers were found to be sufficient (dilution of serum of 1/50 or lower found positive in antigen specific screening assay as described in Example 7 on at least 2 sequential, biweekly screening events), mice were additionally boosted twice intravenously (IV) with 10 µg TFECDHis protein in 100 µl PBS, 4 and 3 days before fusion. The first immunization with cells was done in CFA, for all other (7) immunizations cells were injected IP in PBS. When serum titers were found to be sufficient, mice were additionally boosted twice IV with $1 \times 10^6$ transiently semi-stable transfected NS0-TF cells in 100 µl PBS, 4 and 3 days before fusion.

When serum titers were found to be sufficient (defined as above), mice were additionally boosted twice intravenously (IV) with 10 µg TFECDHis protein in 100 µl PBS, 4 and 3 days before fusion.

Example 7

Homogeneous Antigen Specific Screening Assay

The presence of anti-TF antibodies in sera of immunized mice or HuMab (human monoclonal antibody) hybridoma or transfectoma culture supernatant was determined by homogeneous antigen specific screening assays (four quadrant) using Fluorometric Micro volume Assay Technology (FMAT; Applied Biosystems®, Foster City, Calif., USA).

For this, a combination of 3 cell based assays and one bead based assay was used. In the cell based assays, binding to TH1015-TF (HEK-293F cells transiently expressing TF; produced as described above) and A431 (which express TF at the cell surface) as well as HEK293 wild type cells (do not express TF, negative control) was determined. In the bead based assay, binding to biotinylated TF coupled on a streptavidin bead (SB1015-TF) was determined.

Samples were added to the cells/beads to allow binding to TF. Subsequently, binding of HuMab was detected using a fluorescent conjugate (Goat anti-Human IgG-Cy5; Jackson ImmunoResearch). Mouse anti-human TF antibody (ERL; coupled to Alexa-647 at Genmab) was used as positive control, HuMAb-mouse pooled serum and mouse-chrompure-Alexa647 antibody were used as negative controls. The samples were scanned using an Applied Biosystems® 8200 Cellular Detection System (8200 CDS) and 'counts×fluorescence' was used as read-out.

Example 8

HuMab Hybridoma Generation

HuMab mice with sufficient antigen-specific titer development (defined as above) were euthanized and the spleen and lymph nodes flanking the abdominal aorta and vena cava were collected. Fusion of splenocytes and lymph node cells to a mouse myeloma cell line was done by electrofusion using a CEEF 50 Electrofusion System (Cyto Pulse Sciences, Glen Burnie, Md., USA), essentially according to the manufacturer's instructions. Selection and culturing of the resulting HuMab hybridomas was done based upon standard protocols (e.g. as described in Coligan J. E., Bierer, B. E., Margulies, D. H., Shevach, E. M. and Strober, W., eds. Current Protocols in Immunology, John Wiley & Sons, Inc., 2006).

Example 9

Mass Spectrometry of Purified Antibodies

Small aliquots of 0.8 ml antibody containing supernatant from 6-well or Hyperflask stage were purified using PhyTip columns containing Protein G resin (PhyNexus Inc., San Jose, USA) on a Sciclone ALH 3000 workstation (Caliper Lifesciences, Hopkinton, USA). The PhyTtip columns were used according to manufacturers instructions, but buffers were replaced by: Binding Buffer PBS (B. Braun, Medical B.V., Oss, Netherlands) and Elution Buffer 0.1M Glycine-HCl pH 2.7 (Fluka Riedel-de Haën, Buchs, Germany). After purification, samples were neutralized with 2M Tris-HCl pH 9.0 (Sigma-Aldrich, Zwijndrecht, Netherlands). Alternatively, in some cases larger volumes of culture supernatant were purified using Protein A affinity column chromatography.

After purification, the samples were placed in a 384-well plate (Waters, 100 ul square well plate, part#186002631). Samples were deglycosylated overnight at 37° C. with N-glycosidase F (Roche cat no 11365177001. DTT (15 mg/ml) was added (1 μl/well) and incubated for 1 h at 37° C. Samples (5 or 6 ul) were desalted on an Acquity HPLC™ (Waters, Milford, USA) with a BEH300 C18, 1.7 μm, 2.1×50 mm column at 60° C. MQ water and LC-MS grade acetonitrile (Biosolve, cat no 01204101, Valkenswaard, The Netherlands) with both 0.1% formic acid (Fluka, cat no 56302, Buchs, Germany), were used as Eluens A and B, respectively. Time-of-flight electrospray ionization mass spectra were recorded on-line on a micrOTOF™ mass spectrometer (Bruker, Bremen, Germany) operating in the positive ion mode. Prior to analysis, a 900-3000 m/z scale was calibrated with ES tuning mix (Agilent Technologies, Santa Clara, USA). Mass spectra were deconvoluted with DataAnalysis™ software v. 3.4 (Bruker) using the Maximal Entropy algorithm searching for molecular weights between 5 and 80 kDa.

After deconvolution the resulting heavy and light chain masses for all samples were compared in order to find duplicate antibodies. In the comparison of the heavy chains the possible presence of C-terminal lysine variants was taken into account. This resulted in a list of unique antibodies, where unique is defined as a unique combination of heavy and light chains. In case duplicate antibodies were found, the results from other tests were used to decide which was the best material to continue experiments with.

MS analysis of the molecular weights of heavy and light chains of 118 TF specific hybridomas yielded 70 unique antibodies (unique heavy chain/light chain combination). These were characterized in a number of functional assays, identifying 14 lead candidates, TF specific antibodies.

Example 10

Sequence Analysis of the Anti-TF HuMab Variable Domains and Cloning in Expression Vectors Total RNA of the anti-TF HuMabs was prepared from 5×10⁶ hybridoma cells and 5'-RACE-Complementary DNA (cDNA) was prepared from 100 ng total RNA, using the SMART™ RACE cDNA Amplification kit (Clontech), according to the manufacturer's instructions. VH (variable region of heavy chain) and VL (variable region of light chain) coding regions were amplified by PCR and cloned into the pCR™-Blunt II-TOPO® vector (Invitrogen) using the Zero Blunt®-Topo® PCR cloning kit (Invitrogen). For each HuMab, 16 VL clones and 8 VH clones were sequenced. The sequences are given in the Sequence Listing and FIG. 1 herein.

Table 1A and Table 1B (below) give an overview of the antibody sequences information and most homologous germline sequences.

TABLE 1B

Light chain homologies

| Ab | V-GENE and allele | V-REGION identity % (nt) | J-GENE and allele | CDR-IMGT lengths |
|---|---|---|---|---|
| 003 | IGKV1-13*02 | 99.28% (277/279 nt) | IGKJ4*01 | [6.3.9] |
| 011 | IGKV1D-16*01 | 98.57% (275/279 nt) | IGKJ2*01 | [6.3.9] |
| 013 | IGKV1D-16*01 | 98.57% (275/279 nt) | IGKJ5*01 | [6.3.9] |
| 092 | IGKV1D-16*01 | 99.28% (277/279 nt) | IGKJ2*01 | [6.3.10] |
| 098 | IGKV1D-16*01 | 100.00% (279/279 nt) | IGKJ2*01 | [6.3.9] |
| 101 | IGKV1D-16*01 | 100.00% (279/279 nt) | IGKJ2*01 | [6.3.10] |
| 025 | IGKV3-11*01 | 100.00% (279/279 nt) | IGKJ4*01 | [6.3.9] |
| 109 | IGKV3-11*01 | 99.64% (278/279 nt) | IGKJ4*01 | [6.3.9] |
| 017 | IGKV3-20*01 | 99.29% (280/282 nt) | IGKJ1*01 | [7.3.9] |
| 114 | IGKV3-20*01 | 99.65% (281/282 nt) | IGKJ4*01 | [7.3.8] |

References to the Sequence Listing:

| VH-region | |
|---|---|
| SEQ ID No: 1 | VH 013 |
| SEQ ID No: 2 | VH 013, CDR1 |
| SEQ ID No: 3 | VH 013, CDR2 |
| SEQ ID No: 4 | VH 013, CDR3 |
| SEQ ID No: 5 | VH 114 |
| SEQ ID No: 6 | VH 114, CDR1 |
| SEQ ID No: 7 | VH 114, CDR2 |
| SEQ ID No: 8 | VH 114, CDR3 |
| SEQ ID No: 9 | VH 011 |
| SEQ ID No: 10 | VH 011, CDR1 |
| SEQ ID No: 11 | VH 011, CDR2 |
| SEQ ID No: 12 | VH 011, CDR3 |
| SEQ ID No: 13 | VH 017-D12 |
| SEQ ID No: 14 | VH 017-D12, CDR1 |
| SEQ ID No: 15 | VH 017-D12, CDR2 |
| SEQ ID No: 16 | VH 017-D12, CDR3 |
| SEQ ID No: 17 | VH 042 |
| SEQ ID No: 18 | VH 042, CDR1 |
| SEQ ID No: 19 | VH 042, CDR2 |
| SEQ ID No: 20 | VH 042, CDR3 |
| SEQ ID No: 21 | VH 092-A09 |
| SEQ ID No: 22 | VH 092-A09, CDR1 |
| SEQ ID No: 23 | VH 092-A09, CDR2 |
| SEQ ID No: 24 | VH 092-A09, CDR3 |
| SEQ ID No: 25 | VH 101 |
| SEQ ID No: 26 | VH 101, CDR1 |
| SEQ ID No: 27 | VH 101, CDR2 |
| SEQ ID No: 28 | VH 101, CDR3 |
| SEQ ID No: 29 | VH 003 |
| SEQ ID No: 30 | VH 003, CDR1 |
| SEQ ID No: 31 | VH 003, CDR2 |
| SEQ ID No: 32 | VH 003, CDR3 |
| SEQ ID No: 33 | VH 025 |
| SEQ ID No: 34 | VH 025, CDR1 |
| SEQ ID No: 35 | VH 025, CDR2 |
| SEQ ID No: 36 | VH 025, CDR3 |

TABLE 1A

Heavy chain homologies

| Ab | V-GENE and allele | V-REGION Identity, % | J-GENE and allele | D-GENE and allele | CDR-IMGT lengths |
|---|---|---|---|---|---|
| 003 | IGHV1-69*02, or IGHV1-69*04 | 97.57% (281/288 nt) | IGHJ4*02 | IGHD6-13*01 | [8,8,11] |
| 098 | IGHV1-69*04 | 95.49% (275/288 nt) | IGHJ3*02 | IGHD2-21*02 | [8,8,11] |
| 011 | IGHV3-23*01 | 96.53% (278/288 nt) | IGHJ4*02 | IGHD1-26*01 | [8,8,11] |
| 017 | IGHV3-23*01 | 98.26% (283/288 nt) | IGHJ2*01 | IGHD2-15*01 | [8,8,13] |
| 092 | IGHV3-23*01 | 97.92% (282/288 nt) | IGHJ4*02 | IGHD7-27*01 | [8,8,11] |
| 101 | IGHV3-23*01 | 95.83% (276/288 nt) | IGHJ4*02 | IGHD7-27*01 | [8,8,11] |
| 025 | IGHV3-30-3*01 | 97.57% (281/288 nt) | IGHJ4*02 | IGHD7-27*01 | [8,8,13] |
| 109 | IGHV3-30-3*01 | 96.18% (277/288 nt) | IGHJ4*02 | IGHD7-27*01 | [8,8,13] |
| 111 | IGHV3-30-3*01 | 97.57% (281/288 nt) | IGHJ4*02 | IGHD3-10*01 | [8,8,13] |
| 114 | IGHV3-33*01, or IGHV3-33*03 | 94.44% (272/288 nt) | IGHJ6*02 | IGHD3-10*01 | [8,8,12] |
| 013 | IGHV5-51*01 | 99.65% (287/288 nt) | IGHJ3*02 | IGHD6-13*01 | [8,8,19] |

-continued

| | |
|---|---|
| SEQ ID No: 37 | VH 109 |
| SEQ ID No: 38 | VH 109, CDR1 |
| SEQ ID No: 39 | VH 109, CDR2 |
| SEQ ID No: 40 | VH 109, CDR3 |
| SEQ ID No: 41 | VH 044 |
| SEQ ID No: 42 | VH 044, CDR1 |
| SEQ ID No: 43 | VH 044, CDR2 |
| SEQ ID No: 44 | VH 044, CDR3 |
| SEQ ID No: 45 | VH 087-Lg6 |
| SEQ ID No: 46 | VH 087-Lg6, CDR1 |
| SEQ ID No: 47 | VH 087-Lg6, CDR2 |
| SEQ ID No: 48 | VH 087-Lg6, CDR3 |
| SEQ ID No: 49 | VH 098 |
| SEQ ID No: 50 | VH 098, CDR1 |
| SEQ ID No: 51 | VH 098, CDR2 |
| SEQ ID No: 52 | VH 098, CDR3 |
| SEQ ID No: 53 | VH 111 |
| SEQ ID No: 54 | VH 111, CDR1 |
| SEQ ID No: 55 | VH 111, CDR2 |
| SEQ ID No: 56 | VH 111, CDR3 |
| VL-region | |
| SEQ ID No: 57 | VL 013 |
| SEQ ID No: 58 | VL 013, CDR1 |
| SEQ ID No: 59 | VL 013, CDR2 |
| SEQ ID No: 60 | VL 013, CDR3 |
| SEQ ID No: 61 | VL 114 |
| SEQ ID No: 62 | VL 114, CDR1 |
| SEQ ID No: 63 | VL 114, CDR2 |
| SEQ ID No: 64 | VL 114, CDR3 |
| SEQ ID No: 65 | VL 011 |
| SEQ ID No: 66 | VL 011, CDR1 |
| SEQ ID No: 67 | VL 011, CDR2 |
| SEQ ID No: 68 | VL 011, CDR3 |
| SEQ ID No: 69 | VL 017-D12 |
| SEQ ID No: 70 | VL 017-D12, CDR1 |
| SEQ ID No: 71 | VL 017-D12, CDR2 |
| SEQ ID No: 72 | VL 017-D12, CDR3 |
| SEQ ID No: 73 | VL 042 |
| SEQ ID No: 74 | VL 042, CDR1 |
| SEQ ID No: 75 | VL 042, CDR2 |
| SEQ ID No: 76 | VL 042, CDR3 |
| SEQ ID No: 77 | VL 092-A09 |
| SEQ ID No: 78 | VL 092-A09, CDR1 |
| SEQ ID No: 79 | VL 092-A09, CDR2 |
| SEQ ID No: 80 | VL 092-A09, CDR3 |
| SEQ ID No: 81 | VL 101 |
| SEQ ID No: 82 | VL 101, CDR1 |
| SEQ ID No: 83 | VL 101, CDR2 |
| SEQ ID No: 84 | VL 101, CDR3 |
| SEQ ID No: 85 | VL 003 |
| SEQ ID No: 86 | VL 003, CDR1 |
| SEQ ID No: 87 | VL 003, CDR2 |
| SEQ ID No: 88 | VL 003, CDR3 |
| SEQ ID No: 89 | VL 025 |
| SEQ ID No: 90 | VL 025, CDR1 |
| SEQ ID No: 91 | VL 025, CDR2 |
| SEQ ID No: 92 | VL 025, CDR3 |
| SEQ ID No: 93 | VL 109 |
| SEQ ID No: 94 | VL 109, CDR1 |
| SEQ ID No: 95 | VL 109, CDR2 |
| SEQ ID No: 96 | VL 109, CDR3 |
| SEQ ID No: 97 | VL 044 |
| SEQ ID No: 98 | VL 044, CDR1 |
| SEQ ID No: 99 | VL 044, CDR2 |
| SEQ ID No: 100 | VL 044, CDR3 |
| SEQ ID No: 101 | VL 087 |
| SEQ ID No: 102 | VL 087, CDR1 |
| SEQ ID No: 103 | VL 087, CDR2 |
| SEQ ID No: 104 | VL 087, CDR3 |
| SEQ ID No: 105 | VL 098 |
| SEQ ID No: 106 | VL 098, CDR1 |
| SEQ ID No: 107 | VL 098, CDR2 |
| SEQ ID No: 108 | VL 098, CDR3 |
| SEQ ID No: 109 | VL 111 |
| SEQ ID No: 110 | VL 111, CDR1 |
| SEQ ID No: 111 | VL 111, CDR2 |
| SEQ ID No: 112 | VL 111, CDR3 |

Example 11

Purification of Antibodies

Culture supernatant was filtered over 0.2 µm dead-end filters and loaded on 5 ml Protein A columns (rProtein A FF, Amersham Bioscience) and eluted with 0.1 M citric acid-NaOH, pH 3. The eluate was immediately neutralized with 2M Tris-HCl, pH 9 and dialyzed overnight to 12.6 mM $NaH_2PO_4$, 140 mM NaCl, pH 7.4 (B. Braun). After dialysis samples were sterile filtered over 0.2 µm dead-end filters. Purity was determined by SDS-PAGE and concentration was measured by nephelometry and absorbance at 280 nm. Purified antibodies were aliquoted and stored at −80° C. Once thawed, purified antibody aliquots were kept at 4° C. Mass spectrometry was performed to identify the molecular mass of the antibody heavy and light chains expressed by the hybridomas as described in Example 9.

Example 12

Antibody Cross-Competition Studies Using Sandwich-ELISA

ELISA plate wells were coated overnight at +4° C. with each of the anti-TF HuMabs (0.5 or 2 µg/ml 100 µL/well) diluted in PBS. The ELISA wells were washed with PBS, blocked for one hour at room temperature with 2% (v/v) chicken serum (Gibco, Paisley, Scotland) in PBS and washed again with PBS. Subsequently, 50 µL anti-TF HuMab (10 µg/mL) followed by 50 µL TFECDHis (0.5 or 1 µg/ml) (generated at Genmab; Example 5) was added, and incubated for 1 hour at RT (while shaking). Plates were washed 3 times with PBST (PBS+0.05% tween), and incubated with 1:2000 diluted anti-his biotin BAM050 for one hour at RT (while shaking). Plates were washed and incubated with Streptavidin-poly-HRP (Sanquin, Amsterdam, The Netherlands) for 20 minutes at RT, and washed again. The reaction was further developed with ABTS (Roche Diagnostics) at RT in the dark, stopped after 15 minutes by adding 2% (w/v) oxalic acid and the absorbance at 405 nm was measured.

Table 2 shows that 3 cross-block groups (groups of antibodies competing with each other for TFECDHis binding) could be identified, with antibodies 013, 044 and 087-Lg6 belonging to one cross-block group (group I), antibodies 011, 017-D12, 42, 092-A09 and 101 belonging to another cross-block group (group II), and antibodies 003, 025, 109 and 111 belonging to a third cross-block group (group III). Antibody 114 was found to compete for TFECDHis binding with antibodies from both cross-block group II and III. Antibody 098 binding to TFECDHis could be competed for by antibodies from both cross-block group II and III.

TABLE 2

Competition of anti-TF antibodies for binding to TFECDHis.

| | I | | | II | | | | |
|---|---|---|---|---|---|---|---|---|
| | 0.5 ug coat | 2 ug coat | 2 ug coat | 0.5 ug coat | 0.5 ug coat | 0.5 ug coat | 0.5 ug coat | 0.5 ug coat |
| competitor antibody (10 ug/ml) | 13 | 44 | 087-Lg6 | 11 | 017-D12 | 42 | 092-A09 | 101 |
| 13 | 19 | 5 | 28 | 101 | 100 | 98 | 110 | 98 |
| 44 | 93 | 40 | 29 | 109 | 96 | 96 | 103 | 103 |
| 087-Lg6 | 91 | 54 | 41 | 103 | 93 | 95 | 109 | 93 |
| 11 | 96 | 143 | 929 | 20 | 34 | 35 | 21 | 23 |
| 017-D12 | 97 | 143 | 995 | 14 | 25 | 20 | 8 | 12 |
| 42 | 99 | 143 | 931 | 18 | 28 | 27 | 10 | 17 |
| 002-A09 | 95 | 143 | 995 | 22 | 37 | 37 | 32 | 24 |
| 101 | 96 | 100 | 714 | 10 | 15 | 15 | 10 | 12 |
| 114 | 101 | 143 | 995 | 21 | 34 | 34 | 19 | 22 |
| 98 | 95 | 143 | 995 | 90 | 93 | 97 | 91 | 86 |
| 3 | 84 | 118 | 770 | 100 | 95 | 91 | 96 | 88 |
| 25 | 102 | 143 | 995 | 117 | 96 | 108 | 111 | 100 |
| 109 | 96 | 143 | 995 | 101 | 100 | 101 | 99 | 102 |
| 111 | 89 | 143 | 995 | 110 | 93 | 102 | 95 | 108 |

| | II/III | | III | | | |
|---|---|---|---|---|---|---|
| | 0.5 ug coat | 2 ug coat | 0.5 ug coat | 0.5 ug coat | 0.5 ug coat | 2 ug coat |
| competitor antibody (10 ug/ml) | 114 | 98 | 3 | 25 | 109 | 111 |
| 13 | 105 | 320 | 85 | 85 | 110 | 175 |
| 44 | 105 | 330 | 80 | 108 | 94 | 175 |
| 087-Lg6 | 107 | 210 | 88 | 105 | 103 | 115 |
| 11 | 19 | 9 | 103 | 104 | 109 | 175 |
| 017-D12 | 9 | 9 | 100 | 108 | 97 | 175 |
| 42 | 24 | 8 | 98 | 93 | 111 | 155 |
| 092-A09 | 22 | 10 | 103 | 108 | 101 | 175 |
| 101 | 11 | 7 | 96 | 108 | 106 | 118 |
| 114 | 13 | 9 | 100 | 47 | 26 | 5 |
| 98 | 94 | 24 | 103 | 94 | 86 | 35 |
| 3 | 102 | 10 | 33 | 22 | 10 | 6 |
| 25 | 28 | 10 | 48 | 34 | 11 | 6 |
| 109 | 44 | 9 | 62 | 51 | 17 | 6 |
| 111 | 99 | 37 | 89 | 104 | 82 | 43 |

White boxes indicate no competition for binding, light grey boxes indicate partial competition for binding, and dark grey boxes indicate competition for binding to TFECDHis.

Example 13

Binding of Anti-TF HuMabs to the Extracellular Domain of TF in ELISA

The specificity of the obtained anti-TF HuMabs was evaluated by ELISA. ELISA plates (Microlon®; Greiner Bio-One) were coated overnight at +4° C. with 0.5 µg/mL of TFECDHis in PBS, pH 7.4. Coated ELISA plates were emptied and blocked for one hour at room temperature with 2% (v/v) chicken serum (Gibco, Paisley, Scotland) in PBS and washed with PBS containing 0.05% Tween 20 (PBST). Subsequently, HuMabs, serially diluted in PBSTC (PBS supplemented with 2% (v/v) chicken serum and 0.05% (v/v) Tween-20), were incubated for 1 hr at RT under shaking conditions (300 rpm). Bound HuMabs were detected using HRP-conjugated goat-anti-human IgG antibodies (Jackson ImmunoResearch) diluted 1:5,000 in PBSTC, which were incubated for 1 hr at RT under shaking conditions (300 rpm). The reaction was further developed with ABTS (Roche Diagnostics) at RT in the dark, stopped after 15-30 minutes by adding 2% (w/v) oxalic acid and then the absorbance at 405 nm was measured. HuMab-KLH (a human monoclonal antibody against KLH (keyhole limpet haemocyanin>>, was used as a negative control. Mouse anti-human TF (ERL) was used as positive control (HRP labeled anti-mouse IgG as conjugate). Binding curves were analyzed using non-linear regression (sigmoidal dose-response with variable slope) using GraphPad Prism V4.03 software.

As can been seen in FIG. 3, all of the anti-TF antibodies bound TFECDHis. The $EC_{50}$ values for the HuMabs are the mean of 3 experiments and varied between 0.09 and 0.46 nM (Table 3 below).

TABLE 3

| group | HuMab TF | EC50 nM |
|---|---|---|
| I | 13 | 0.24 |
| I | 44 | 0.14 |
| I | 87-Lg6 | 0.09 |
| II | 11 | 0.16 |
| II | 017-D12 | 0.25 |
| II | 42 | 0.23 |

TABLE 3-continued

| group | HuMab TF | EC50 nM |
|---|---|---|
| II | 092-A09 | 0.18 |
| II | 101 | 0.28 |
| II/III | 98 | 0.13 |
| II/III | 114 | 0.17 |
| III | 3 | 0.46 |
| III | 25 | 0.34 |
| III | 109 | 0.27 |
| III | 111 | 0.11 |

Example 14

Binding of Anti-TF HuMabs to Membrane-Bound TF

Binding of anti-TF HuMabs to membrane-bound TF was determined by FACS analysis, using TF transfected CHO cells, or TF expressing tumor cell lines MDA-MB-231, (luciferase transfected) A431 and Bx-PC3.

Cells were resuspended in PBS ($2 \times 10^6$ cells/ml), put in 96-well V-bottom plates (50 µl/well). 50 µl of serially diluted HuMab in FACS buffer (PBS supplemented with 0.1% BSA and 0.02% Na-azide) was added to the cells and incubated for 30 minutes on ice. After washing three times with FACS buffer, 50 µl of phycoerythrin (PE)-conjugated goat anti-human IgGFc (Jackson ImmunoResearch), diluted 1:100 in FACS buffer, was added. After 30 minutes on ice (in the dark), cells were washed three times, and specific binding of the HuMabs was detected by flow cytometry on a FACSCalibur™ (BD Biosciences). HuMab-KLH was used as a negative control. Mouse anti-TF followed by PE-conjugated anti-mouse IgGFc was used as positive control. Binding curves were analyzed using non-linear regression (sigmoidal dose-response with variable slope) using GraphPad Prism V4.03 software (GraphPad Software, San Diego, Calif., USA).

FIG. 4 shows an example of binding curves of TF-specific HuMabs to MDA-MB-231 cells. Table 4 gives an overview of EC50 values of binding of TF-specific HuMabs to TF transfected CHO cells (S1015-TF), MDA-MB-231, A431 and Bx-PC3 cells.

TABLE 4

Overview of EC50 and maximum mean fluorescence index (max MFI) values determined by FACS analysis of binding of TF-specific HuMabs to different cell types.

| | | MDA-MB-231 | | Bx-PC3 | | A431 | | S1015-TF-012 | |
|---|---|---|---|---|---|---|---|---|---|
| group | HuMab TF | EC50 | Max MFI | EC50 | Max MFI | EC50 | Max MFI | EC50 | Max MFI |
| I | 13 | 1.58 | 2451 | 1.86 | 1305 | 8.04 | 3622 | 1.07 | 5207 |
| I | 44 | 0.87 | 1881 | 1.88 | 1136 | 1.45 | 2646 | 2.13 | 5021 |
| I | 87-Lg6 | 8.28 | 1107 | 7.19 | 1030 | nt | nt | nt | nt |
| II | 11 | 0.47 | 2143 | 1.01 | 1280 | 0.20 | 2606 | 1.32 | 5654 |
| II | 017-D12 | 1.33 | 2401 | 1.61 | 1422 | 1.24 | 3296 | 1.21 | 5792 |
| II | 42 | 0.25 | 1518 | 2.45 | 1701 | nt | nt | nt | nt |
| II | 092-A09 | 0.53 | 2290 | 0.84 | 1262 | 0.83 | 3137 | 1.32 | 5409 |
| II | 101 | 0.85 | 2071 | 2.25 | 1220 | 3.16 | 2934 | 1.77 | 5859 |
| II/III | 98 | 0.99 | 1956 | 1.38 | 1151 | 1.40 | 2755 | 0.96 | 5229 |
| II/III | 114 | 0.47 | 2438 | 0.80 | 1407 | 0.90 | 3433 | 1.72 | 6095 |
| III | 3 | 3.20 | 1798 | 4.98 | 1106 | 6.94 | 2530 | 2.06 | 4247 |
| III | 25 | 0.69 | 2254 | 0.88 | 1320 | 5.19 | 3170 | 0.73 | 5808 |
| III | 109 | 2.16 | 2052 | 4.04 | 1324 | 1.74 | 3124 | 0.92 | 5629 |
| III | 111 | 1.03 | 1774 | 1.83 | 1128 | 2.88 | 3043 | 0.55 | 5353 |

EC50 values are in mM. Max MFI for MDA-MB-231, BxPC3 and A431 cells at 30 µg/mL antibody, for S1015-TF at 7.5 µg/mL antibody.

EC50 values are in nM. Max MFI for MDA-MB-231, BxPC3 and A431 cells at 30 µg/mL antibody, for S1015-TF at 7.5 µg/mL antibody.

Example 15

Inhibition of FVIIa Binding to TF

Inhibition of binding of FVIIa to TFECDHis by TF-HuMabs was measured by ELISA. ELISA plates were coated overnight with TFECDHis (0.5 µg/mL, 100 µL per well). Plates were emptied, blocked with PBS containing 2% (v/v) chicken serum (1 hour, RT), and emptied again. 4-fold serial dilutions of TF-HuMabs or HuMab-KLH (negative control) were added to the wells followed by FVIIa at EC50 concentration (100 nM), and plates incubated for 1 hour at RT (while shaking, 300 rpm). Plates were washed and incubated with rabbit-anti-FVIIa (2.5 µg/mL; Abcam) as above. Plates were washed and incubated with swine-anti-rabbit IgG-HRP antibody (1:2,500; DAKO). After washing, the immune complexes were visualized using ABTS as a substrate. The reaction was stopped by the addition of 2% v/v oxalic acid followed by optical density measurement at 405 nm using an ELISA reader. The concentration of antibody needed to obtain 50% inhibition (IC50) was calculated using GraphPad prism (non linear regression analysis).

FIG. 5 shows that antibodies from cross-block groups II and III efficiently inhibited FVIIa binding to TF, while antibodies from cross-block group I did not (or to a much lesser extent) inhibited FVIIa binding.

Table 5 shows IC50 values and maximum inhibition values (percentage) of inhibition of FVIIa binding to TF by TF-specific HuMabs.

TABLE 5

IC50 values and maximum inhibition values (percentage) of inhibition of FVIIa binding to TF by TF-specific HuMabs

| group | HuMab TF | IC50 nM | max inhibition |
|---|---|---|---|
| I | 13 | 19.3 | 27 |
| I | 44 | 0.8 | 54 |
| I | 87-Lg6 | na | 35 |

TABLE 5-continued

IC50 values and maximum inhibition values (percentage) of inhibition of
FVIIa binding to TF by TF-specific HuMabs

| group | HuMab TF | IC50 nM | max inhibition |
|---|---|---|---|
| II | 11 | 1.1 | 91 |
| II | 017-D12 | 1.9 | 90 |
| II | 42 | 2.7 | 88 |
| II | 092-A09 | 1.5 | 90 |
| II | 101 | 0.6 | 84 |
| II/III | 98 | 0.8 | 85 |
| II/III | 114 | 1.3 | 90 |
| III | 3 | 1.9 | 89 |
| III | 25 | 2.1 | 90 |
| III | 109 | 1.7 | 90 |
| III | 111 | 1.7 | 79 |

Example 16

Inhibition of FVIIa Induced ERK Phosphorylation

Upon binding of coagulation factor VIIa (FVIIa) to TF, phosphorylation of mitogen activated kinase (p42 and p44 MAPK or ERK1 and ERK2) is triggered. The epidermoid carcinoma cell line A431 expresses high levels of TF, and after stimulation with FVIIa an optimal (3 to 5 fold) ERK phosphorylation (ERK-P), measured using the AlphaScreen Surefire ERK assay (Perkin Elmer), is induced within 10 minutes.

A431 cells (30,000 cells per well) were seeded in 96 well TC plates, and cultured O/N (37° C., 5% $CO_2$, 85% humidity) in serum-free medium (RPMI containing 20% HSA and penicillin/streptomycin). Medium was then replaced by DMEM (without additives) and cells were incubated for 1.5 hours. 3 fold serial dilutions of TF-HuMabs or HuMab-KLH were added and cells incubated for 0.5 hours. Cells were then stimulated with FVIIa at EC80 concentration (50 nM; 10 minutes; 37° C., 5% $CO_2$, 85% humidity). Cells were washed once with PBS, and lysed using 25 µL lysis buffer (Perkin Elmer, Surefire™ kit). Lysates were centrifuged (3 minutes, 330×g, RT). Four µL of supernatant was transferred to 384 well Proxiplates (Perkin Elmer). 7 µl Reaction buffer/Activation buffer mix containing AlphaScreen® beads (Perkin Elmer Surefire kit) was added, and plates were incubated in the dark for 2 hours at RT. Plates were read using the "Surefire® Plus" protocol from EnVision technology.

FIG. 6 shows that, measured using the AlphaScreen Surefire ERK assay, antibody 013 does not inhibit FVIIa induced ERK phosphorylation, 044 and 111 moderately inhibit ERK phosphorylation, and all other antibodies efficiently block ERK phosphorylation.

Table 6 shows IC50 values and maximum inhibition values (percentage) of inhibition of FVIIa induced ERK phosphorylation by TF-specific HuMabs, measured using the AlphaScreen Surefire ERK assay.

TABLE 6

IC50 values and maximum inhibition values (percentage) of inhibition of
FVIIa induced ERK phosphorylation (measured using the AlphaScreen
Surefire ERK assay) by TF-specific HuMabs.

| group | HuMab TF | IC50 nM | % max inhibition |
|---|---|---|---|
| I | 13 | 9.11 | 26 |
| I | 44 | >66.6 | 45 |
| I | 87-Lg6 | nt | nt |
| II | 11 | 0.79 | 69 |

TABLE 6-continued

IC50 values and maximum inhibition values (percentage) of inhibition of
FVIIa induced ERK phosphorylation (measured using the AlphaScreen
Surefire ERK assay) by TF-specific HuMabs.

| group | HuMab TF | IC50 nM | % max inhibition |
|---|---|---|---|
| II | 017-D12 | 2.01 | 65 |
| II | 42 | nt | nt |
| II | 092-A09 | 1.27 | 68 |
| II | 101 | 1.05 | 57 |
| II/III | 98 | 1.89 | 64 |
| II/III | 114 | 1.08 | 68 |
| III | 3 | 7.99 | 63 |
| III | 25 | 2.16 | 66 |
| III | 109 | 2.42 | 72 |
| III | 111 | >66.6 | 52 |

The results obtained in the AlphaScreen Surefire ERK assay were confirmed by Western Blot analysis, using HaCaT and BxPC3 cell lines. 30,000 cells/well were seeded in DMEM containing minimal concentrations of serum (starvation medium), and cultured overnight. Cells were further cultured for 2 hours in DMEM without serum, anti-TF antibodies were added during the final 30 minutes of culture. Cell were stimulated with 0, 10 or 50 nM FVIIa for 10 minutes (37° C.), and subsequently lysed in cell lysis buffer (50 µL lysis buffer per well, 30-60 minutes lysis under shaking condition, RT). 25 µL SDS containing sample buffer was added to each sample. Samples were loaded onto SDS-PAGE gels, run and blotted using standard procedures for Western blotting. Blots were blocked with TBST1x containing 5% irrelevant protein (ELK) for 1 hour at RT. Blots were incubated with rabbit anti-ERK-P antibody (O/N, 4° C.). Blots were washed with TBST1x, and incubated with anti-rabbit IgG HRP (1 hour, RT), washed, developed using HRP substrate and imaged using Optigo Ultima Imaging system (Isogen Life Sciences).

FIG. 6A shows the results in BxPC3 cells for a sub-panel of antibodies. ERK phosphorylation induced by 10 nM of FVIIa was not inhibited by antibody 013, while it was efficiently inhibited by antibodies 111, 044 and 025 (the latter as an example for all other TF-specific HuMabs described here). Stronger induced ERK phosphorylation (50 nM FVIIa) was not inhibited by antibodies 013, 111 and 044, but was inhibited by antibody 025.

Example 17

Inhibition of FVIIa induced IL-8 Release

The ability of TF specific HuMabs to inhibit FVIIa induced release of IL-8 was tested using MDA-MB-231 cells. Cells were seeded into 96 well plates (60,000 cells/well) and cultured (O/N, 37° C., 5% $CO_2$) in DMEM containing CS, sodium pyruvate, I-glutamine, MEM NEAA and penicillin/streptomycin. Tissue culture medium was removed, cells were washed twice in serum free, high calcium medium (DMEM containing penicillin/streptomycin), and cultured in this medium for an additional 105 minutes. Serial dilutions of antibodies were added, and cells cultured for 15 minutes. FVIIa (Novo Nordisk; final concentration 10 nM) was added and cells were cultured for 5 hours. Supernatant was removed and centrifuged (300×g, RT). IL-8 concentrations in the supernatant were measured using an IL-8 ELISA kit according to the manufacturer's protocol (Sanquin).

FIG. 7 shows that antibodies from cross-block groups II and III efficiently inhibited FVIIa induced IL-8 release by MDA-MB-231 cells, with the exception of antibody 111 from cross-block group III. Antibodies from cross-block group I (013, 044 and 87-Lg6) all did not inhibit FVIIa induced IL-8 release.

Table 7 shows IC50 values and maximum inhibition values (percentage) of inhibition of FVIIa induced IL-8 release by TF-specific HuMabs.

TABLE 7

IC50 values and maximum inhibition values (percentage) of inhibition of FVIIa induced IL-8 release by TF-specific HuMabs.

| group | HuMab TF | IC50 nM | max inhibition |
|---|---|---|---|
| I | 13 | na | −0.3 |
| I | 44 | 74.6 | 17.2 |
| I | 87-Lg6 | na | 4.3 |
| II | 11 | 9.4 | 61.7 |
| II | 017-D12 | 9.0 | 65.8 |
| II | 42 | 14.9 | 53.7 |
| II | 092-A09 | 28.2 | 66.6 |
| II | 101 | 22.7 | 74.9 |
| II/III | 98 | 9.3 | 59.0 |
| II/III | 114 | 9.2 | 71.5 |
| III | 3 | 23.7 | 76.2 |
| III | 25 | 23.1 | 75.6 |
| III | 109 | 13.6 | 70.4 |
| III | 111 | >200 | 40.1 |

Example 18

Inhibition of FXa Generation

The ability of TF specific HuMabs to inhibit FXa generation was tested in an assay in which conversion of FX into FXa by the TF/FVIIa complex is measured using a colometric FXa specific substrate. TF (Innovin®) was added to flatbottom 96 well plates, together with a serial dilution of TF specific HuMabs, positive control (mouse anti-TF) of negative control (HuMab-KLH)(all diluted in Hepes buffer containing 3 mM $CaCl_2$. Plates were incubated for 30 minutes at RT, and FVIIa (final concentration 1 nM) and FX (ERL; final concentration 200 nM) was added. Plates were incubated 30 minutes at 37° C. 50 µl from each well was transferred to a 96 well plate containing (pre-heated, 37° C.) stop-buffer (5 mM EOTA in 100 ml Hepes buffer). FXa specific substrate Chromogenix-2765 (Instrumation Laboratory Company) was added, plates incubated for 60 minutes at 37° C. and OD405 nm at 37° C. was measured.

FIG. 8 shows that antibody 017-D12 strongly inhibited FXa generation, 013 demonstrated intermediate inhibition and other antibodies showed low to no inhibition of FXa generation.

Table 8 shows IC50 values and maximum inhibition values (percentage) of inhibition of FXa generation by TF-specific HuMabs.

TABLE 8

IC50 values and maximum inhibition values (percentage) of inhibition of FXa generation by TF-specific HuMabs.

| group | HuMab TF | IC50 nM | % max inhibition |
|---|---|---|---|
| I | 13 | 0.05 | 31 |
| I | 44 | NA | 3 |
| I | 87-Lg6 | nt | nt |
| II | 11 | 0.05 | 26 |
| II | 017-D12 | 0.28 | 84 |
| II | 42 | nt | nt |

TABLE 8-continued

IC50 values and maximum inhibition values (percentage) of inhibition of FXa generation by TF-specific HuMabs.

| group | HuMab TF | IC50 nM | % max inhibition |
|---|---|---|---|
| II | 092-A09 | 0.30 | 21 |
| II | 101 | nt | nt |
| II/III | 98 | 0.43 | 14 |
| II/III | 114 | 0.24 | 21 |
| III | 3 | 0.07 | 21 |
| III | 25 | 0.30 | 19 |
| III | 109 | 0.09 | 18 |
| III | 111 | 0.07 | 7 |

Example 19

Inhibition of Blood Coagulation

Inhibition of blood coagulation by TF-HuMabs was measured in an assay determining TF induced clotting time. Mixtures of 17 µl 100 mM $CaCl_2$ (final conc. 17 mM), 10 µl 1:100 innovin (final conc. 1:1000), 23 µl 1×HEPES-buffer and 50 µl serially diluted antibody were prepared in 96 well plates. Fifty µl pooled human plasma was added to wells of Immulon 2B plates (Thermo Electron). Fifty µl of the prepared antibody mixtures was added to the Immulon 2b plates, and coagulation development at 405 nm was measured every 15 sec for 25 min using a kinetic plate reader. The increase in optical density was plotted in time and clotting time (t1/2) was calculated. Clotting time was plotted against antibody concentration. IC50 of antibody induced inhibition of coagulation was calculated from this by non linear regression analysis using GraphPad Prism.

FIG. 9 shows that antibody 044, 087 and 111 did not inhibit TF induced blood coagulation, whereas all other antibodies did.

Table 9 shows IC50 values of inhibition of blood coagulation by TF-specific HuMabs.

TABLE 9

IC50 values of inhibition of blood coagulation by TF-specific HuMabs.

| group | HuMab TF | IC50 nM |
|---|---|---|
| I | 13 | 0.6 |
| I | 44 | NA |
| I | 87-Lg6 | NA |
| II | 11 | 1.6 |
| II | 017-D12 | 2.6 |
| II | 42 | 1.5 |
| II | 092-A09 | 0.2 |
| II | 101 | 0.7 |
| II/III | 98 | 1.1 |
| II/III | 114 | 0.4 |
| III | 3 | 7.3 |
| III | 25 | 2.3 |
| III | 109 | 7.6 |
| III | 111 | NA |

Example 20

Antibody-Dependent Cell-Mediated Cytotoxicity

Preparation of Target Cells:

TF expressing target cells ($5 \times 10^6$ Bx-PC3 cells, MDA-MB-231 cells or A431 cells) were harvested, washed (twice in PBS, 1500 rpm, 5 min) and collected in 1 ml RPMI 1640 culture medium supplemented with Cosmic Calf Serum, Sodium Pyruvate, L-Glutamine, MEM NEAA and Penicillin/Streptomycin, to which 100 μCi $^{51}$Cr (Chromium-51; Amersham Biosciences Europe GmbH, Roosendaal, The Netherlands) was added. The mixture was incubated in a shaking water bath for 1 hr at 37° C. After washing of the cells (twice in PBS, 1500 rpm, 5 min), the cells were resuspended in culture medium and viable cells counted by trypan blue exclusion. Viable cells were brought to a concentration of 1×10$^5$ cells/ml.

Preparation of Effector Cells:

Peripheral blood mononuclear cells (PBMCs) were isolated from fresh buffy coats (Sanquin, Amsterdam, The Netherlands) using standard Ficoll density centrifugation according to the manufacturer's instructions (lymphocyte separation medium; Lonza, Verviers, France). After resuspension of cells in culture medium, cells were counted by trypan blue exclusion and brought to a concentration of 1×10$^7$ cells/ml.

ADCC Set Up:

50 μl of $^{51}$Cr-labeled targets cells were transferred to microtiter wells, and 50 μl of serially diluted antibody was added, diluted in culture medium. Cells were incubated (RT, 15 min), and 50 μl effector cells were added, resulting in an effector to target ratio of 100:1. To determine the maximum level of lysis, 100 μl 5% Triton-X100 was added instead of effector cells; to determine the spontaneous level of lysis, 100 μl culture medium was added; to determine the level of antibody independent lysis, 50 μl effector cells and 50 μl culture medium was added). Subsequently, cells were incubated O/N at 37° C., 5% CO$_2$. After spinning down the cells (1200 rpm, 3 min), 75 μl of supernatant was transferred to micronic tubes. The released $^{51}$Cr was counted in a gamma counter and the percentage of antibody mediated lysis was calculated as follows:

((cpm sample−cpm antibody independent lysis)/(cpm maximal lysis−cpm spontaneous lysis))×100% wherein cpm is counts per minute.

FIG. 10 shows that all tested TF-HuMabs induced lysis of Bx-PC3 cells by ADCC, albeit with different efficiencies (EC50).

Table 10 shows EC50 values (nM) of ADCC of different cell lines by TF-specific HuMabs.

TABLE 10

EC50 values (nM) of ADCC of different cell lines by TF-specific HuMabs.

| group | HuMab TF | MDA-MB-231 EC50 | Bx-PC3 EC50 | A431 EC50 |
|---|---|---|---|---|
| I | 13 | 0.06 | 0.07 | 0.11 |
| I | 44 | 0.08 | 0.12 | 0.19 |
| I | 87-Lg6 | nt | nt | nt |
| II | 11 | 0.07 | 0.22 | 0.06 |
| II | 017-D12 | 0.14 | 0.13 | 0.18 |
| II | 42 | nt | nt | nt |
| II | 092-A09 | 0.11 | 0.13 | 0.22 |
| II | 101 | 0.10 | 0.09 | 0.01 |
| II/III | 98 | 0.15 | 0.02 | 0.07 |
| II/III | 114 | 0.07 | 0.07 | 0.08 |
| III | 3 | 0.29 | 0.17 | 0.58 |
| III | 25 | 0.24 | 0.15 | 0.16 |
| III | 109 | 0.12 | 0.06 | 0.13 |
| III | 111 | 0.84 | 0.22 | 1.56 |

Example 21

Complement Deposition

Deposition of complement fragments C3c and C4c to TF-HuMab incubated target cells was measured by FACS analysis. TF expressing target cells (Bx-PC3 or MDA-MB-231 cells) were plated in 96 well round bottom plates (1×10e5 cells/well) in RPMI containing 1% BSA. Antibody (30 μg/mL) was added and cells incubated at RT for 15 minutes. Twenty-five μL pooled human serum was added as a source of complement, heat inactivated human serum was used to determine spontaneous complement binding. Cells were incubated at 37° C. for 45 minutes. Cells were washed once, and incubated with anti-human C3c FITC or anti-human C4c FITC (DAKO) in FACS buffer, and incubated for 30 minutes on ice. Samples were analyzed using FACS Canto™.

FIG. 11 shows that antibodies from cross-block group I did not induce C3c or C4c deposition on either BxPC3 or MDA-MB-231 cells. All tested antibodies from cross-block group II did induce C3c and C4c deposition, as did antibodies from cross-block group III, with the exception of antibody 003.

Example 22

Avidity/Affinity Studies

Determination of Affinity:

Antibody binding to TF was analyzed by surface plasmon resonance in a BIAcore™ 3000 (GE Healthcare). TFECDHis was used for the analysis. HuMab antibodies (500 resonance units) were immobilized on the CM-5 sensor chip according to the procedure recommended by the manufacturer. Briefly, after surface activation by EDC and NHS HuMab antibody was injected over the activated CM-5 surface in 10 mM sodium-acetate, pH ranging from 4.0 to 5.5 at 5 μl/min. followed by 1 M Ethanolamine for deactivation. Concentration series of TFECDHis in HBS-EP buffer were injected over the immobilized antibodies at a flow rate of 30 μl/min for 180 sec. Regeneration of the HuMab surface was performed by injection of 10 mM Glycine-HCl pH 2.0 or 10 mM sodium acetate pH 3.0. Kinetic analysis was performed using double reference subtraction and model 1:1 (langmuir) binding analysis.

Table 11 shows for most HuMabs the determined affinity in (sub) nanomolar range. Not from all antibodies the kinetic parameters could be determined. 044 did give a high variation in off-rates (kd) and had high residuals, which means that the fitting of the curves was not well. 098, 111 and 087-Lg6 had off-rates which where too high for the Biacore 3000 to measure.

TABLE 11

Kinetic constants of TF-HuMabs for reactivity with TFECDHis - affinity measurements.

| group | HuMab TF | affinity nM | ka (1/Ms) | kd (1/s) |
|---|---|---|---|---|
| I | 13 | 2.78 | 5.67E+05 | 1.57E−03 |
| I | 44 | n.a. | 8.77E+04 | variable |
| I | 87-Lg6 | n.a. | 5.91E+05 | n.a. |
| II | 11 | 3.15 | 2.86E+05 | 9.02E−04 |
| II | 017-D12 | 2.55 | 1.02E+05 | 2.59E−04 |
| II | 42 | 4.22 | 1.64E+05 | 6.90E−04 |
| II | 092-A09 | 14.1 | 1.42E+05 | 2.00E−03 |
| II | 101 | 3.4 | 3.18E+05 | 1.07E−03 |
| II/III | 98 | n.a. | 2.90E+05 | n.a. |
| II/III | 114 | 11 | 1.77E+05 | 1.95E−03 |
| III | 3 | 4.51 | 2.33E+05 | 1.26E−03 |

TABLE 11-continued

Kinetic constants of TF-HuMabs for reactivity with TFECDHis - affinity measurements.

| group | HuMab TF | affinity nM | ka (1/Ms) | kd (1/s) |
|---|---|---|---|---|
| III | 25 | 1.97 | 3.29E+05 | 6.50E−04 |
| III | 109 | 4.75 | 1.65E+05 | 7.77E−04 |
| III | 111 | n.a. | 2.13E+05 | n.a. | n.a. not assessable = >$10^{-3}$ sec$^{-1}$

Determination of Avidity:

TF (TFECDHis) binding to TF-specific HuMabs was determined essentially as described above, with TFECDHis being immobilized on the CM-5 sensor chip (300 resonance units), and concentration series of Humab antibodies used for kinetic analysis. Kinetic analysis was performed using double reference subtraction and model 1:1 (langmuir) binding analysis. Table 12 shows avidity measurements for antibodies 11, 98, 109 and 111. Whereas affinity measurements for 98 and 111 indicated high-off rates (beyond the limits of determination by Biacore (i.e. >$10^{-3}$)), avidity determination revealed interaction in the nanomolar range.

TABLE 12

Kinetic constants of TFECDHIS for reactivity with TF-HuMabs - avidity measurements.

| Group | HuMab TF | avidity nM |
|---|---|---|
| II | 11 | 0.47 |
| II/III | 98 | 4.85 |
| III | 109 | 0.01 |
| III | 111 | 0.11 |

Example 23

Immunohistochemical Analysis of Binding to Normal Human Tissues and Pancreatic Tumors Binding of TF-HuMabs to various human tissues known to express TF (colon, heart, kidney, skin, lung and brain) was determined by immunohistochemistry (IHC).

IHC on Frozen Tissue

Frozen tissue sections were cut (4-6 µm thickness) and fixated in acetone. Endogenous tissue peroxidase (PO) was blocked and tissue slides were pre-incubated with normal human serum to prevent aspecific binding of later applied antibodies to endogenous Fc receptors. Mouse-Ab directed against human TF (and negative control mouse Ab) was applied at the tissues at optimal dilution and subsequently detected with Powervision-PO (Goat anti-mouse/-rabbit IgG)-PO. TF-specific HuMabs were coupled to Fab' goat anti-human IgG (Fc)-FITC and thereafter applied to the frozen tissue slides at 3 dilutions, including a pre-determined optimal dilution. Subsequently the HuMab—Fab-FITC complex was detected by rabbit anti-FITC and Powervision-PO. PO activity was visualized with AEC as substrate and nuclei were visualized with hematoxylin. Staining was analyzed by brightfield microscope.

IHC with Mouse Ab on Formalin Fixated and Paraffin Embedded (FFPE) Tissue

FFPE tissue biopsies were cut at 4 µm, de-paraffinized, blocked for endogenous tissue peroxidase and subjected to antigen retrieval (pH6, citrate buffer). Prior to the incubation with the mouse-Ab tissue slides were preincubated in normal human serum to prevent aspecific binding to endogenous Fc receptors. Mouse Ab directed against human TF (and negative control mouse Ab) was applied to the tissue slides at optimal dilution and subsequently detected with Powervision-PO (Goat anti-mouse/-rabbit IgG)-PO. PO activity was visualized with AEC as substrate and nuclei were visualized with hematoxylin. Staining was analyzed by brightfield microscope.

FIG. 12 shows an example of binding of antibody 013 (positive staining), 011 (positive staining), 114 (positive staining) and 111 (intermediate staining) to kidney glomeruli. Antibody 098 and 044 did not bind glomeruli.

Table 13 gives an overview of staining results for all TF-HuMabs in human kidney all tissues examined.

TABLE 13

IHC staining of human glomeruli

| Group | HuMab TF | IHC human glomeruli |
|---|---|---|
| I | 13 | + |
| I | 44 | − |
| I | 87-Lg6 | nt |
| II | 11 | + |
| II | 017-D12 | + |
| II | 42 | nt |
| II | 092-A09 | nt |
| II | 101 | + |
| II/III | 98 | − |
| II/III | 114 | + |
| III | 3 | + |
| III | 25 | nt |
| III | 109 | + |
| III | 111 | +/− |

Table 14 gives an overview of staining results of selected TF-specific HuMabs in human kidney, colon, heart, cerebrum and skin as well as in human pancreatic tumors.

TABLE 14

IHC staining of normal human tissue and pancreatic tumors.

| Ab | Hu Kidney | Hu Colon | Hu Heart | Hu Cerebrum | Hu Skin | panc tumor |
|---|---|---|---|---|---|---|
| 13 | renal corpulus + | basal membrane ++ | − | + | epidermis + | +++ |
| 114 | renal corpulus ++ | basal membrane ++ | − | ++ | epidermis ++ | ++++ |
| 11 | renal corpulus + | basal membrane ++ | − | ++ | n.a. (+) | +++ |
| 44 | − | basal membrane + | − | +/− | n.a. | ++ |
| 98 | − | basal membrane + | − | +/− | n.a. (+) | +++ |
| 111 | renal corpulus +/− | basal membrane + | − | + | n.a. | +++ |

IHC analysis of binding of TF-HuMabs to human pancreatic tumors revealed positive staining for all TF-HuMabs (exemplified in FIG. 13).

Example 24

Treatment of Established MDA-MB-231 Tumor Xenograft in Mammary Fat Pads of SCID Mice The in vivo efficacy of TF-HuMabs was determined in established orthotopic MDA-MB-231 xenograft tumors in SCID mice. 2×10⁶ tumor cells in PBS were injected s.c. in the 2nd mammary fat pad of female SCID mice, followed by treatment with TF-HuMabs or control mAb (HuMab-KLH), starting at a moment that tumor sizes became measurable. Antibodies were injected on day 21 (260 µg/mouse), day 28 (130 µg/mouse) and day 42 (130 µg/mouse). Tumor volume was determined at least 2×/week. Volumes (mm³) were calculated from caliper (PLEXX) measurements as 0.52× (length)×(width).

FIG. 14 shows that antibodies 114, 111, 013, 098, 011 and 044 were all effective in inhibiting growth of established orthotopic MDA-MB-231 tumors.

Example 25

Pilot Repeat Dosing of a TF-Specific HuMab in Cynomolgus Monkeys

To obtain initial information on the toxicology of TF-specific HuMabs, including an assessment of the ability of the antibodies to interfere with the coagulation cascade and hence potentially increase the bleeding risk in exposed animals, a pilot repeat dosing study in cynomolgus monkeys was performed.

Two male and two female cynomolgus monkeys (*Macaca fascicularis*), age approximately 2 years, received intravenous injections of antibody 011:
- day 1 of study: 0 mg/kg (vehicle only)
- day 8: 1 mg/kg; 1 mL/minute
- day 15: 10 mg/kg; 1 mL/minute
- day 22: 100 mg/kg; 1 mL/minute The animals were followed until day 27, at which time point the animals were euthanized for necropsy and histological evaluation of organs.

The main end point of the study were:
- clinical observations: determined daily, signs of bleeding from gums, eyes.
- functional bleeding time and blood loss: determined on days 1, 8, 15 and 22 (1, 24 and 120 h post dosing) and at two pre-trial time points.
- blood/traces of blood/clots: HE stain of all tissues (determined at tissues obtained at final sacrifice)
- blood in urine, feces, vomit: determined daily/weekly.

No apparent toxicity of repeated, increasing dosing of antibody 011 was observed. The animals showed no clinical signs and there was no indication of cytokine release. In addition, there were no apparent clinical signs of a compromised coagulation system or systemic bleedings. At the 1 h post dose time-point, the mean bleeding time on Day 22 was significantly higher than that seen on Day 1 (p=0.012). There were no other statistically significant differences between Days 8, 15 and 22 compared with Day 1. Furthermore, it was found that there was no apparent toxicity to major organs and no adverse hematological effects. The preliminary conclusion on the histological evaluation of tissues from this study is that there were no histology findings in the four treated animals that could be attributed to treatment with the test item.

FIG. 15 shows the individual data points for each animal (duplicate samples) as a function of time. Bleeding time for 4 animals were determined on days 1, 8, 15 and 22 (1, 24 and 120 h) and at two pre-trial time points.

Example 26

Preventive and Therapeutic Treatment of BxPC3 Tumor Xenografts in SCID Mice

The in vivo efficacy of TF-HuMabs in preventive or therapeutic treatment of BxPC3 cell xenografts in SCID mice was determined. 10×10⁶ BxPC3 tumor cells in PBS were injected s.c. in female SCID mice, followed by treatment with TF-HuMabs or control mAb (HuMab-KLH). For preventive treatment, antibodies (400 µg/mouse) were injected i.p. 1 hour after tumor induction. For therapeutic treatment, antibody injection (300 µg/mouse) was started on day 8 after tumor induction, followed by weekly antibody injections (150 µg/mouse). Tumor volume was determined at least 2×/week. Volumes (mm³) were calculated from caliper (PLEXX) measurements as 0.52×(length)×(width)².

FIG. 16 shows that TF-specific HuMabs are capable of preventive as well therapeutic treatment of BxPC3 xenograft tumors.

Example 27

DNA Shuffling Between Murine and Human TF to Determine Domains Important for Binding of Anti-TF HuMabs To determine domains important for binding of anti-TF HuMabs to human TF, DNA shuffling was performed between human and murine TF. Shuffle constructs were prepared from DNA encoding human TF, by replacing human domains with murine domains and from DNA encoding murine TF by replacing murine domains with human domains. If a domain in human TF is important for binding of an anti-TF HuMab, binding will be lost upon replacement of that domain with the murine domain. Human and murine TF are 57% homologous on protein level. FIGS. 17 A and 17 B show the constructs for human TF containing murine TF domains (TFhs, containing TFmm domains) and for murine TF containing human TF domains. HEK293F cells were transiently transfected with the constructs or with the vector alone (pcDNA3.3SP; mock). FACS analysis was performed essentially as described supra, with 30 µg/mL purified parental material. HuMab-KLH was used as a control Ab.

FIG. 17 shows that all but one anti-TF HuMabs bind solely to human TF and not to murine TF. HuMab-TF-003 shows some binding to murine TF.

FIGS. 18 A to O shows the results for binding of the different anti-TF HuMabs to the constructs expressed on HEK293F cells. These results are summarized in Table 15. In this table the anti-TF HuMabs are classified in groups, based on the domains on human TF that are important for binding of these HuMabs.

TABLE 15

| Shuffle constructs: TFhs- | HuMabs that show decreased binding |
|---|---|
| 1-41mm | None |
| 42-84 mm | 11, 17, 42, 92, 98, 101, 111 |
| 85-122 mm | 25, 42, 98, 109, 111 |
| 123-137 mm | 44, 114 |
| 185-225 mm | 13, 27, 44, 87 |
| 226-250 mm | 44 |

TABLE 15-continued

| Groups based on binding to shuffle constructs | HuMabs in the group |
|---|---|
| 1. 42-84 | 11, 17, 92, 101 |
| 2. 42-84 + 85-122 | 42, 98, 111 |
| 3. 85-122 | 25, 109 |
| 4. 123-137 | 114 |
| 5. 185-225 | 13, 27, 87 |
| 6. 123-137 + 185-225 + 226-250 | 44 |

Example 28

Binding of Fab Fragments of Anti-TF HuMabs to the Extracellular Domain of TF, Determined by ELISA, and to Cellular TF on BxPC3 Cells, Determined by FACS Binding of Fab fragments of anti-TF HuMabs to TF was measured by ELISA (coated extracellular domain of TF) and by FACS (TF on BxPC3 cells). ELISA was performed essentially as described supra. Bound Fab fragments were detected using HRP-conjugated donkey-anti human H+L. FACS analysis was performed essentially as described supra. FITC-conjugated goat anti-human IgG (H+L) (Jackson) was used to detect bound lead candidates. Fluorescence was measured on a FACSCantoII. Binding curves were analyzed as described supra, using GraphPad Prism 5 software.

FIG. 19 shows less binding of HuMab-TF-098 and -111 Fab fragments to the extracellular domain of TF, compared to -011 Fab fragments, measured by ELISA.

FIG. 20 shows less binding of HuMab-TF-098 and -111 Fab fragments to cellular TF, compared to -011 Fab fragments, measured by FACS on BxPC3 cells.

Table 16 shows EC50 values of HuMab-TF Fab fragments for binding to the extracellular domain of TF by ELISA and to cellular TF by FACS on BxPC3 cells.

TABLE 16

Overview of EC50 values for binding of HuMab-TF Fab fragments to the extracellular domain of TF, determined by ELISA, and to cellular TF on BxPC3 cells, determined by FACS.

| HuMab-TF | EC50 (ELISA) | EC50 (FACS) |
|---|---|---|
| 011 | 0.04 | 0.132 |
| 013 | 0.03 | 0.301 |
| 044 | 0.59 | 8.040 |
| 098 | 1.98 | n.a. |
| 109 | 0.02 | 0.143 |
| 111 | 3.14 | na |

EC50 values are in μg/mL.
na - could not be calculated.

EC50 values are in μg/mL.
na—could not be calculated.

Example 29

Binding of Anti-TF HuMabs to Cell Lines Expressing Different Levels of TF

Binding of anti-TF HuMabs to membrane-bound TF on cell lines expressing different levels of TF was determined by FACS analysis, essentially as described supra. Mouse anti-TF antibody followed by PE-conjugated anti-mouse IgGFc was used as a positive control. Fluorescence was measured on a FACSCanto™ II. Binding curves were analyzed essentially as described supra, using GraphPad Prism 5 software. The amount of TF molecules on cell lines was determined by Qifi Kit® (Dako, Glostrup, Denmark), according to the manufacturer's instructions. It was determined that SW480 cells express ~20,000 molecules of TF per cell, SK-OV-3 cells express ~60,000 molecules per cell, AsPC-1 cells express ~175,000 molecules per cell and MDA-MB-231 cells express ~900,000 molecules per cell.

FIG. 21 HuMab-TF-98 and -111 display similar binding characteristics as HuMab-TF-11, -13 and 109 in the high TF expressing cell line MDA-MD-231. In the cell lines with lower TF molecules per cell, for example the SK-OV-3 and SW480 cell lines, HuMab-TF-98 and 111 display different binding characteristics as compared to the other HuMab-TF antibodies.

The invention claimed is:

1. A human antibody which binds human Tissue Factor (TF), wherein said antibody:
   competes for TF binding with a reference antibody comprising a VH region comprising the sequence of SEQ ID NO:9 and a VL region comprising the sequence of SEQ ID NO:65, and
   does not compete for TF binding with a reference antibody comprising a VH region comprising the sequence of SEQ ID NO:37 and a VL region comprising the sequence of SEQ ID NO:93.

2. The antibody of claim 1, wherein the antibody is effective in inhibiting growth of established MDA-MB-231 tumors, when determined by the method described in Example 24 and/or in inhibiting growth of established BxPC3 tumors, when determined by the method described in Example 26.

3. The antibody of claim 1, wherein the antibody inhibits tissue factor induced blood coagulation with a median inhibition concentration of less than 10 nM, when determined as described in the assay in Example 19.

4. The antibody of claim 1, wherein the antibody inhibits FVIIa binding to TF, with a maximum inhibition value of inhibition of more than 80%, when determined as described in the assay in Example 15.

5. The antibody of claim 1, wherein the antibody inhibits FVIIa-induced IL-8 release by MDA-MB-231 cells, with a maximum inhibition value of inhibition of more than 40%, when determined in as described in the assay in Example 17.

6. The antibody of claim 1, wherein the antibody inhibits conversion of FX into FXa by the TF/FVIIa complex, by less than 50%, when determined as described in the assay in Example 18.

7. The antibody of claim 1, wherein said antibody competes for TF binding with an antibody comprising a VH region comprising the sequence of SEQ ID NO:9 and a VL region comprising the sequence of SEQ ID NO:65.

8. The antibody of claim 1, wherein binding to TF does not involve any one of the amino acids W in position 45, K in position 46 or Y in position 94 of TF.

9. The antibody of claim 1, wherein said antibody inhibits FVIIa induced ERK phosphorylation, with a median inhibition concentration of less than 10 nM when determined as described in the assay in Example 16.

10. The antibody of claim 1, wherein the antibody inhibits ERK phosphorylation with a median inhibition concentration of less than 10 nM, when determined as described in the assay in Example 16, and do not inhibit FVII induced IL-8 release as described in the assay in Example 17 by more than maximum 10%.

11. The antibody of claim 1, wherein the antibody is capable of inducing C3c and C4c deposition.

12. The antibody of claim 1, wherein the antibody Fab fragments binds to the extracellular domain of TF as described in Example 28 with an $EC_{50}$ value of below 0.1 µg/mL, as measured by ELISA.

13. The antibody of claim 1, wherein the antibody Fab fragments bind to the extracellular domain of TF as described in Example 28 with an $EC_{50}$ value of above 1.0 µg/mL, as measured by ELISA.

14. The antibody of claim 1, wherein the antibody Fab fragments bind to the extracellular domain of TF as described in Example 28 with an $EC_{50}$ value of below 10 µg/mL.

15. The antibody of claim 1, wherein the antibody binds to human TF and not murine TF and shows reduced binding as compared to binding to human TF to the shuffle construct 42-84 mm, containing the human sequence for TF except for amino acid 42-84, which has been replaced with mouse sequence, as described in Example 27.

16. The antibody of claim 1, wherein the antibody binds to human TF and not murine TF and shows reduced binding as compared to binding to human TF to the shuffle construct 85-122 mm, containing the human sequence for TF except for amino acid 85-122, which has been replaced with mouse sequence, as described in Example 27.

17. The antibody of claim 1, wherein the antibody binds to human TF and not murine TF and shows reduced binding as compared to binding to human TF to the shuffle construct 123-137 mm containing the human sequence for TF except for amino acid 123-137, which has been replaced with mouse sequence, as described in Example 27.

18. The antibody of claim 1, wherein the antibody binds to human TF and not murine TF and shows reduced binding as compared to binding to human TF to the shuffle construct 185-225 mm containing the human sequence for TF except for amino acid 185-225, which has been replaced with mouse sequence, as described in Example 27.

19. The antibody of claim 1, wherein the antibody binds to human TF and not murine TF and shows reduced binding as compared to binding to human TF to both the shuffle construct 226-250 mm containing the human sequence for TF except for amino acid 226-250, which has been replaced with mouse sequence, as described in Example 27.

20. The antibody according to claim 15, which shows reduced binding as compared to binding to human TF to more than one shuffle construct.

21. The antibody of claim 1, wherein the antibody comprises: a) a VH region comprising the CDR1, 2 and 3 sequences of SEQ ID NO: 10, 11 and 12 and a VL region comprising the CDR1, 2 and 3 sequences of SEQ ID NO:66, 67 and 68, b) a VH region comprising the CDR1, 2 and 3 sequences of SEQ ID NO: 14, 15 and 16 and a VL region comprising the CDR1, 2 and 3 sequences of SEQ ID NO:70, 71 and 72, c) a VH region comprising the CDR1, 2 and 3 sequences of SEQ ID NO: 18, 19, 20 and a VL region comprising the CDR1, 2 and 3 sequences of SEQ ID NO:74, 75 and 76, d) a VH region comprising the CDR1, 2 and 3 sequences of SEQ ID NO:22, 23 and 24 and a VL region comprising the CDR1, 2 and 3 sequences of SEQ ID NO:78, 79 and 80, or e) a VH region comprising the CDR1, 2 and 3 sequences of SEQ ID NO: 26, 27 and 28 and a VL region comprising the CDR1, 2 and 3 sequences of SEQ ID NO: 82, 83 and 84.

22. The antibody of claim 1 comprising: a) a VH region comprising the sequence of SEQ ID NO:9 and a VL region comprising the sequence of SEQ ID NO: 65, b) a VH region comprising the sequence of SEQ ID NO: 13 and a VL region comprising the sequence of SEQ ID NO:69, c) a VH region comprising the sequence of SEQ ID NO: 17 and a VL region comprising the sequence of SEQ ID NO:73, d) a VH region comprising the sequence of SEQ ID NO:21 and a VL region comprising the sequence of SEQ ID NO:77, or e) a VH region comprising the sequence of SEQ ID NO:25 and a VL region comprising the sequence of SEQ ID NO:81.

23. The antibody of claim 1, wherein the antibody has a kd of more than $10^{-3}$ sec$^{-1}$, when determined by the method described in Example 22 herein and/or a ka of more than $5 \times 10^4$ mol$^{-1}$ sec$^{-1}$ when determined by the method described in Example 22.

24. The antibody of claim 1 wherein the antibody has a kd of more than $10^{-3}$ sec$^{-1}$ when determined by the affinity method described in Example 22 herein, and an avidity of less than 5 nM, when determined by the avidity method described in Example 22.

25. The antibody of claim 1, wherein the antibody exhibits no binding to healthy tissue, but does exhibit binding to pancreatic tumors.

26. The antibody of claim 1 wherein the antibody inhibits the growth of established BX-PC3 tumors.

27. The antibody of claim 1, wherein the antibody further has one or more of the following properties: inhibition of proliferation, inhibition of tumor angiogenesis, induction of apoptosis of tumor cells, binding to alternatively spliced TF.

28. The antibody of claim 1, wherein the antibody is a full-length antibody.

29. The antibody of claim 1, wherein the antibody is conjugated to another moiety.

30. The antibody of claim 1, wherein the antibody is an effector-function-deficient antibody.

31. The antibody of claim 30, wherein the effector-function-deficient anti-TF antibody is a stabilized human IgG4 antibody.

32. The antibody of claim 1, wherein the antibody is a monovalent antibody.

33. The antibody of claim 32, wherein said monovalent antibody is constructed by a method comprising: i) providing a nucleic acid construct encoding the light chain of said monovalent antibody, said construct comprising a nucleotide sequence encoding the VL region of a selected antigen-specific antibody and a nucleotide sequence encoding the constant CL region of an Ig, wherein said nucleotide sequence encoding the VL region of a selected antigen-specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being; ii) providing a nucleic acid construct encoding the heavy chain of said monovalent antibody, said construct comprising a nucleotide sequence encoding the VH region of a selected antigen-specific antibody and a nucleotide sequence encoding a constant CH region of a human Ig, wherein the nucleotide sequence encoding the CH region has been modified such that the region corresponding to the hinge region and, as required by the Ig subtype, other regions of the CH region do not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen-specific antibody and said nucleotide sequence encoding the CH region of said Ig are operably linked together; iii) providing a cell expression system for producing said monovalent antibody; iv) producing said monovalent antibody by co-expressing the nucleic acid constructs of (i) and (ii) in cells of the cell expression system of (iii).

34. The antibody of claim 32, wherein the monovalent antibody comprises
(i) a variable region of an antibody which binds human TF or an antigen binding part of the said region, and
(ii) a $C_H$ region of an immunoglobulin or a fragment thereof comprising the $C_H2$ and $C_H3$ regions, wherein the $C_H$ region or fragment thereof has been modified such that the region corresponding to the hinge region and, if the immunoglobulin is not an IgG4 subtype, other regions of the $C_H$ region do not comprise any amino acid residues which are capable of forming disulfide bonds with an identical $C_H$ region or other covalent or stable non-covalent inter-heavy chain bonds with an identical $C_H$ region in the presence of polyclonal human IgG.

35. The antibody of claim 32, wherein the heavy chain has been modified such that the entire hinge has been deleted.

36. A bispecific molecule comprising an antibody of claim 1 and a second binding specificity.

37. A pharmaceutical composition comprising an antibody as defined in claim 1 and a pharmaceutically acceptable carrier.

38. A diagnostic composition comprising an antibody as defined in claim 1.

39. A kit for detecting the presence of TF in a sample comprising
an antibody of claim 1; and
instructions for use of the kit.

40. A method for detecting the presence of Tissue Factor in a sample, comprising:

contacting the sample with an antibody of claim 1 under conditions that allow for formation of a complex between the antibody or bispecific molecules and Tissue Factor; and analyzing whether a complex has been formed.

41. A method for inhibiting growth and/or proliferation of a tumor cell expressing Tissue Factor, comprising administration, to an individual in need thereof, an effective amount of an antibody of claim 1.

42. A method for treating cancer comprising administering to a subject with cancer a therapeutically effective amount of the antibody of claim 1.

43. The method of claim 42, further comprising administering one or more further therapeutic agent.

* * * * *

UNITED STATES PATENT AND TRADEMARK OFFICE

(12)         CERTIFICATE EXTENDING PATENT TERM
UNDER 35 U.S.C. § 156

| | | | |
|---|---|---|---|
| (68) | PATENT NO. | : | 9,150,658 |
| (45) | ISSUED | : | October 6, 2015 |
| (75) | INVENTOR | : | Verploegen et al. |
| (73) | PATENT OWNER | : | Genmab A/S |
| (95) | PRODUCT | : | TIVDAK® (tisotumab vedotin) |

This is to certify that an application under 35 U.S.C. § 156 has been filed in the United States Patent and Trademark Office, requesting extension of the term of U.S. Patent No. 9,150,658 based upon the regulatory review of the product TIVDAK® (tisotumab vedotin) by the Food and Drug Administration. According to United States Patent and Trademark Office records, the original expiration date of the patent as of the date of issuance of this certificate is October 8, 2032. Because it appears that the requirements of the law have been met, this certificate extends the term of the patent for the period of

(94)                                   1,077 days subject to the payment of maintenance fees as provided by law, with all rights pertaining thereto as provided by 35 U.S.C. § 156.

I have caused the seal of the United States Patent and Trademark Office to be affixed this 11th day of August 2025.

Coke Morgan Stewart
Acting Under Secretary of Commerce for Intellectual Property and Acting Director of the United States Patent and Trademark Office